(12) United States Patent
Kriesel

(10) Patent No.: US 7,220,244 B2
(45) Date of Patent: May 22, 2007

(54) INFUSION APPARATUS WITH CONSTANT FORCE SPRING ENERGY SOURCE

(75) Inventor: Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 302 days.

(21) Appl. No.: 10/634,625

(22) Filed: Aug. 4, 2003

(65) Prior Publication Data
US 2005/0033233 A1 Feb. 10, 2005

(51) Int. Cl.
A61M 5/20 (2006.01)
A61M 5/00 (2006.01)
A61K 9/22 (2006.01)

(52) U.S. Cl. ............... 604/134; 604/890.1; 604/246; 604/248; 604/207; 604/211; 604/216

(58) Field of Classification Search .......... 604/890.1, 604/891.1, 131, 133, 134, 135, 151, 153, 604/246, 247, 248, 207, 211, 216, 236
See application file for complete search history.

(56) References Cited

U.S. PATENT DOCUMENTS

| | | | |
|---|---|---|---|
| 3,731,681 A | 5/1973 | Blackshear et al. | |
| 4,056,095 A * | 11/1977 | Rey et al. ................. | 600/31 |
| 4,265,241 A * | 5/1981 | Portner et al. ............. | 604/131 |
| 4,381,006 A | 4/1983 | Genese | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,850,807 A | 7/1989 | Frantz | |
| 4,863,429 A | 9/1989 | Baldwin | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idrtss | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,336,188 A | 8/1994 | Kriesel | |
| 5,346,476 A | 9/1994 | Elson | |
| 5,380,287 A | 1/1995 | Kikuchi et al. | |
| 5,411,480 A | 5/1995 | Kriesel | |
| 5,419,771 A | 5/1995 | Kriesel | |
| 5,484,410 A | 1/1996 | Kriesel et al. | |
| 5,499,968 A | 3/1996 | Milijasevic et al. | |
| 5,514,090 A | 5/1996 | Kriesel et al. | |
| 5,545,139 A | 8/1996 | Kriesel | |
| 5,620,420 A | 4/1997 | Kriesel | |
| 5,693,018 A | 12/1997 | Kriesel et al. | |

(Continued)

Primary Examiner—Catherine S. Williams
(74) Attorney, Agent, or Firm—James E. Brunton, Esq

(57) ABSTRACT

A fluid dispenser for use in controllably dispensing fluid medicaments, such as antibiotics, oncolytics, hormones, steroids, blood clotting agents, analgesics, bio pharmaceuticals and like medicinal agents from a reservoir that has been filled from prefilled containers. The fluid dispenser includes a housing to which fill vials can be connected for filling the dispenser reservoir with the fluid, and a stored energy source provided in the form of a substantially constant-force spring that provides the force necessary to continuously and uniformly expel fluid from the device reservoir. The fluid dispenser also includes a fluid flow control assembly that precisely controls the flow of the medicament solution to the patient.

9 Claims, 67 Drawing Sheets

U.S. PATENT DOCUMENTS

| | | |
|---|---|---|
| 5,720,729 A | 2/1998 | Kriesel |
| 5,721,382 A | 2/1998 | Kriesel et al. |
| 5,735,818 A | 4/1998 | Kriesel et al. |
| 5,741,242 A | 4/1998 | Kriesel |
| 5,743,879 A | 4/1998 | Kriesel |
| 5,766,149 A | 6/1998 | Kriesel et al. |
| 5,779,676 A | 7/1998 | Kriesel et al. |
| 5,807,323 A | 9/1998 | Kriesel et al. |
| 5,836,484 A | 11/1998 | Gerber |
| 5,858,005 A | 1/1999 | Kriesel |
| 5,885,250 A | 3/1999 | Kriesel et al. |
| 5,897,530 A | 4/1999 | Jackson |
| 5,921,962 A | 7/1999 | Kriesel et al. |
| 5,925,017 A | 7/1999 | Kriesel et al. |
| 5,957,891 A | 9/1999 | Kriesel et al. |
| 5,993,425 A | 11/1999 | Kriesel |
| 6,010,482 A | 1/2000 | Kriesel et al. |
| 6,027,472 A | 2/2000 | Kriesel et al. |
| 6,030,363 A | 2/2000 | Kriesel |
| 6,045,533 A | 4/2000 | Kriesel et al. |
| 6,063,059 A | 5/2000 | Kriesel |
| 6,068,613 A | 5/2000 | Kriesel et al. |
| 6,068,614 A | 5/2000 | Kriesel et al. |
| 6,086,561 A | 7/2000 | Kriesel et al. |
| 6,090,071 A | 7/2000 | Kriesel |
| 6,095,491 A | 8/2000 | Kriesel |
| 6,126,637 A | 10/2000 | Kriesel et al. |
| 6,126,642 A | 10/2000 | Kriesel et al. |
| 6,152,898 A | 11/2000 | Olsen |
| 6,159,180 A | 12/2000 | Kriesel et al. |
| 6,176,845 B1 | 1/2001 | Kriesel et al. |
| 6,183,441 B1 | 2/2001 | Kriesel et al. |
| 6,190,359 B1 | 2/2001 | Heruth |
| 6,210,368 B1 | 4/2001 | Rogers |
| 6,236,624 B1 | 5/2001 | Kriesel et al. |
| 6,245,041 B1 | 6/2001 | Kriesel |
| 6,258,062 B1 | 7/2001 | Thielen et al. |
| 6,270,481 B1 | 8/2001 | Mason et al. |
| 6,273,133 B1 | 8/2001 | Williamson et al. |
| 6,277,095 B1 | 8/2001 | Kriesel et al. |
| 6,293,159 B1 | 9/2001 | Kriesel et al. |
| 6,319,235 B1 | 11/2001 | Yoshino |
| 6,355,019 B1 | 3/2002 | Kriesel et al. |
| 6,391,006 B1 | 5/2002 | Kriesel et al. |
| 6,394,980 B2 | 5/2002 | Kriesel et al. |
| 6,398,760 B1 | 6/2002 | Danby |
| 6,416,495 B1 * | 7/2002 | Kriesel et al. .............. 604/132 |
| 6,485,461 B1 | 11/2002 | Mason et al. |
| 6,537,249 B2 | 3/2003 | Kriesel et al. |
| 6,542,350 B1 | 4/2003 | Rogers |
| 6,569,125 B2 | 5/2003 | Jepson et al. |
| 6,645,175 B2 | 11/2003 | Kriesel et al. |
| 6,669,668 B1 | 12/2003 | Kleeman et al. |

* cited by examiner

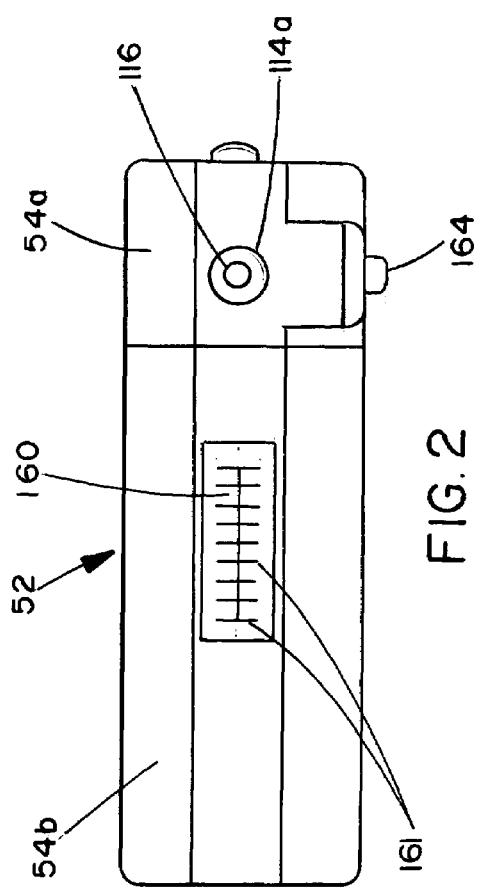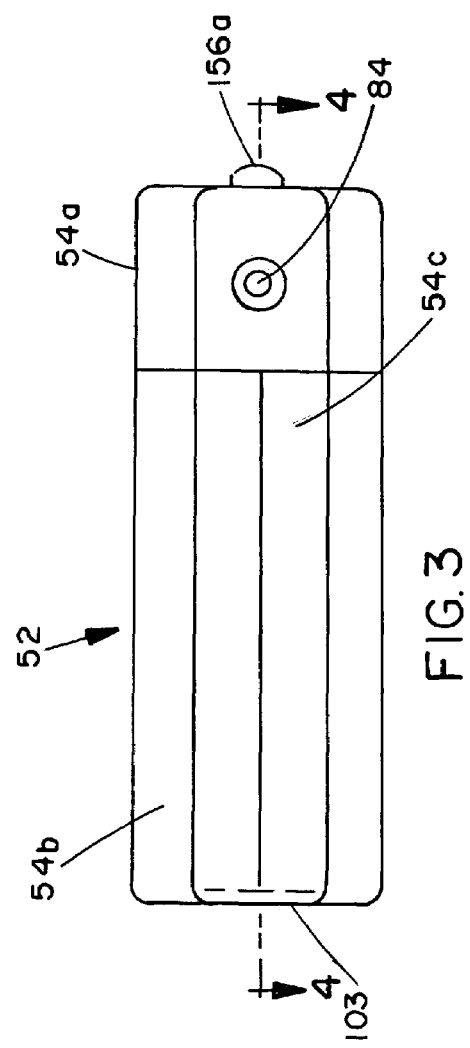

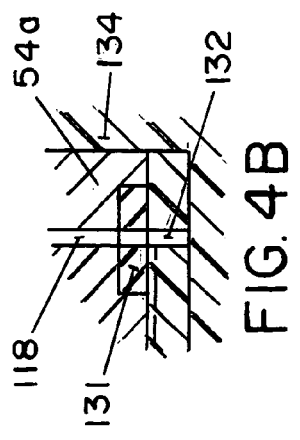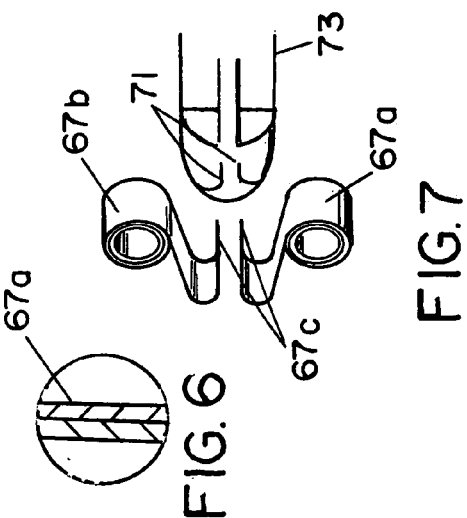

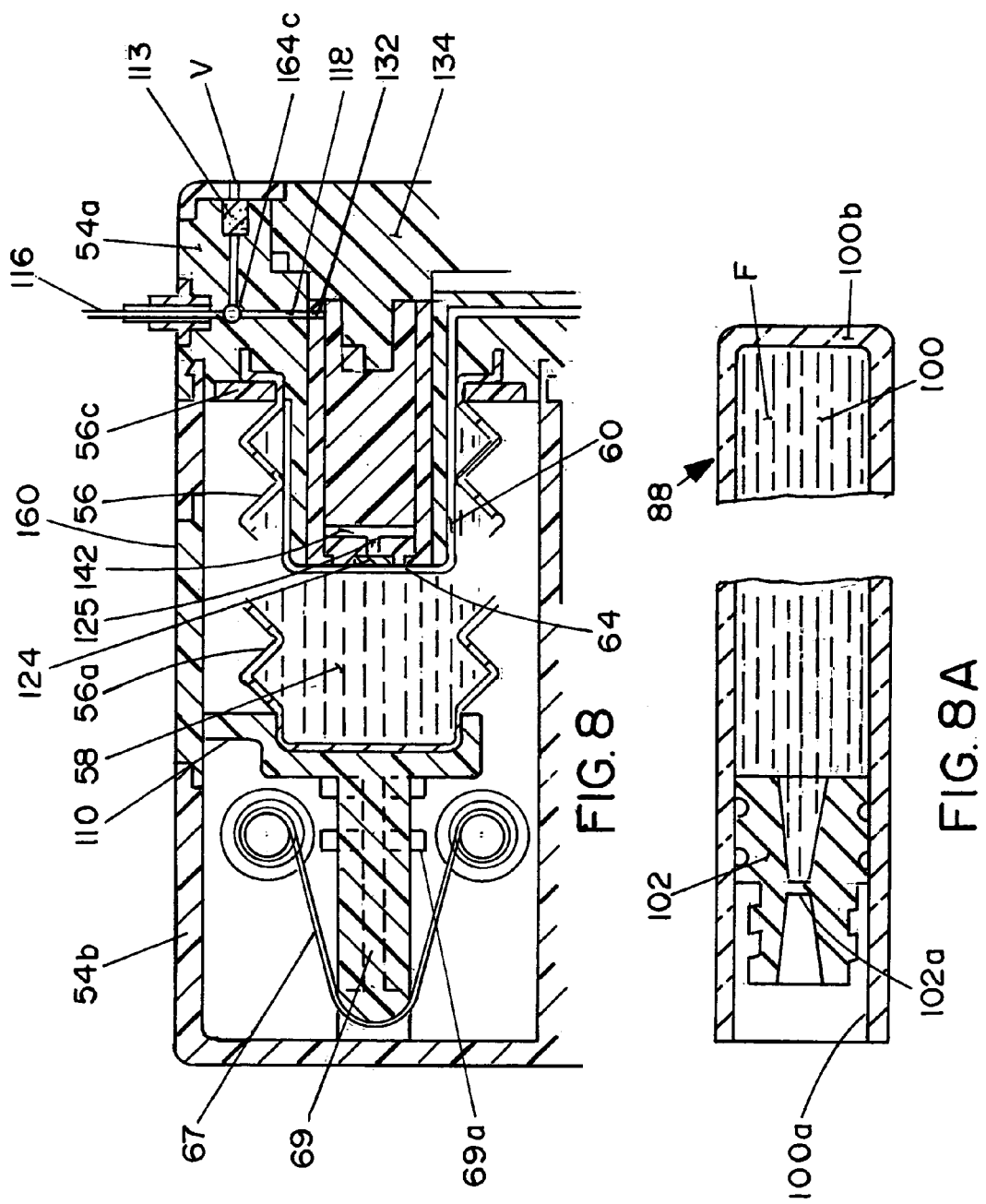

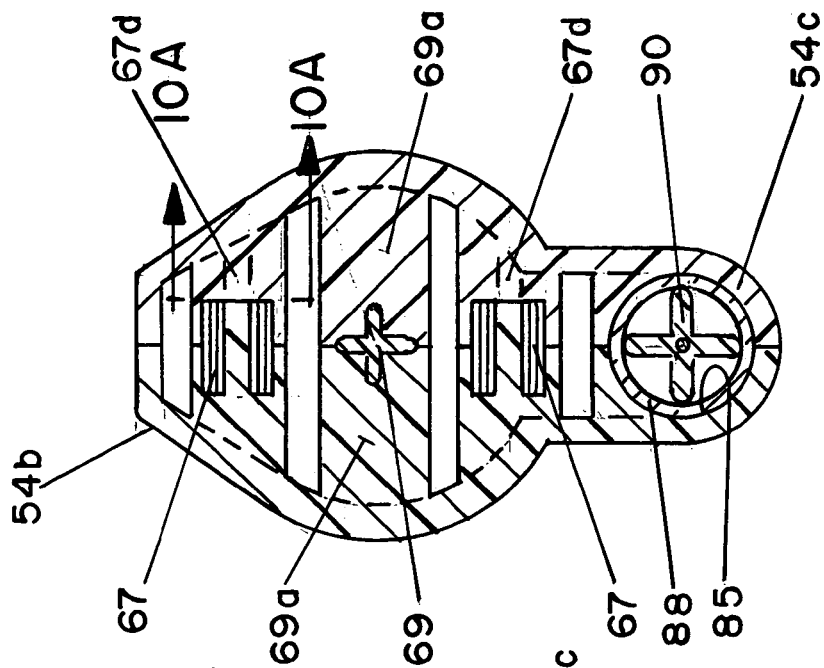
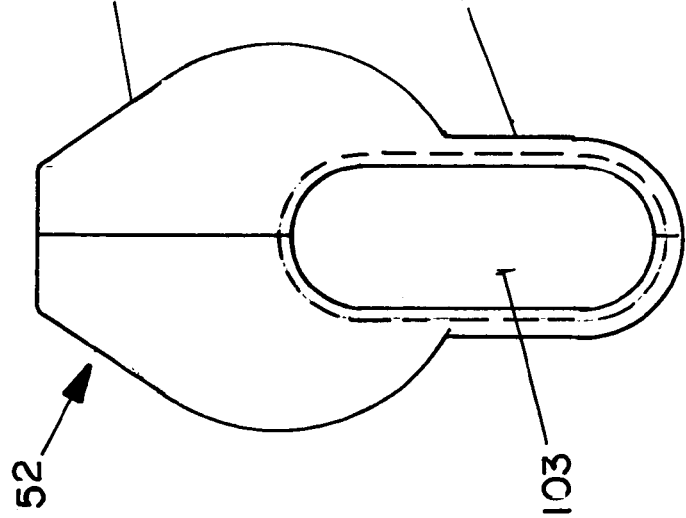
FIG. 9
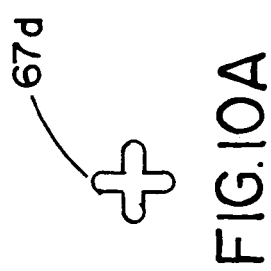
FIG. 10A

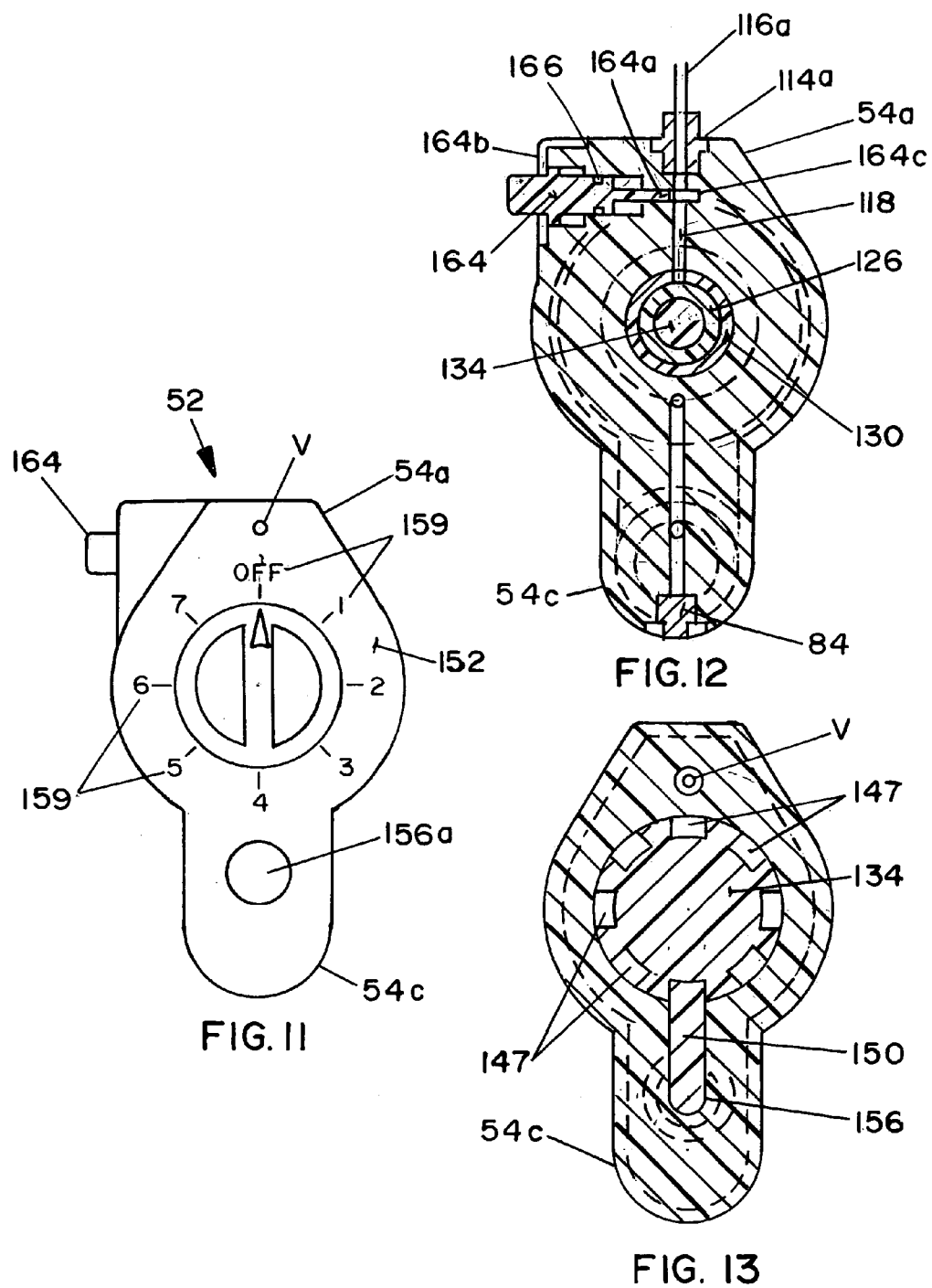

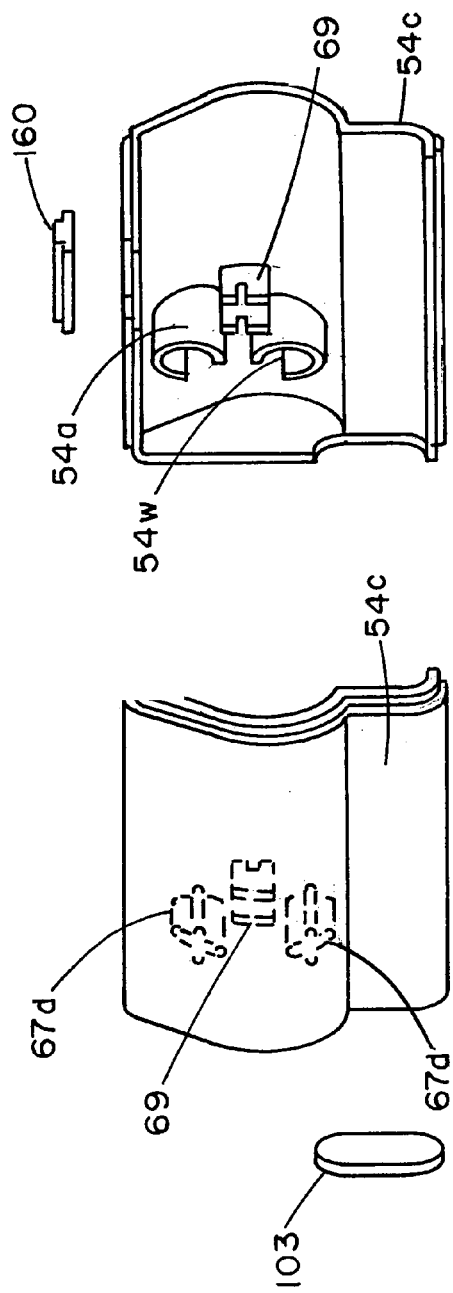
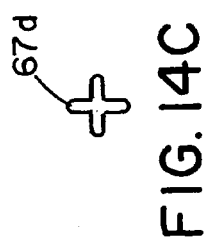
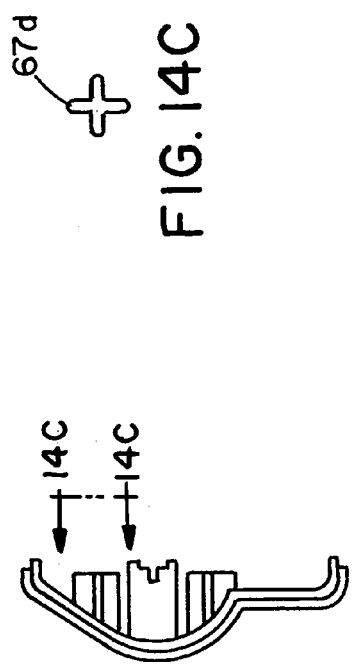
FIG. 14A
FIG. 14B
FIG. 14C

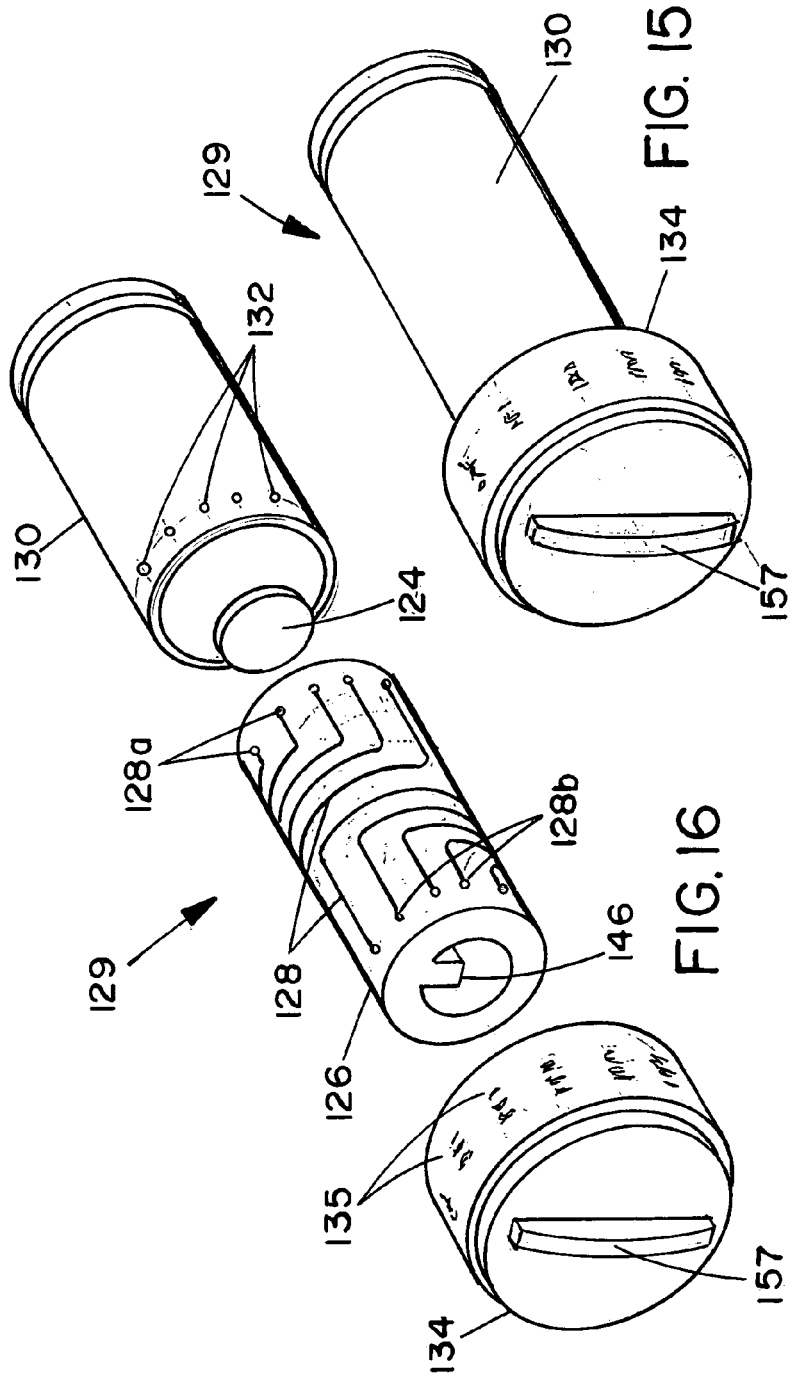

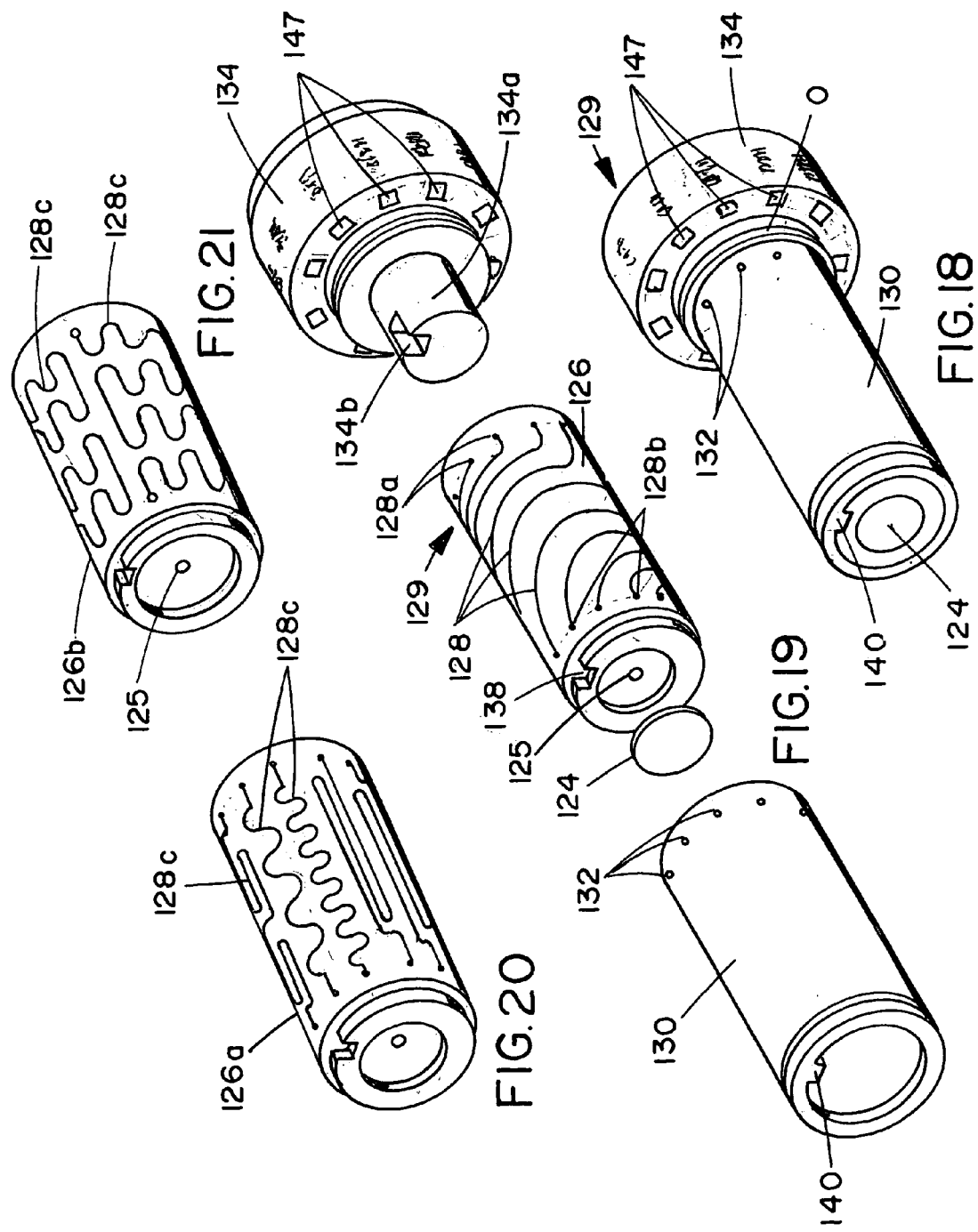

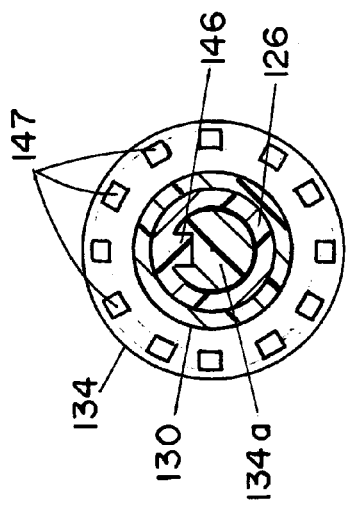
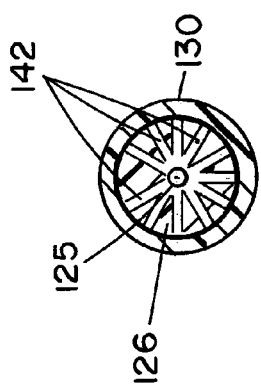
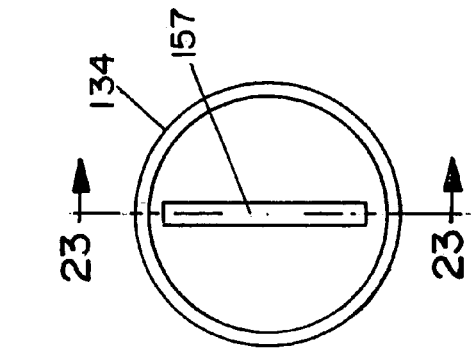
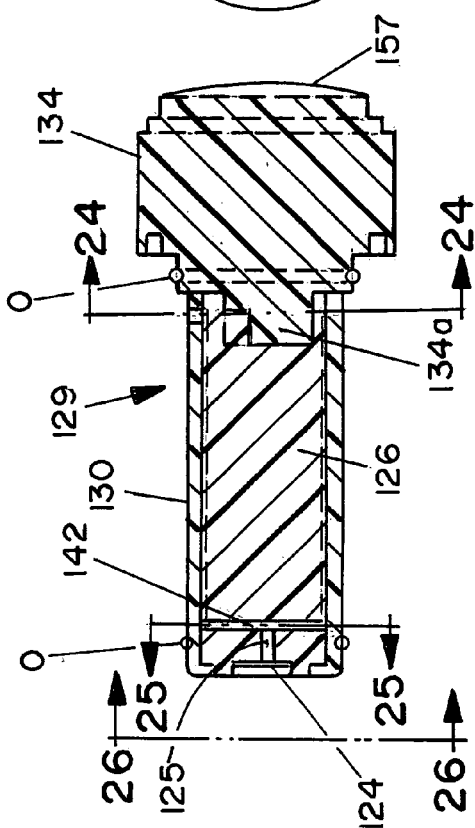
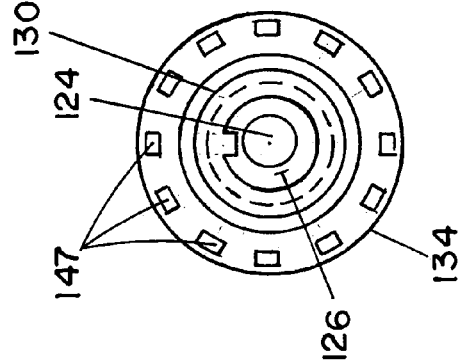

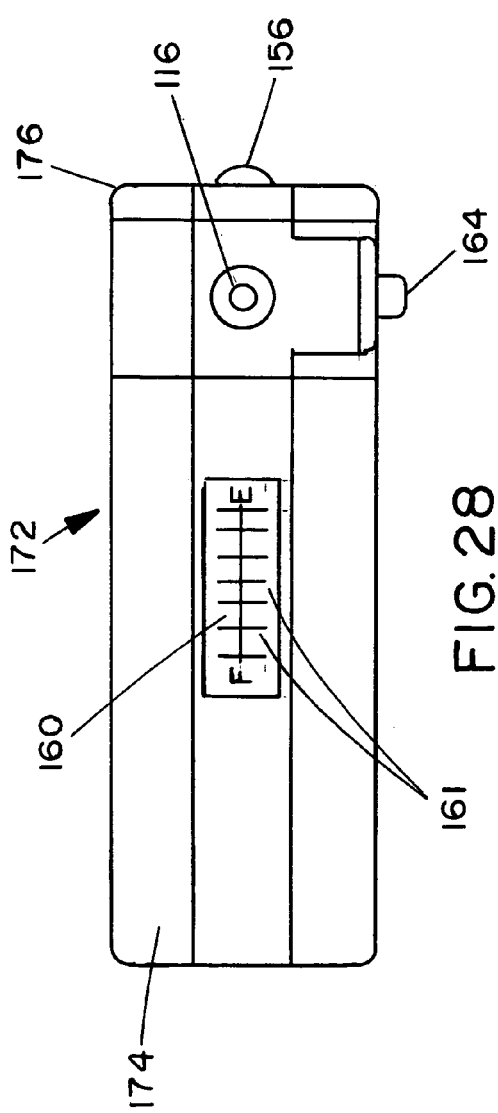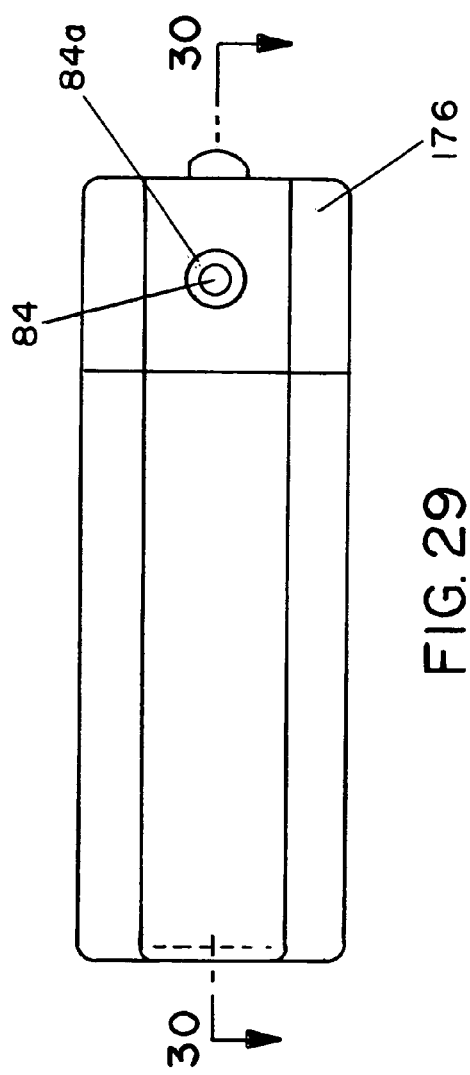
FIG. 28
FIG. 29

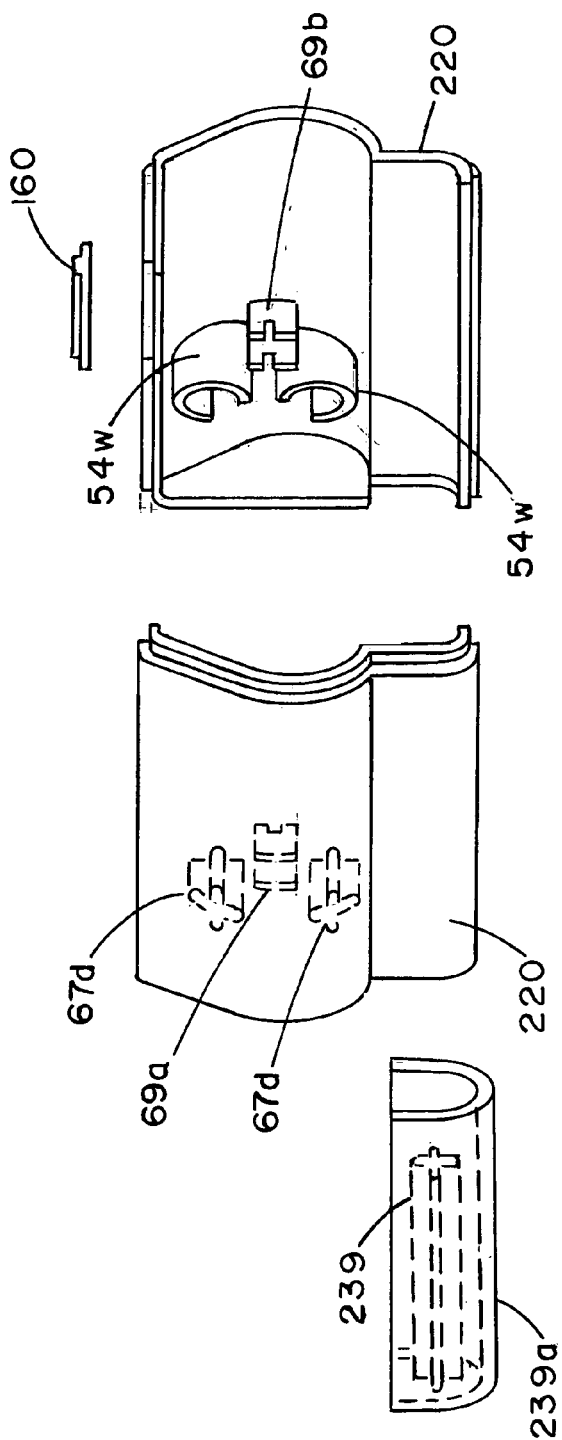
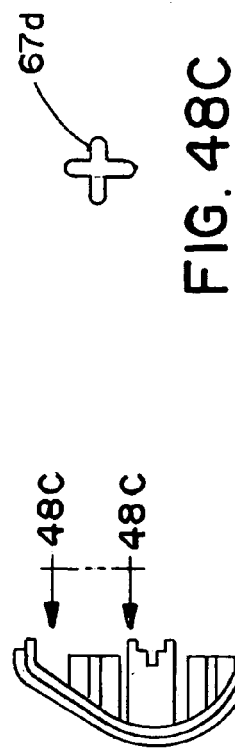

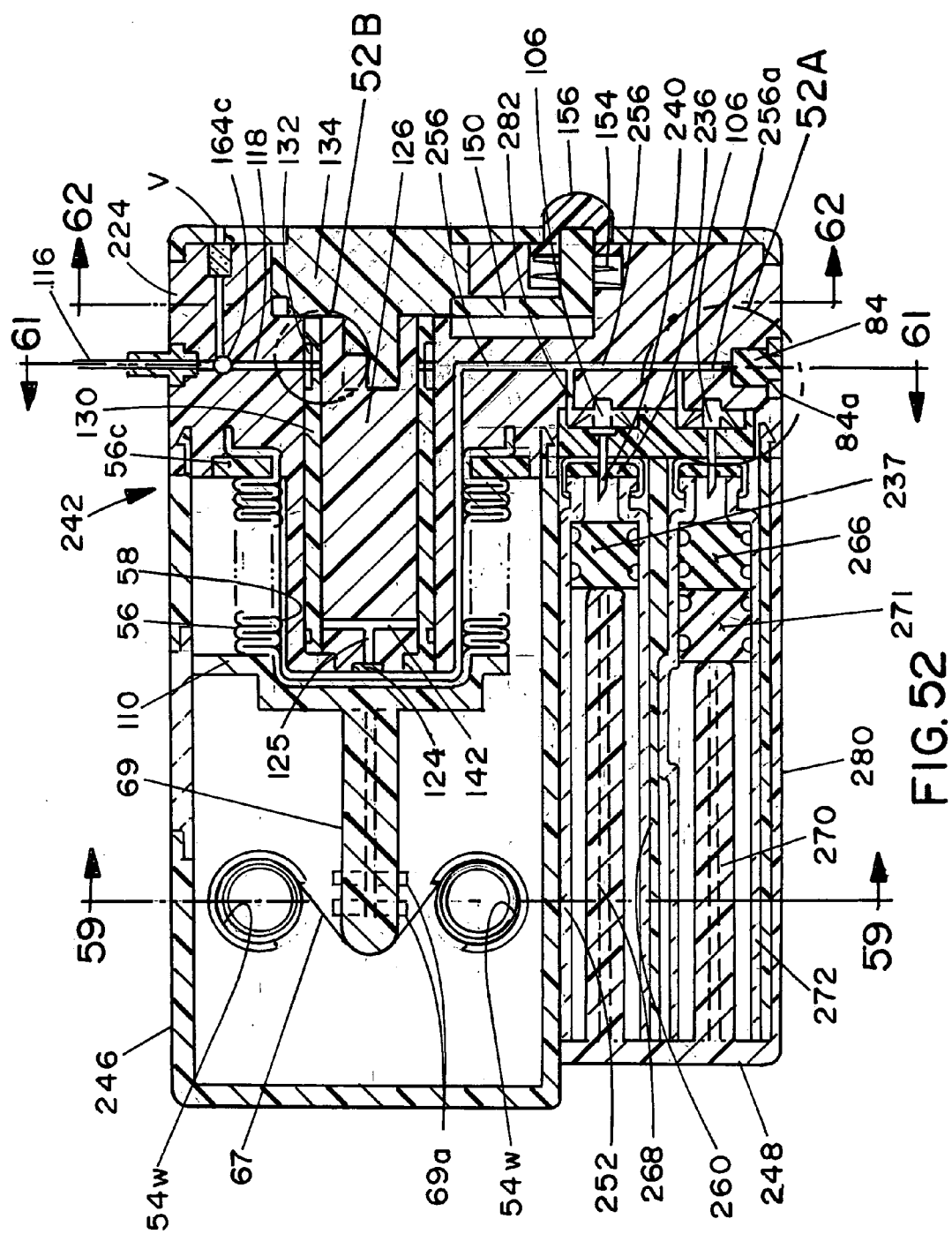

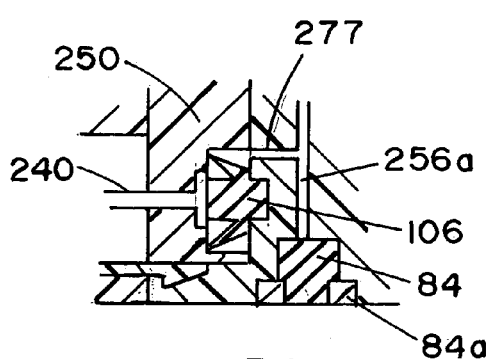
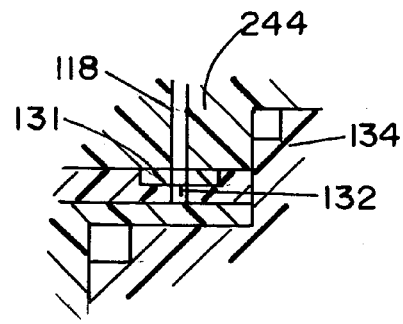# 
FIG. 52A
FIG. 52B
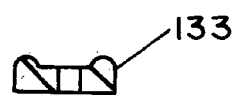
FIG. 52C
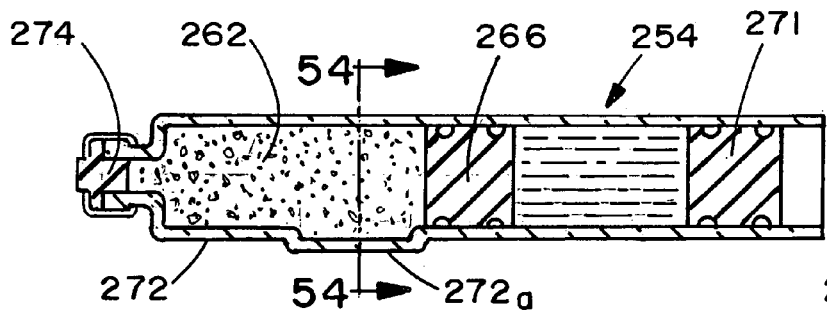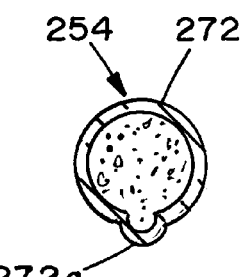
FIG. 53
FIG. 54
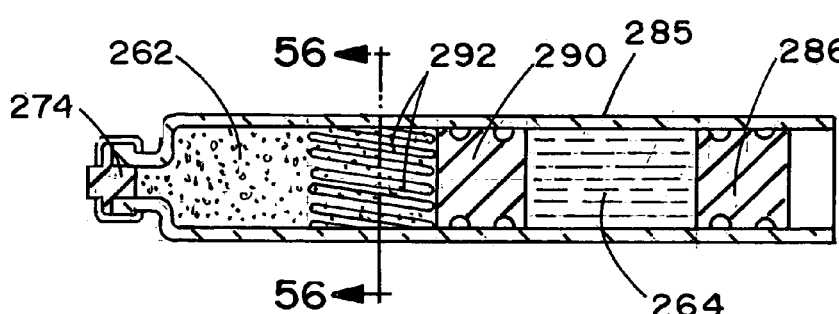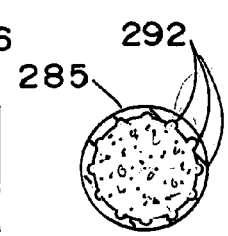
FIG. 55
FIG. 56

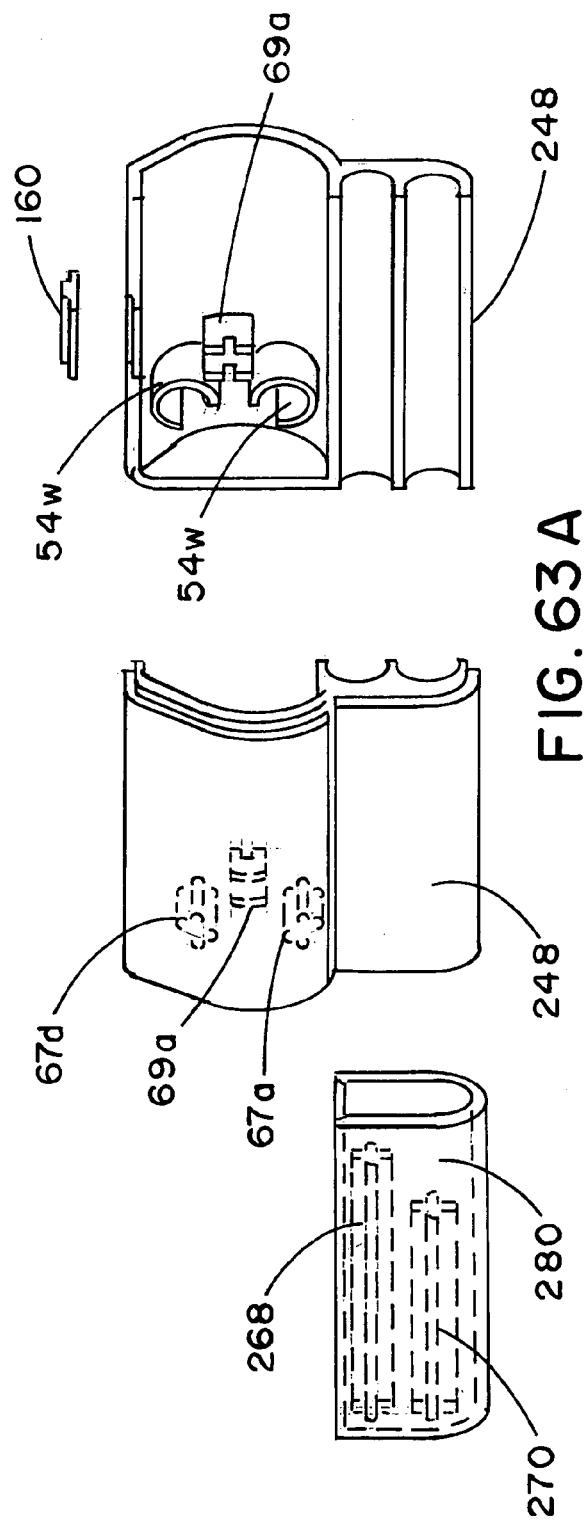
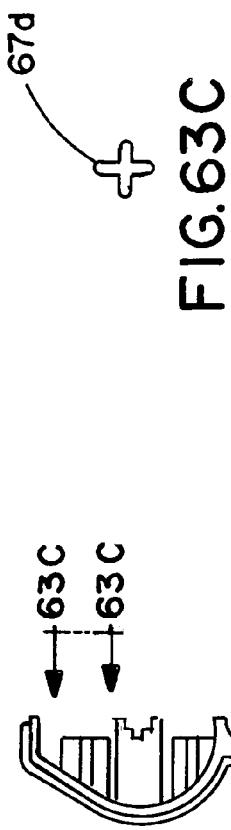
FIG. 63A
FIG. 63B
FIG. 63C

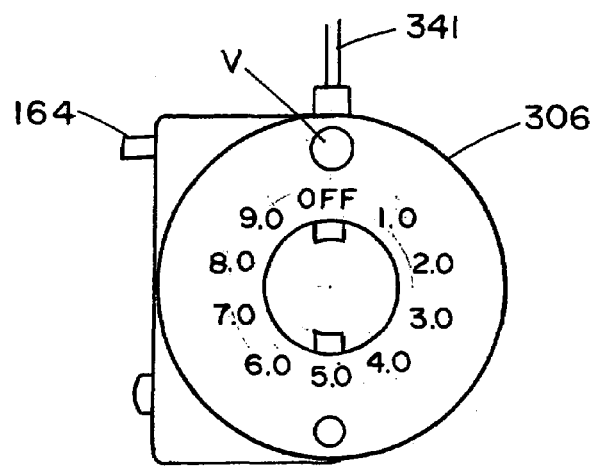
FIG. 72
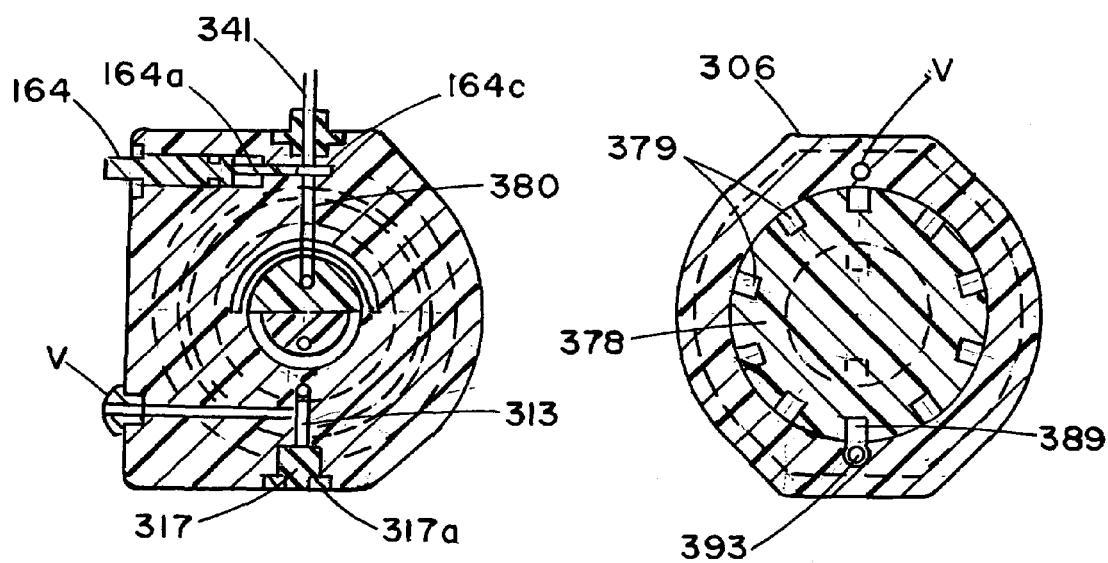
FIG. 73
FIG. 74

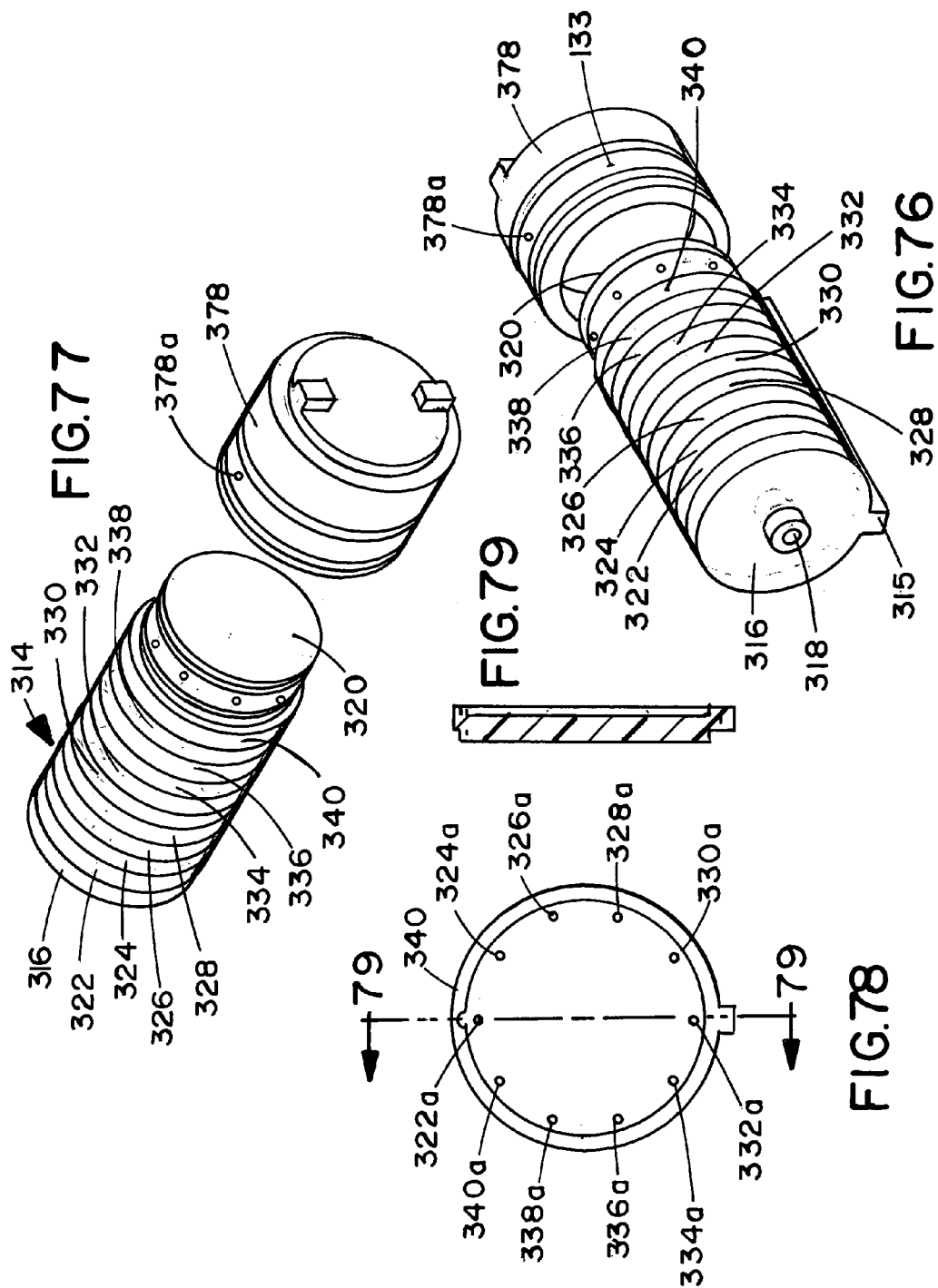

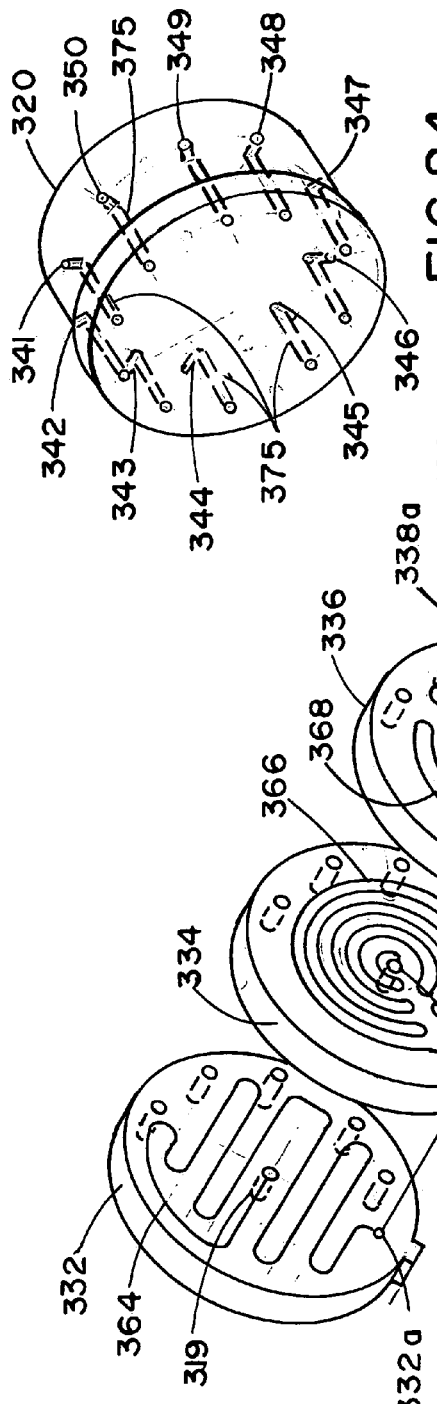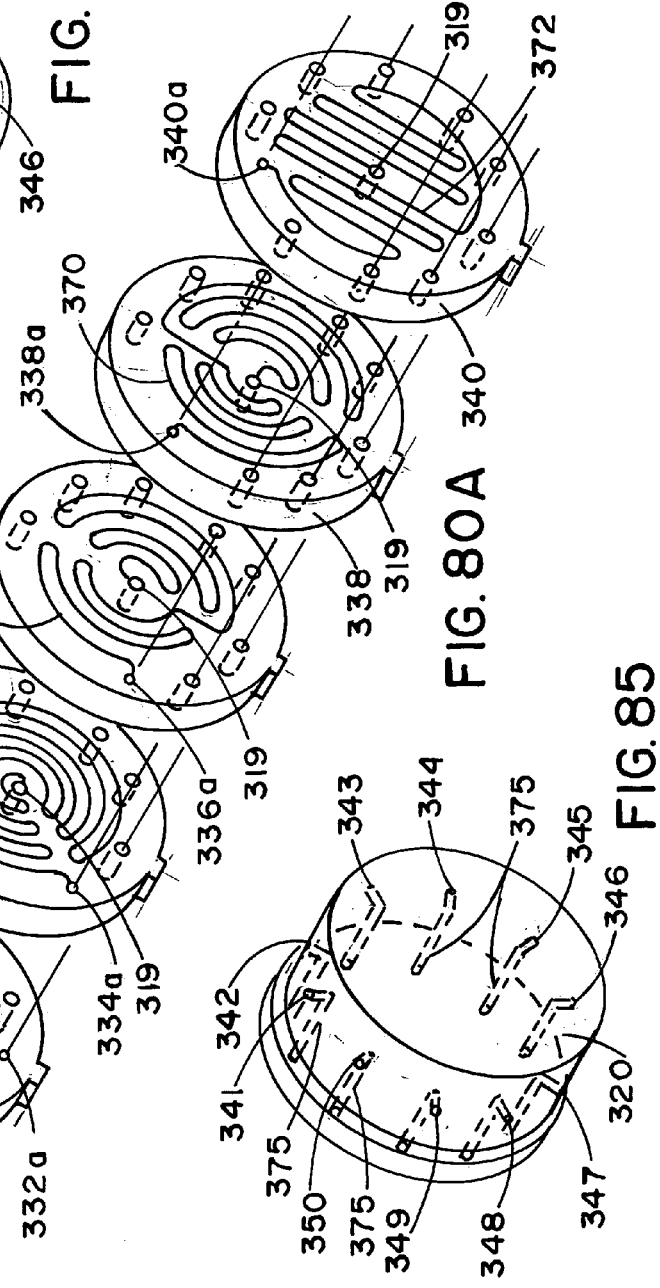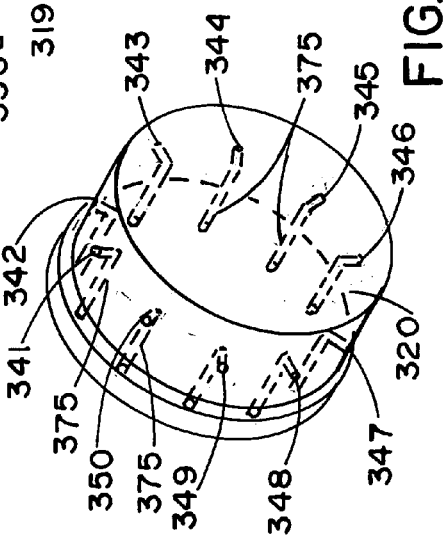

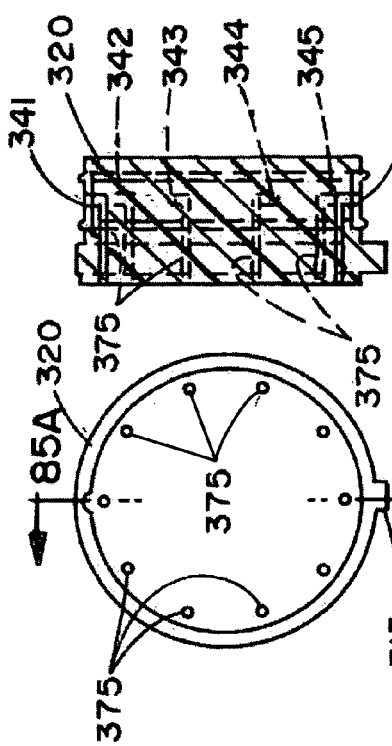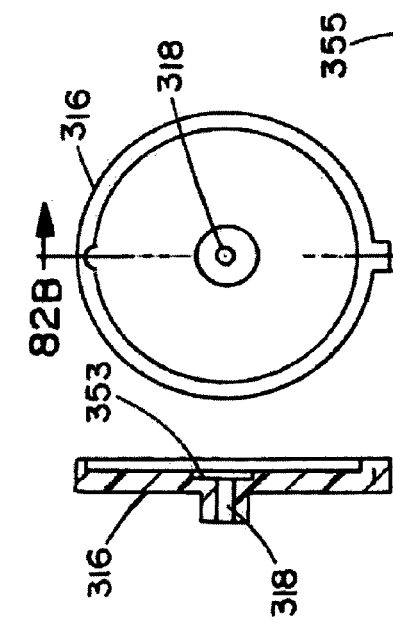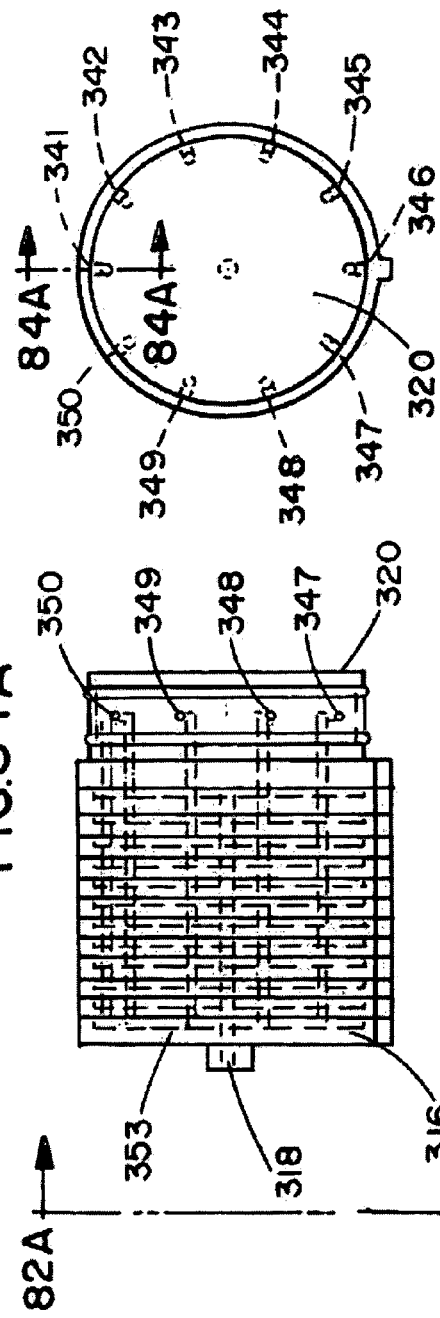

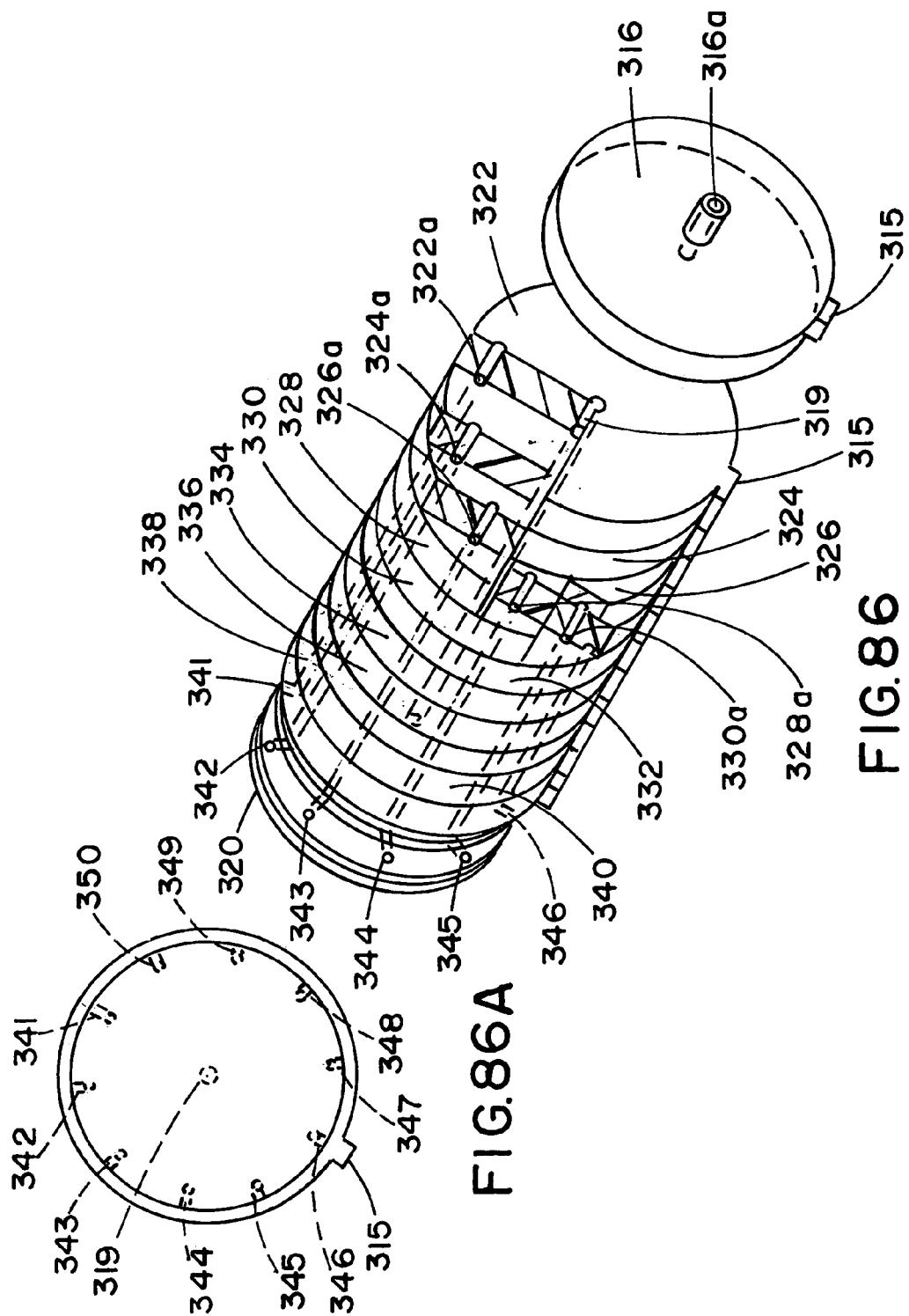

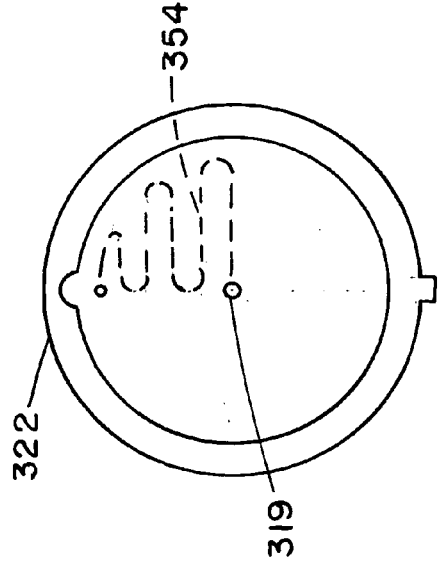
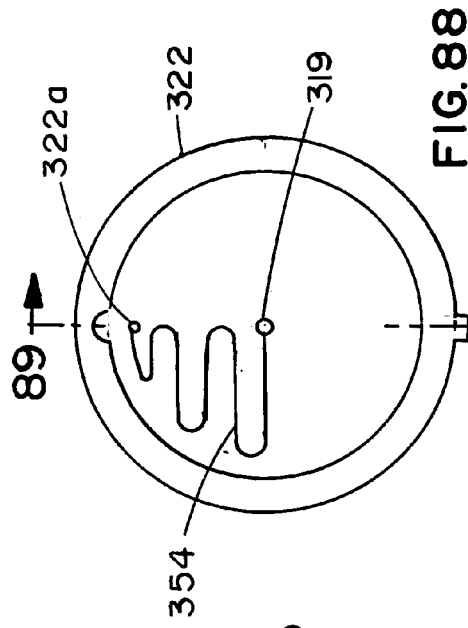
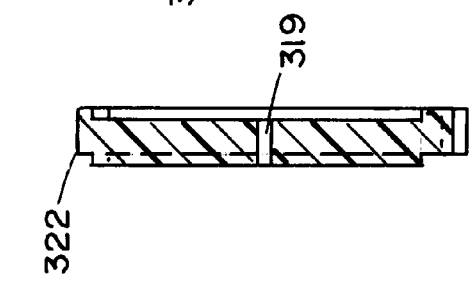
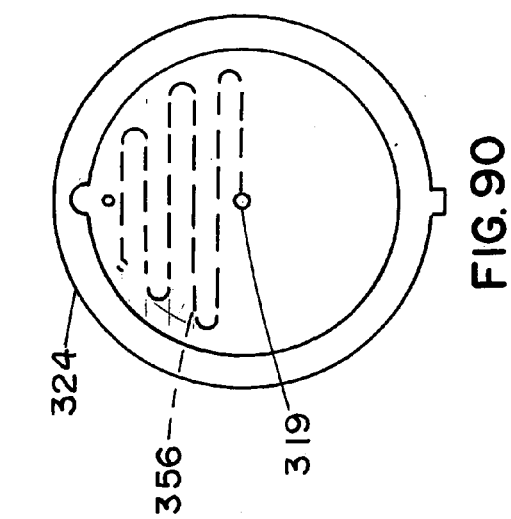
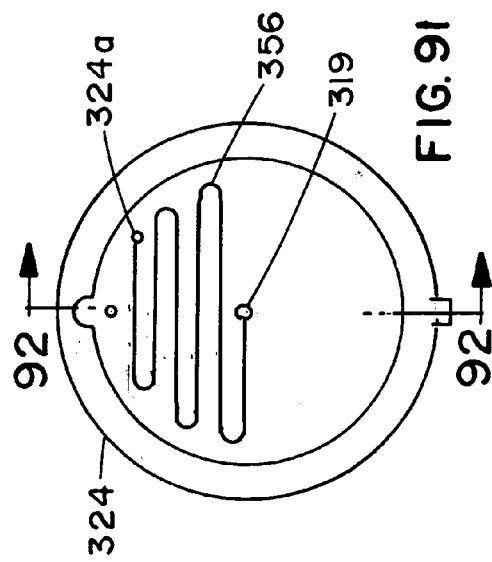
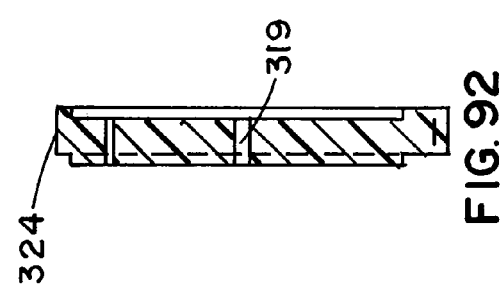

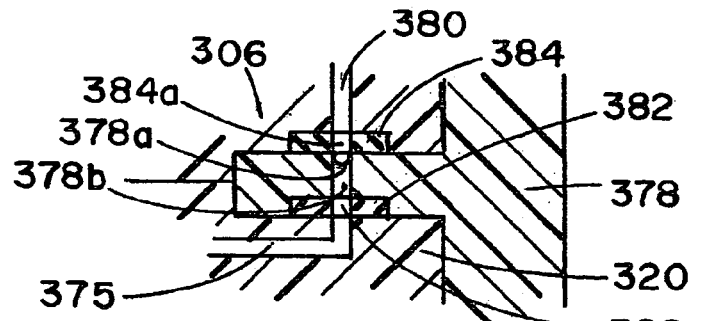
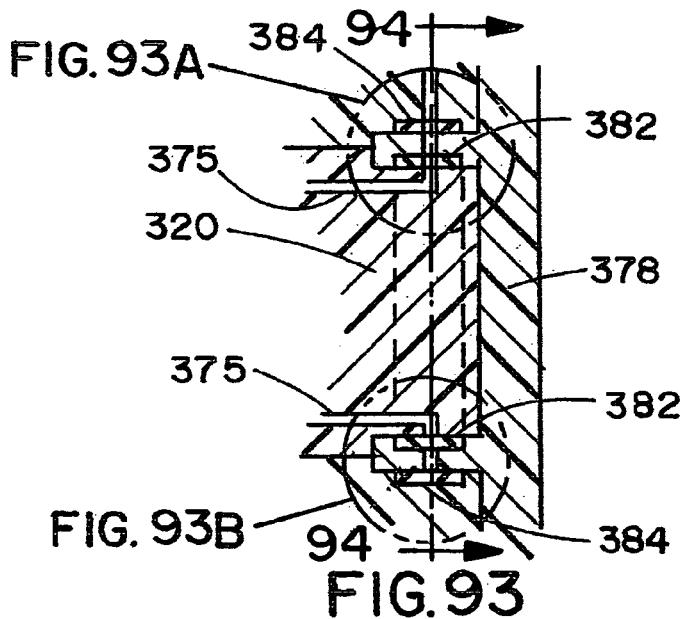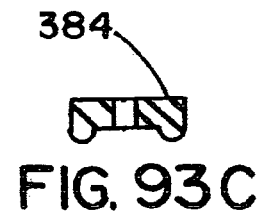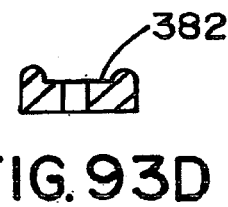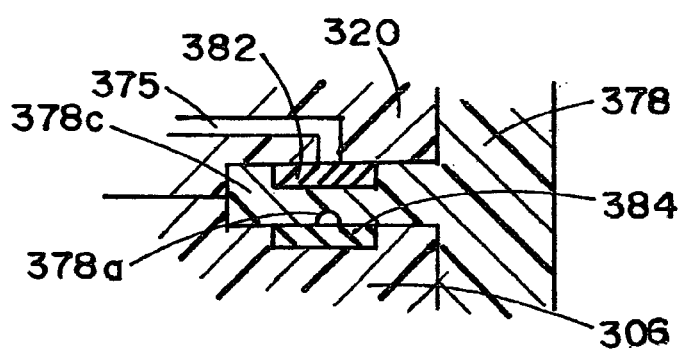

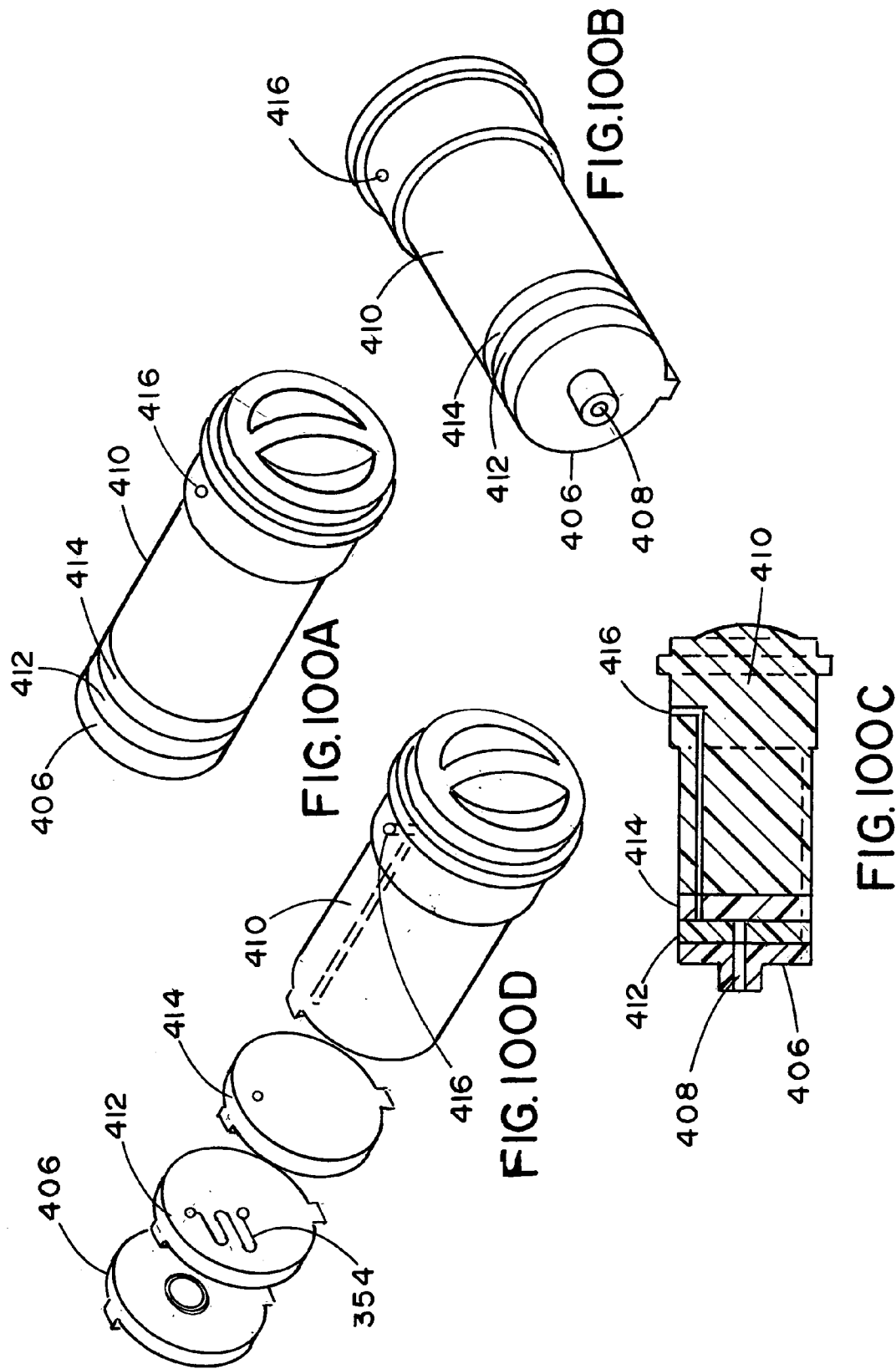

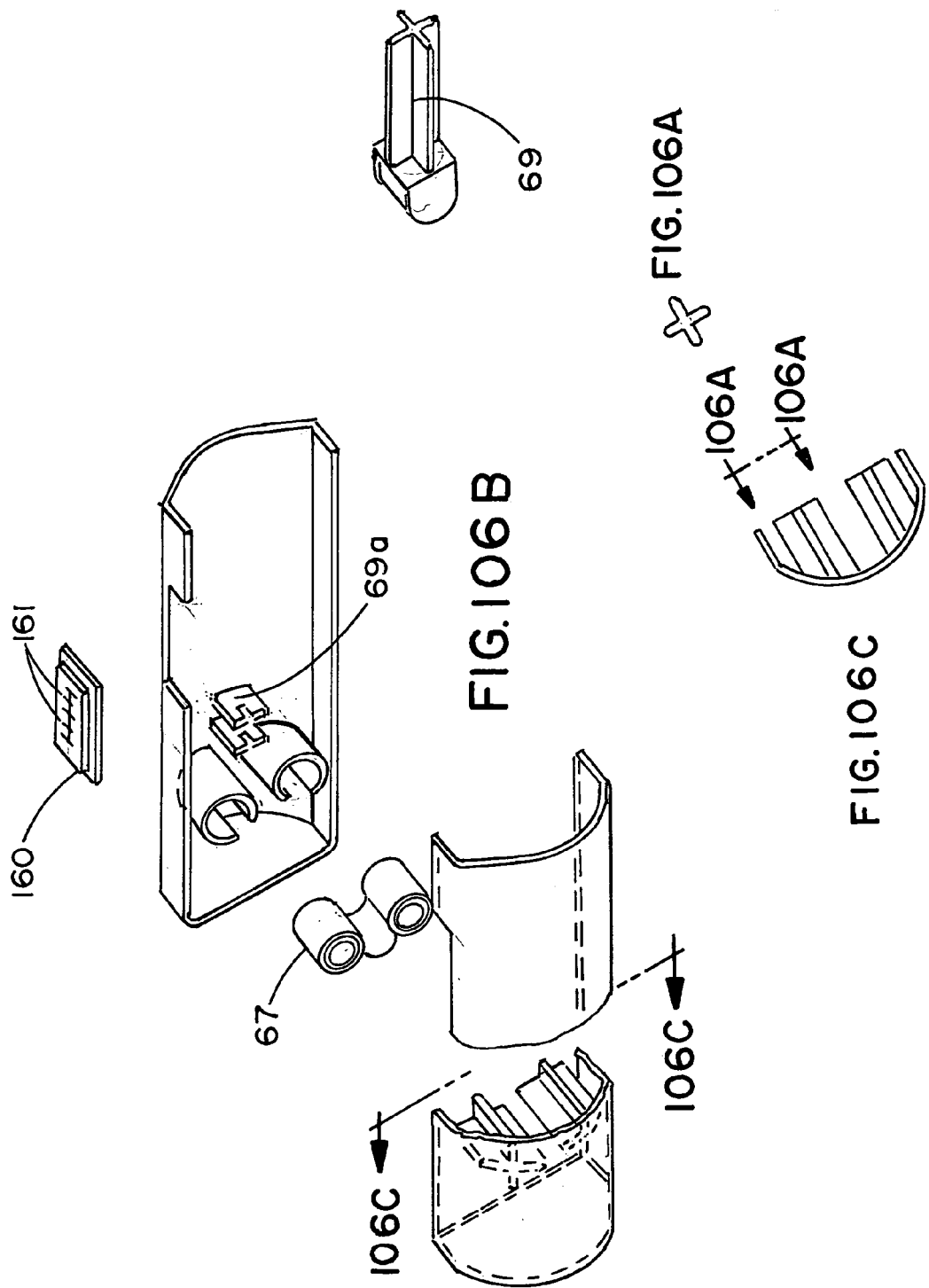

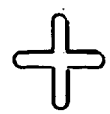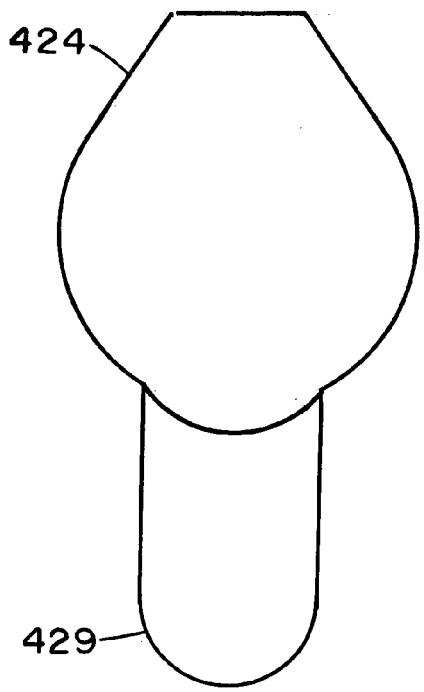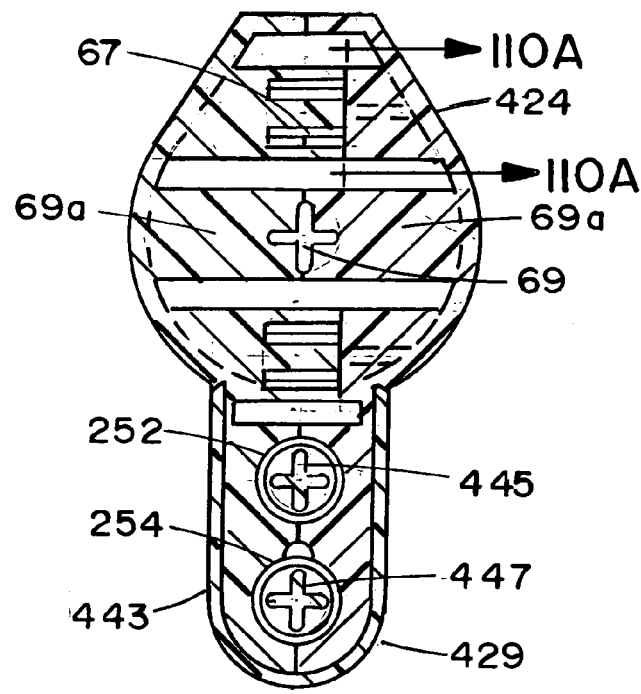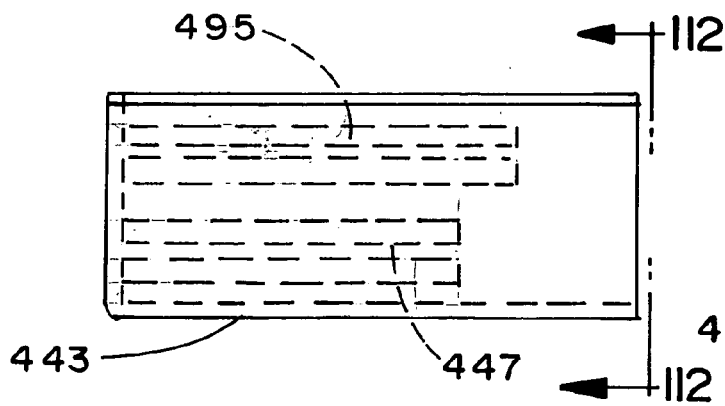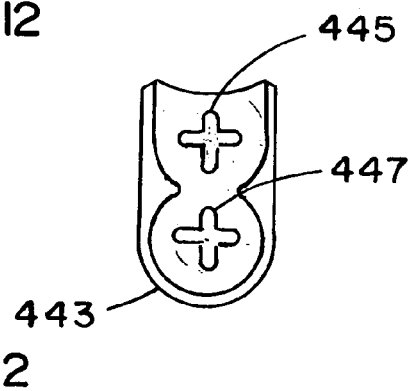

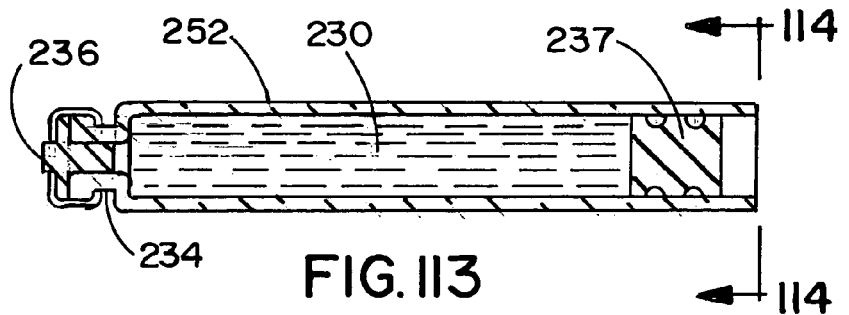
FIG. 113    FIG. 114
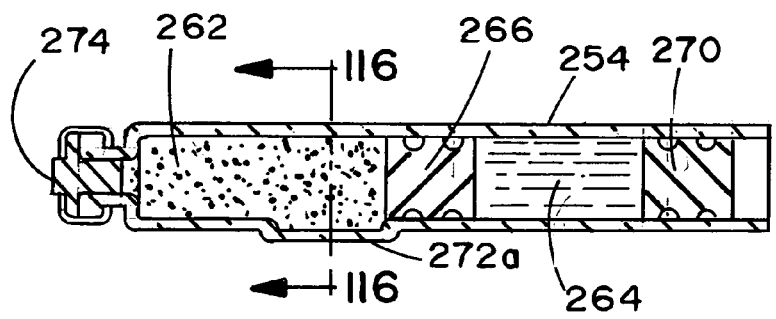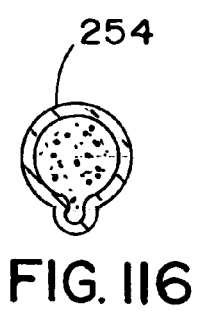
FIG. 115    FIG. 116
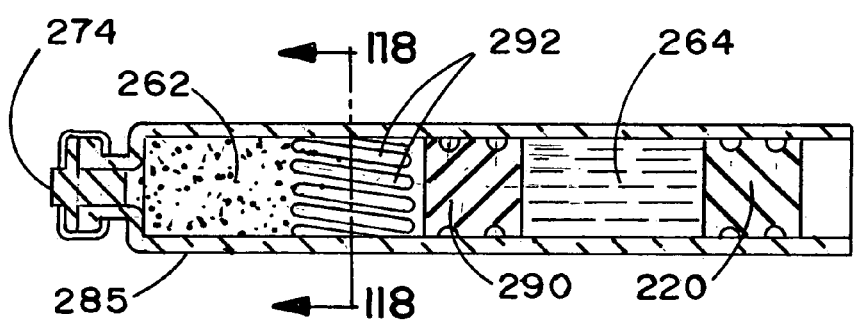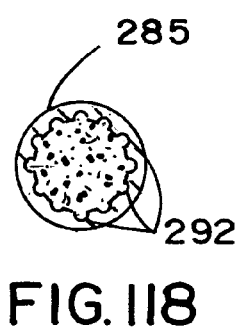
FIG. 117    FIG. 118

INFUSION APPARATUS WITH CONSTANT FORCE SPRING ENERGY SOURCE

BACKGROUND OF THE INVENTION

1. Field of the Invention

The present invention relates generally to medicament infusion devices. More particularly, the invention concerns an improved apparatus for infusing medicinal agents into an ambulatory patient at specific rates over extended periods of time, which apparatus includes a novel constant force spring energy source, and a novel flow rate control means for precisely controlling the rate of fluid flow from the reservoir of the device.

2. Discussion of the Prior Art

A number of different types of medicament dispensers for dispensing medicaments to ambulatory patients have been suggested. Many of the devices seek either to improve or to replace the traditional gravity flow and hypodermic syringe methods, which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus.

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose can result in a toxic reaction.

For those patients that require frequent injections of the same or different amounts of medicament, the use of the hypodermic syringe method of delivery is common. However, for each injection, it is necessary to first draw the injection dose into the syringe, then check the dose and, after making certain that all air has been expelled from the syringe, finally, inject the dose either under bolus or slow push protocol. This cumbersome and tedious procedure creates an unacceptable probability of debilitating complications, particularly for the elderly and the infirm.

As will be appreciated from the discussion, which follows, the apparatus of the present invention is uniquely suited to provide precise fluid delivery management at a low cost in those cases where a variety of precise dosage schemes with infusion over time are of utmost importance. An important aspect of the apparatus of the present invention is the provision of novel fill means for filling the reservoir of the device using a conventional medicament vials or cartridge containers of various types having a pierceable septum. Another unique feature of the apparatus of the present invention is the provision of various fluid flow rate control means, including an embedded microfluidic capillary flow rate control means which enables precise control of the rate of fluid flow of the medicament to the patient. More particularly, the apparatus of the present invention includes a unique, adjustable fluid flow rate mechanism, which enables the fluid contained within the reservoir of the device to be precisely dispensed at various selected rates over extended periods of time.

The apparatus of the present invention can be used with minimal professional assistance in an alternate health care environment, such as the home. By way of example, devices of the invention can be comfortably and conveniently removably affixed to the patient's body or clothing and can be used for the continuous infusion of injectable anti-infectives, hormones, steroids, blood clotting agents, analgesics, and like medicinal agents. Similarly, the devices of the invention can be used for most IV chemotherapy and can accurately deliver fluids to the patient in precisely the correct quantities and at extended micro fusion rates over time.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a substantially constant-force spring that provides the force necessary to uniformly and precisely dispense, from the device reservoir, that is filled with various solutions from standard prefilled vial containers that can be conveniently loaded into the apparatus. Because of the simplicity of construction of the apparatus of the invention, and the straightforward nature of the energy source, the apparatus can be manufactured at low cost without in any way sacrificing accuracy and reliability.

With regard to the prior art, one of the most versatile and unique fluid delivery apparatus developed in recent years is that developed by the present inventor and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to the present applicant, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container, which is housed within the body of the device. After having been deformed, the polymeric, elastomeric member will return to its starting configuration in a highly predictable manner.

Another important prior art fluid delivery device is described in the U.S. Pat. No. 6,063,059 also issued to the present inventor. This device, while being of a completely different construction embodies a compressible-expandable stored energy source somewhat similar to that used in the apparatus of the present invention.

Still another prior art fluid delivery device, in which the present inventor is also named as an inventor, is described in U.S. Pat. No. 6,086,561. This latter patent incorporates a fill system that makes use of conventional vials and cartridge medicament containers.

SUMMARY OF THE INVENTION

It is an object of the present invention to provide a compact fluid dispenser for use in controllably dispensing fluid medicaments, such as, antibiotics, oncolytics, hormones, steroids, blood clotting agents, analgesics, bio pharmaceuticals and like medicinal agents from a reservoir that has been filled from prefilled containers.

Another object of the invention is to provide a small, compact fluid dispenser that includes a housing to which fill vials can be connected for filling the dispenser reservoir with the fluid.

Another object of the invention is to provide a dispenser of in which a stored energy source is provided in the form of a substantially constant-force spring that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a dispenser that includes a disabling mechanism for disabling the device and rendering it inert following use.

Another object of the invention is to provide a fluid dispenser which is adapted to be used at point of care being there filled with conventional prefilled drug containers to deliver beneficial agents therefrom in a precise and sterile manner.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir Another object of the invention is to provide a self-contained medicament dispenser which is of very simple construction and yet extremely reliable in use.

Another object of the invention is to provide a fluid dispenser as described in the preceding paragraphs which is easy and inexpensive to manufacture in large quantities.

BRIEF DESCRIPTION OF THE DRAWINGS

FIG. 2 is a top plan view of the embodiment of the medicament infusion apparatus shown in FIG. 1.

FIG. 3 is a bottom plan view of the apparatus shown in FIG. 1.

FIG. 4A is a greatly enlarged, fragmentary cross-sectional view of a portion of the bellows component of the apparatus shown in FIG. 4.

FIG. 4B is an enlarged, cross-sectional view of the area designated as 4B in FIG. 4.

FIG. 4B-1 is an enlarged, cross-sectional view of the elastomeric band shown in FIG. 4B.

FIG. 4C is an enlarged, cross-sectional view of the area designated as 4C in FIG. 4.

FIG. 4C-1 is an enlarged, cross-sectional view of the elastomeric band shown in FIG. 4C.

FIG. 5 is an enlarged, generally perspective view of one form of the constant force spring of the apparatus shown in FIG. 4.

FIG. 6 is an enlarged, cross-sectional view of the area designated as "6" in FIG. 5.

FIG. 7 is an enlarged, generally perspective view of an alternate form of the constant force spring of the apparatus of the invention.

FIG. 8 is a cross-sectional view similar to FIG. 4, but showing the fluid reservoir filled with fluid.

FIG. 8A is an enlarged, cross-sectional view of the fill vial of the apparatus of the invention shown in FIG. 4.

FIG. 9 is a left end view of the apparatus shown in FIG. 1.

FIG. 10 is a cross-sectional view taken along lines 10—10 of FIG. 4.

FIG. 10A is a cross-sectional view taken along lines 10A—10A of FIG. 10.

FIG. 11 is a right end view of the apparatus shown in FIG. 1.

FIG. 12 is a cross-sectional view taken along lines 12—12 of FIG. 4.

FIG. 13 is a cross-sectional view taken along lines 13—13 of FIG. 4.

FIG. 14B is an end view of the snap together housing component shown in the lower left hand portion of FIG. 14A.

FIG. 15 is a generally perspective, front view of one form of the fluid flow control assembly of the apparatus of the invention.

FIG. 16 is a generally perspective, exploded front view of the fluid flow control assembly shown in FIG. 15.

FIG. 17 is a greatly enlarged, fragmentary cross-sectional view of one of the flow control channels formed in the flow control member shown in the central portion of FIG. 16.

FIG. 18 is a generally perspective, rear view of the fluid flow control assembly of the apparatus of the invention.

FIG. 19 is a generally perspective, exploded rear view of the fluid flow control assembly shown in FIG. 18.

FIG. 20 is a generally perspective view of an alternate form of the flow control member of the invention.

FIG. 21 is a generally perspective view of still another form of the flow control member of the invention.

FIG. 22 is a front view of the assembly shown in FIG. 15.

FIG. 23 is a cross-sectional view taken along lines 23—23 of FIG. 22.

FIG. 24 is a cross-sectional view taken along lines 24—24 of FIG. 23.

FIG. 25 is a cross-sectional view taken along lines 25—25 of FIG. 23.

FIG. 26 is a view taken along lines 26—26 of FIG. 23.

FIG. 28 is a top plan view of the embodiment of the medicament infusion apparatus shown in FIG. 27.

FIG. 29 is a bottom plan view of the apparatus shown in FIG. 27.

FIGS. 48 and 48A when considered together comprise a generally perspective exploded view of the assembly shown in FIG. 41 (hereinafter collectively referred to as FIG. 41).

FIG. 48B is an end view of the snap together housing component shown in the lower left hand portion of FIG. 48A.

FIG. 48C is a view taken along lines 48C—48C of the FIG. 48B.

FIG. 52 is a cross-sectional view taken along lines 52—52 of FIG. 51.

FIG. 52A is an enlarged, cross-sectional view of the area designated as 52A in FIG. 52

FIG. 52B is an enlarged, cross-sectional view of the area designated as 52B in FIG. 52.

FIG. 52C is an enlarged, cross-sectional view of the elastomeric sealing band shown in FIG. 52B.

FIG. 53 is an enlarged cross-sectional view of the lowermost cartridge reconstitution vial of the apparatus of the invention shown in FIG. 52.

FIG. 54 is a cross-sectional view taken along lines 54—54 of FIG. 53.

FIG. 55 is an enlarged cross-sectional view of an alternate form of the lowermost cartridge fill by pass vial of the apparatus of the invention shown in FIG. 52.

FIG. 56 is a cross-sectional view taken along lines 56—56 of FIG. 55.

FIGS. 63 and 63A when considered together comprise a generally perspective, exploded view of the assembly shown in FIG. 52 (hereinafter collectively referred to as FIG. 63)

FIG. 63B is an end view of the snap together having component shown in the lower left hand portion of FIG. 63A.

FIG. 63B is a view taken along lines 63B—63B of FIG. 63B.

FIG. 67A is an enlarged, cross-sectional view of the area designated as 67A in FIG. 67.

FIG. 72 is a right end view of the apparatus shown in FIG. 64.

FIG. 73 is a cross-sectional view taken along lines 73—73 of FIG. 67.

FIG. 74 is a cross-sectional view taken along lines 74—74 of FIG. 67.

FIG. 76 is a generally perspective, exploded view of the flow rate control means of this latest form of the apparatus of the present invention.

FIG. 77 is a generally perspective, front exploded view of the flow rate control means shown in FIG. 76.

FIG. 78 is a front view of the forward most rate control plate of the flow control means shown in FIG. 78.

FIG. 79 is a cross-sectional view taken along lines 79—79 of FIG. 78.

FIG. 80 and FIG. 80A, when considered together comprise an exploded, generally perspective view of the rate control plates of the rate control assembly of the invention.

FIG. 82 is a view taken along lines 82—82 of FIG. 80.

FIG. 82A is a rear view of the inlet manifold component.

FIG. 82B is a cross-sectional view taken along lines 82B—82B of FIG. 82A.

FIG. 83 is a view taken along lines 83—83 of FIG. 80.

FIG. 83A is a side elevational view of the rate control assembly shown in FIG. 77 as it appears in a sealably interconnected configuration.

FIG. 84 is a front view of the assembly shown in FIG. 83.

FIG. 84A is a cross-sectional view taken along lines 84A—84A of FIG. 84.

FIG. 85 is a rear view of the outlet manifold component of the assembly shown in FIG. 83.

FIG. 85A is a cross-sectional view taken along lines 85A—85A of FIG. 85.

FIG. 86 is a generally perspective, partially exploded view similar to FIG. 83.

FIG. 86A is a front view of the outlet manifold portion of the assembly shown in FIG. 86.

FIG. 87 is a rear view of the first from the left, rate control plate of the assembly shown in FIG. 80.

FIG. 88 is a front view of the rate control plate shown in FIG. 87.

FIG. 89 is a cross-sectional view taken along lines 89—89 of FIG. 88.

FIG. 90 is a rear view of the second from the left, rate control plate shown in FIG. 80

FIG. 91 is a front view of the rate control plate shown in FIG. 90.

FIG. 92 is a cross-sectional view taken along lines 92—92 of FIG. 91.

FIG. 93 is a fragmentary, cross-sectional view of the forward portion of the outlet manifold of the flow control means shown sealably mated with the rate control knob of the apparatus of the invention.

FIG. 93A is an enlarged, fragmentary cross-sectional view of the upper portion of FIG. 93.

FIG. 93B is an enlarged fragmentary cross-sectional view of the lower portion of FIG. 93.

FIG. 93C is an enlarged, cross-sectional view of one of the elastomeric sealing bands shown in FIG. 93A.

FIG. 93D is an enlarged, cross-sectional view of the other elastomeric sealing bands shown in FIG. 93A.

FIG. 94 is a cross-sectional view taken along lines 94—94 of FIG. 93.

Figure 94:
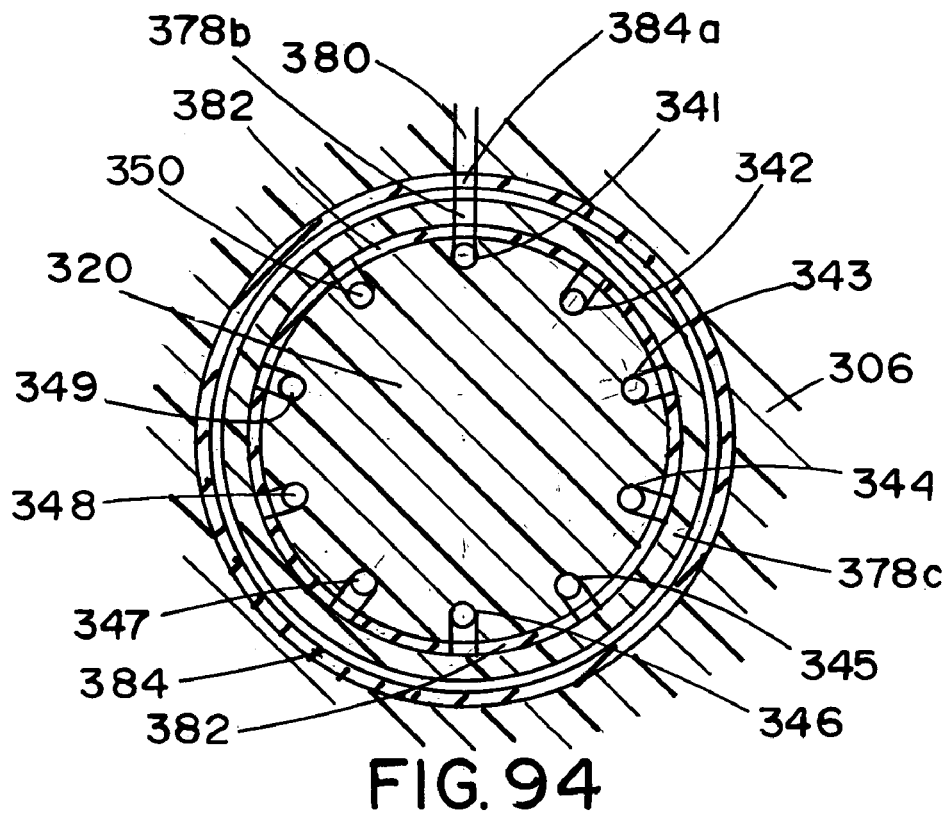
Figure 95:
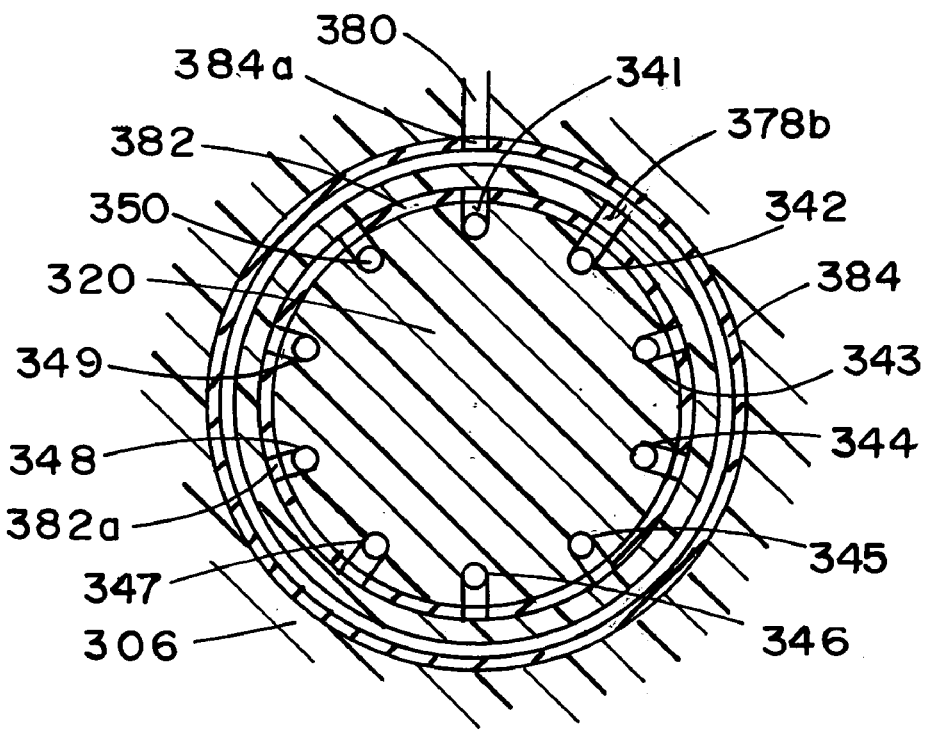

FIG. 95 is a cross-sectional view similar to FIG. 94, but showing the rate control knob rotated to second rate control position.

Figure 96:
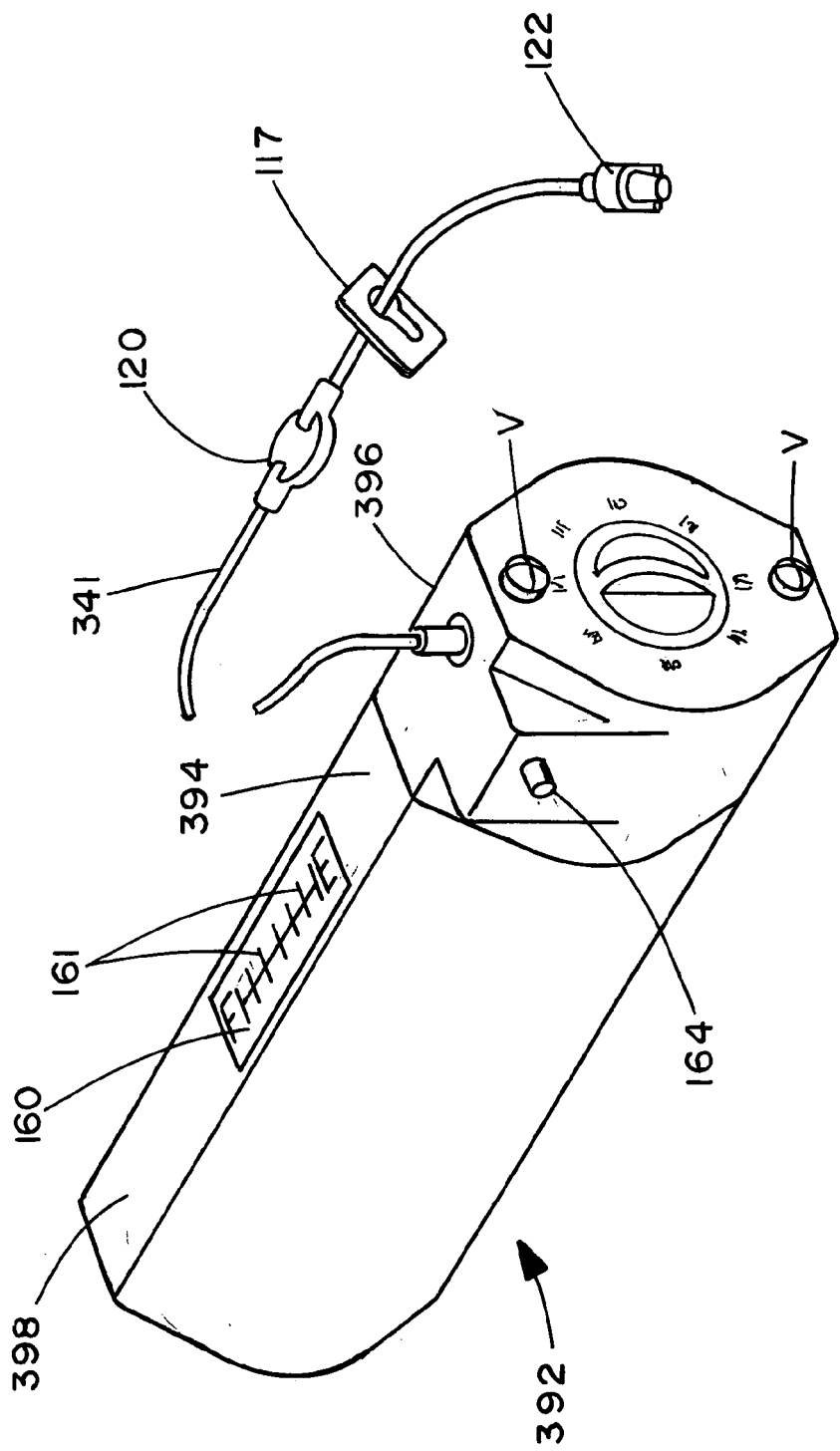

FIG. 96 is a generally perspective view of yet another embodiment of the medicament infusion apparatus of the present invention for dispensing fluids at a uniform rate.

Figure 97:
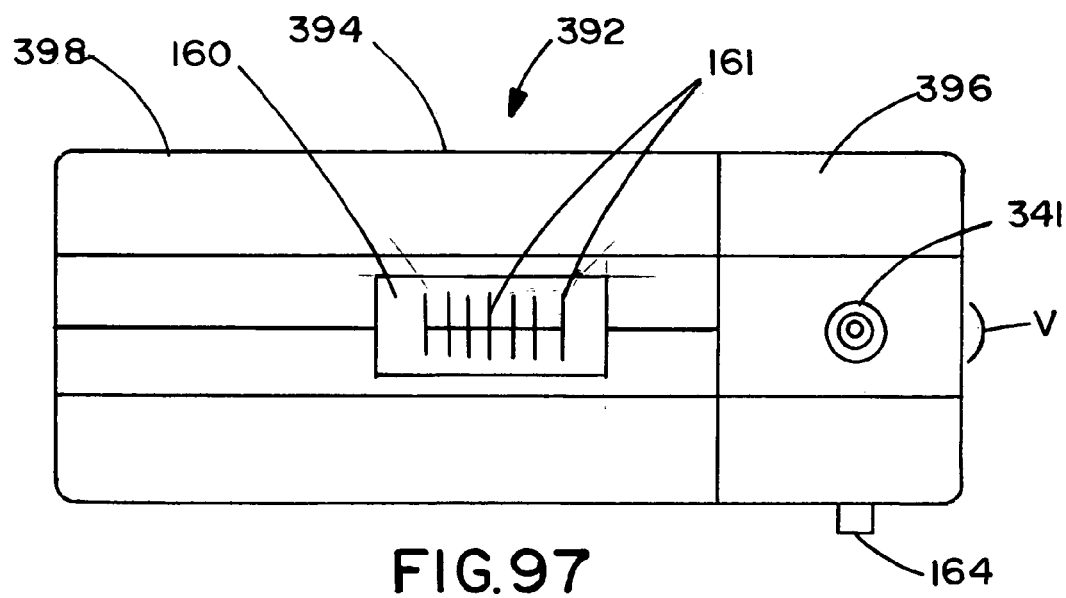

FIG. 97 is a top plan view of the embodiment of the medicament infusion apparatus shown in FIG. 96.

Figure 98:
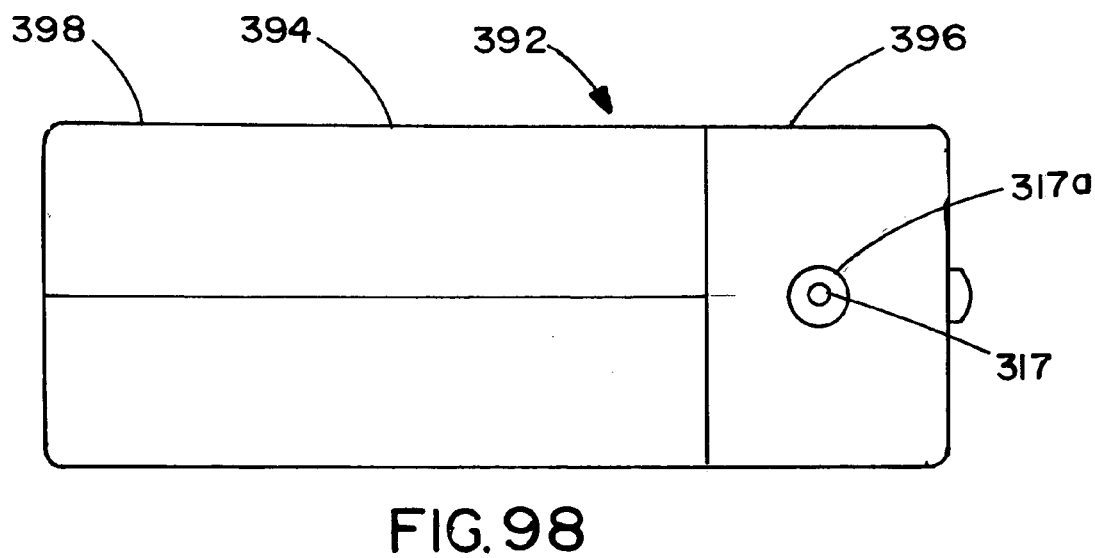

FIG. 98 is a bottom plan view of the apparatus shown in FIG. 97.

Figure 99:
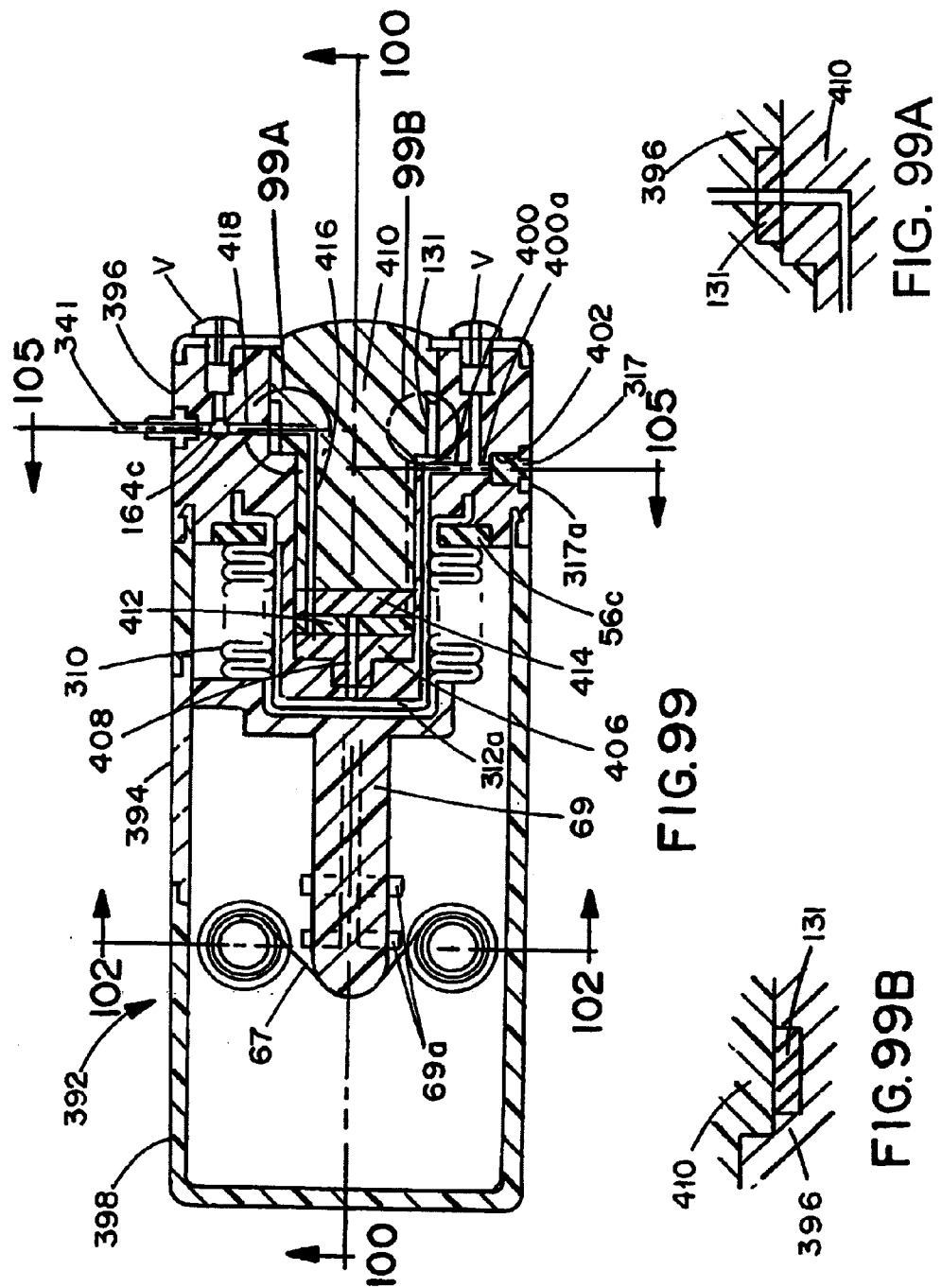

FIG. 99 is a longitudinal, cross-sectional view of the apparatus shown in FIG. 96.

FIG. 99A is an enlarged, cross-sectional view of the area designated as 99A in FIG. 99.

FIG. 99B is an enlarged, cross-sectional view of the area designated as 99B in FIG. 99.

Figure 100:
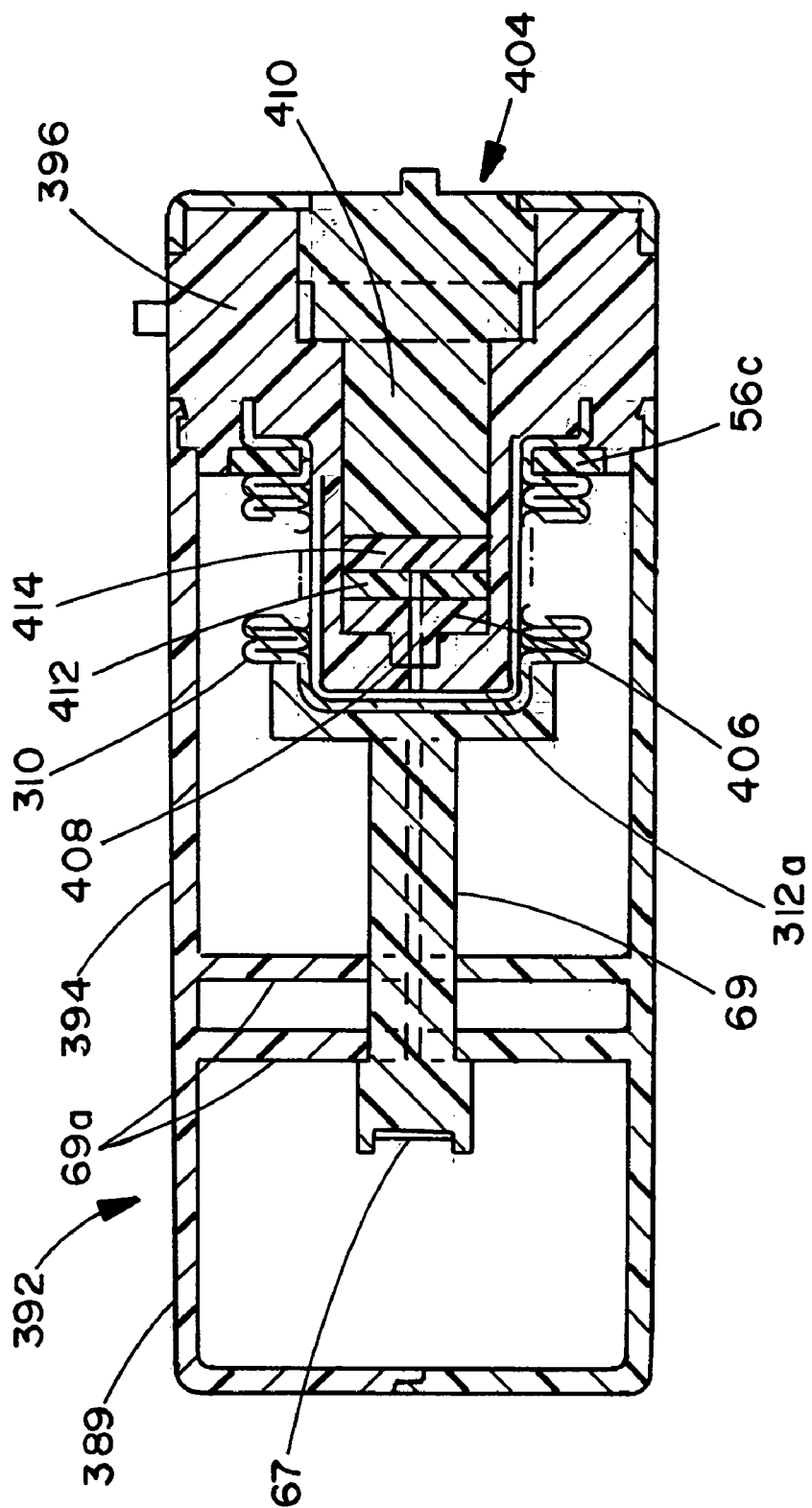

FIG. 100 is a cross-sectional view taken along lines 100—100 of FIG. 99.

FIG. 100A is a generally perspective front view of the flow control assembly of the form of the invention shown in FIG. 100.

FIG. 100B is a generally perspective rear view of the flow control assembly.

FIG. 100C is a longitudinal, cross-sectional view of the flow control assembly.

FIG. 100D is a generally perspective, exploded view of the flow control assembly.

Figure 101:
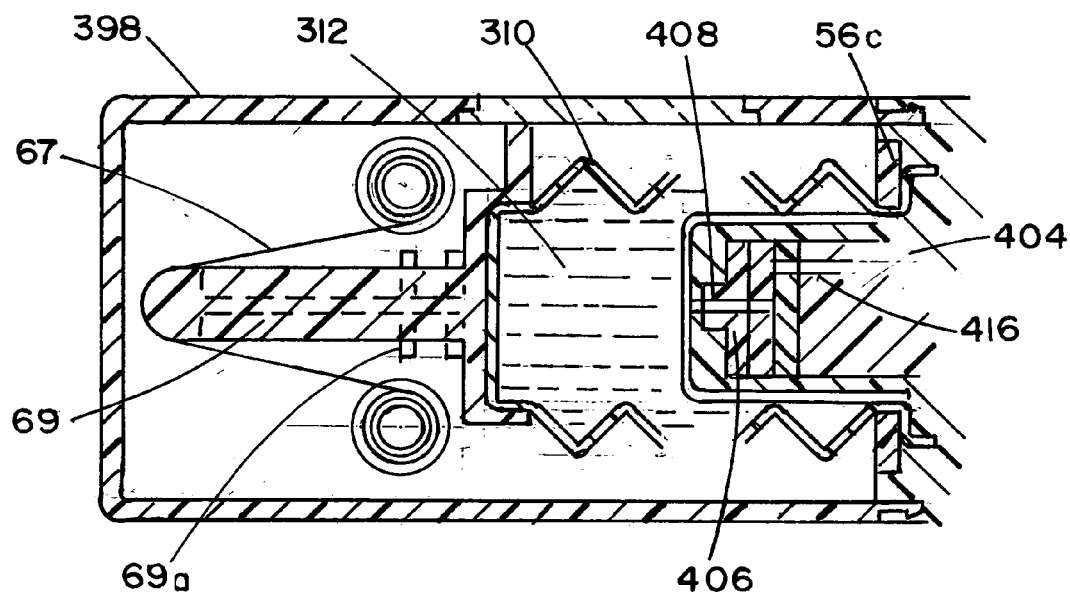

FIG. 101 is a cross-sectional view similar to FIG. 99, but showing the fluid reservoir filled with fluid.

Figures 102, 103:
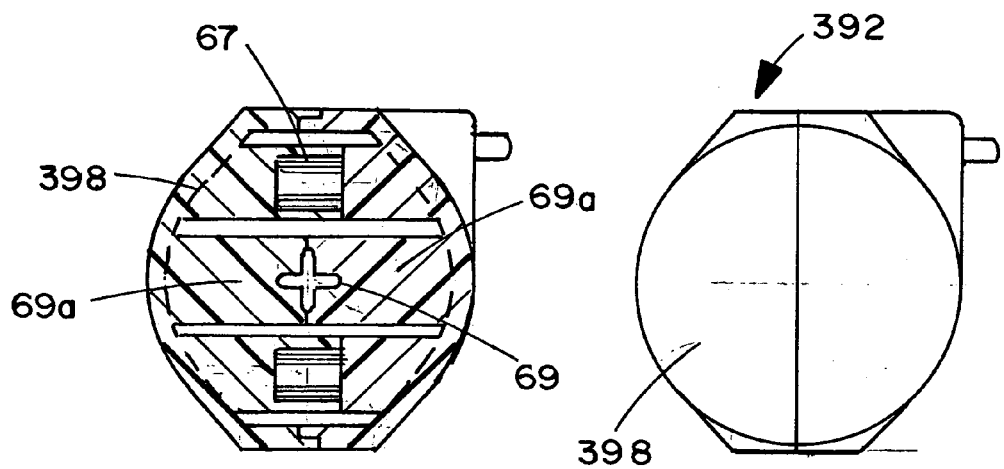

FIG. 102 is a cross-sectional view taken along lines 102—102 of FIG. 99.

FIG. 103 is a left-end view of the apparatus shown in FIG. 96.

Figure 104:
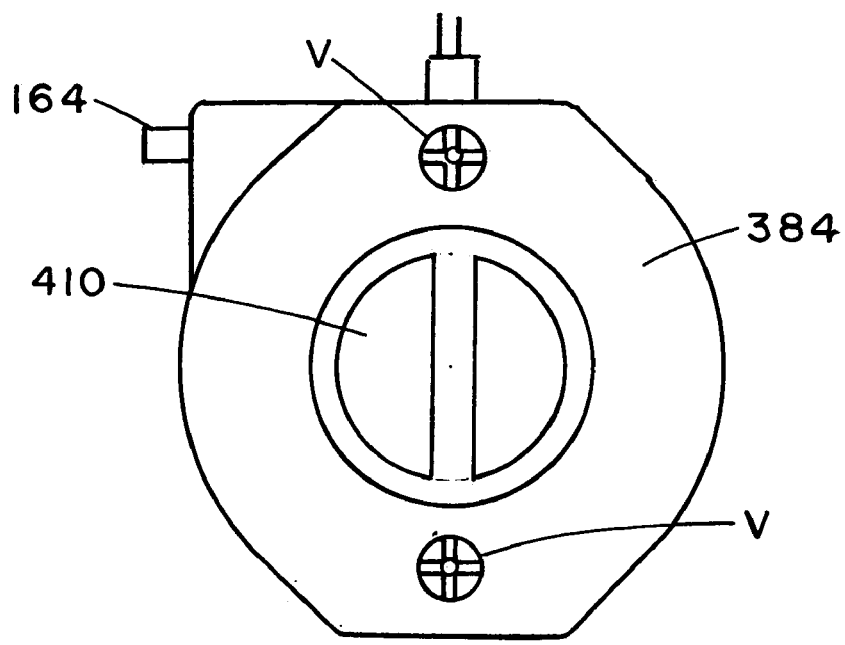

FIG. 104 is a right-end view of the apparatus shown in FIG. 96.

Figure 105:
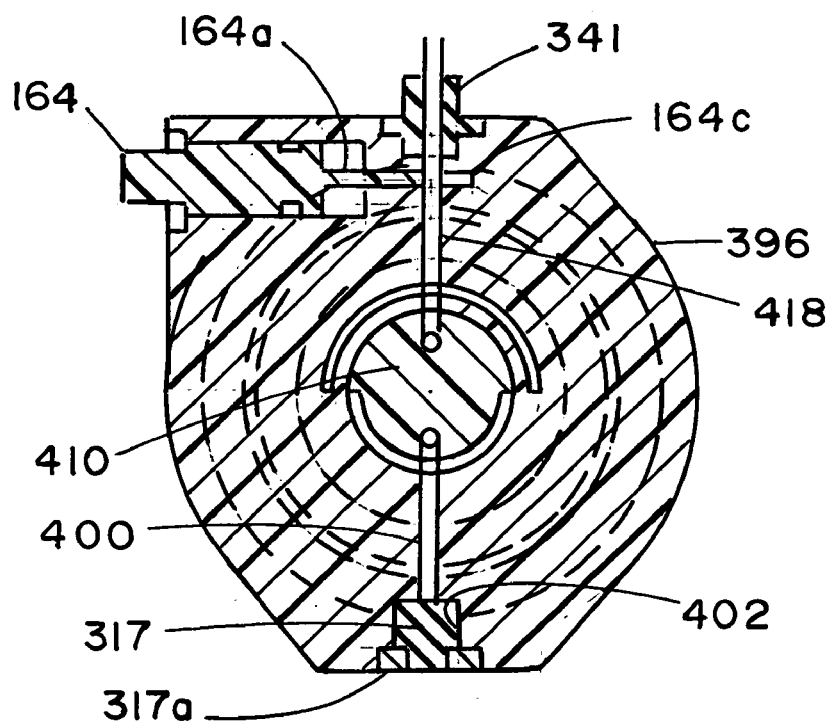

FIG. 105 is a cross-sectional view taken along lines 105—105 of FIG. 99.

Figure 106:
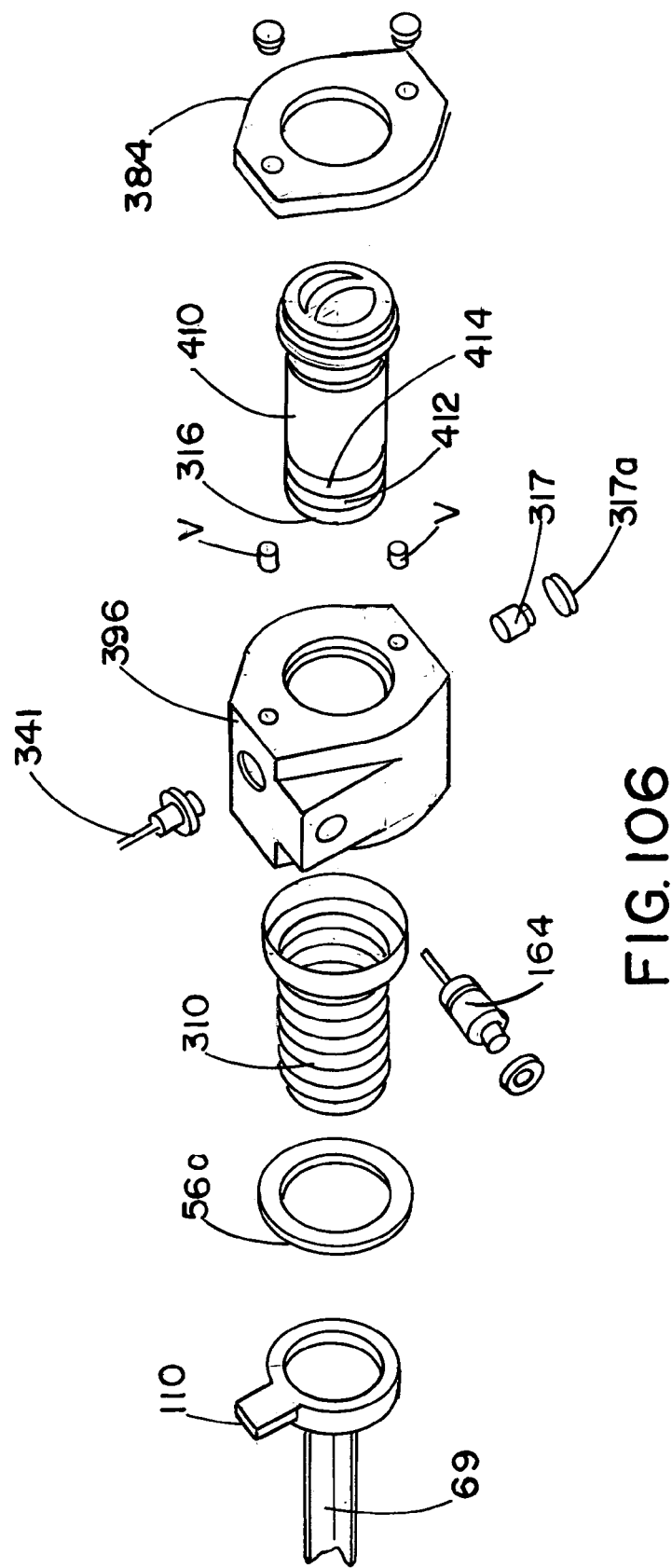

FIGS. 106 and 106B when considered together comprise a generally perspective, exploded view of the assembly shown in FIG. 99 (hereinafter collectively referred to as FIG. 106)

FIG. 106C is an end view of the snap together housing component shown in the lower left hand portion of FIG. 106B.

FIG. 106A is a view taken along lines 106A of FIG. 106.

Figure 107:
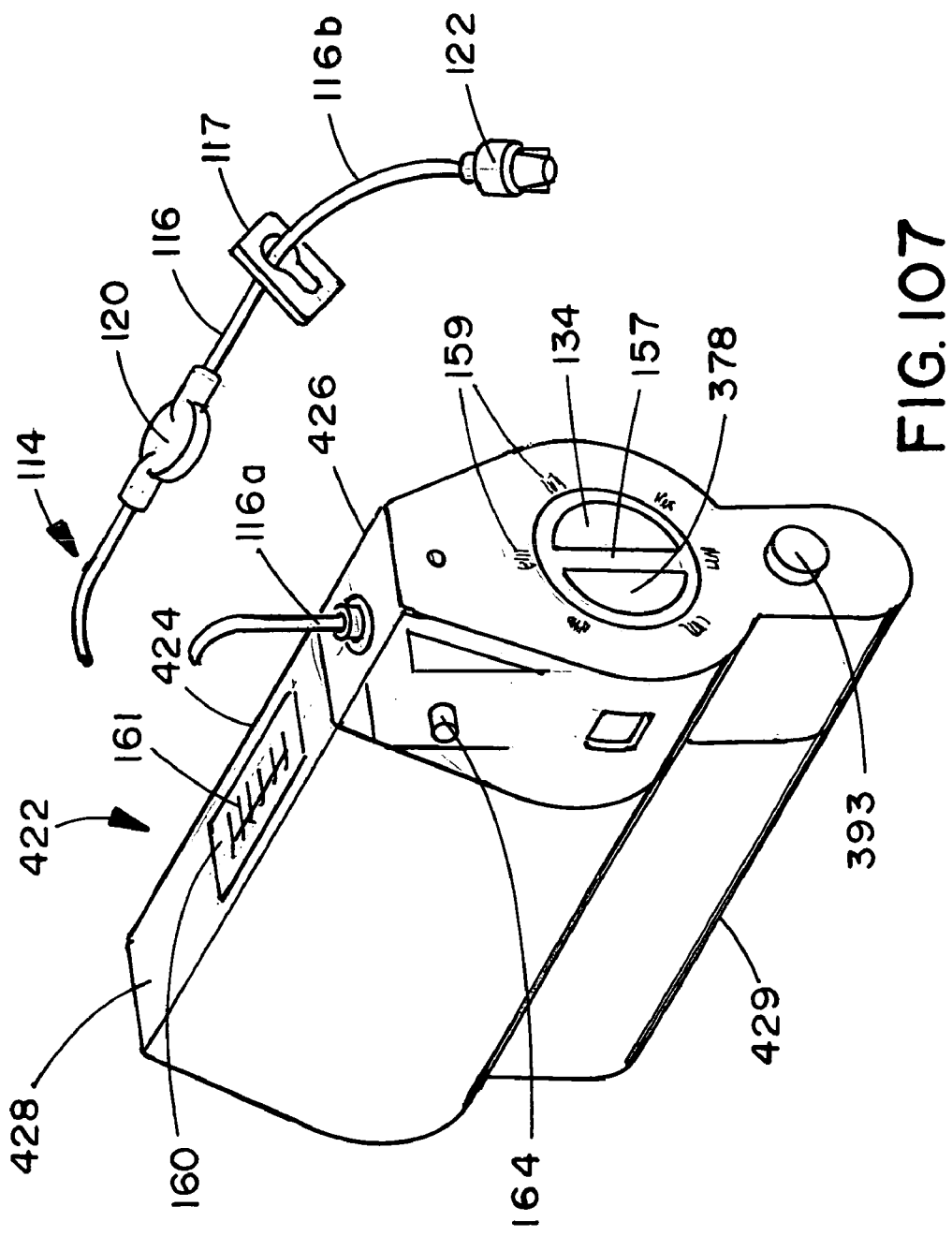

FIG. 107 is a generally perspective view of still another embodiment of the medicament infusion apparatus of the present invention for dispensing fluids at a uniform rate.

Figure 107A:
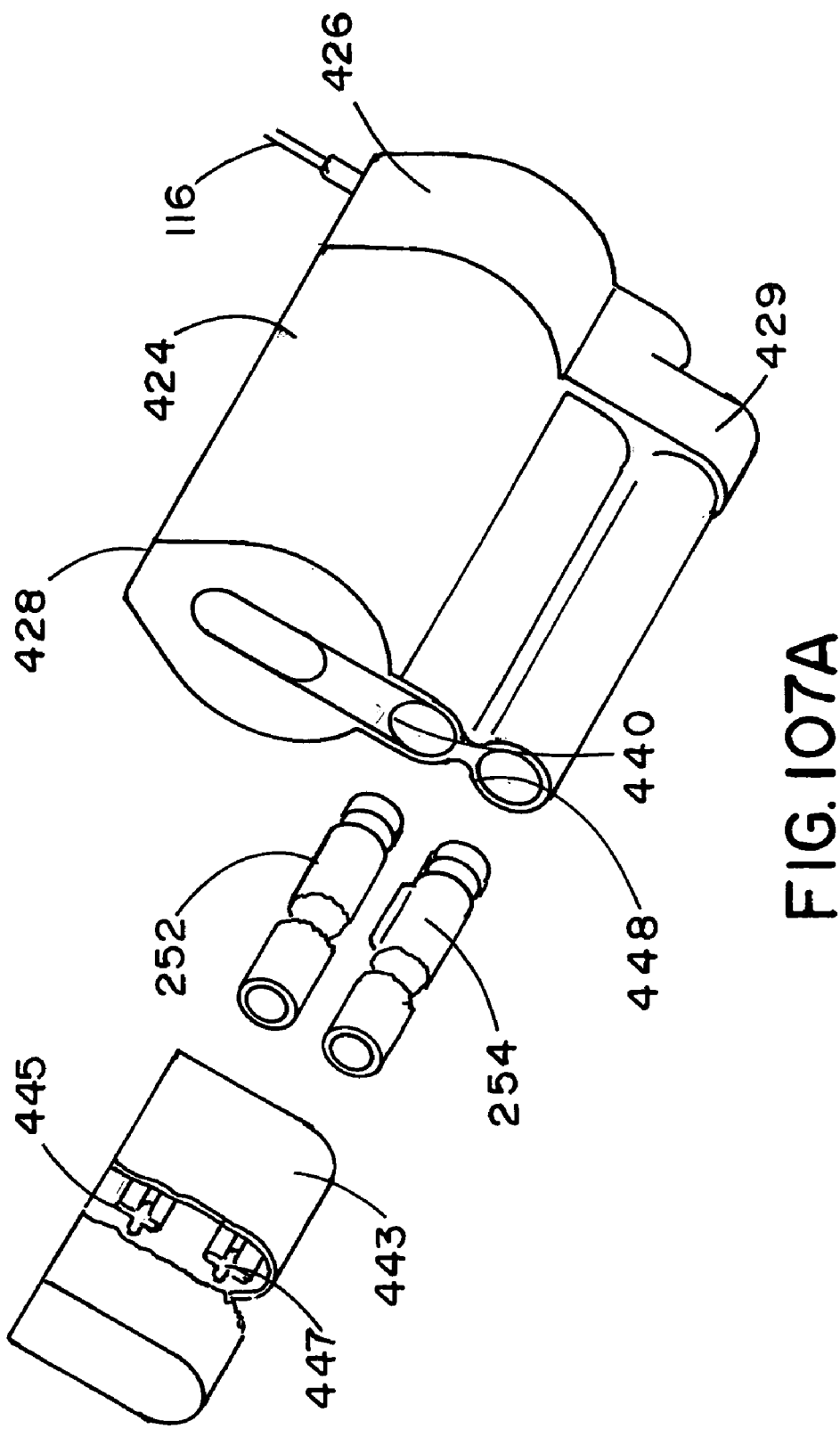

FIG. 107A is a generally perspective, exploded view of the embodiment of the apparatus shown in FIG. 107.

Figure 108:
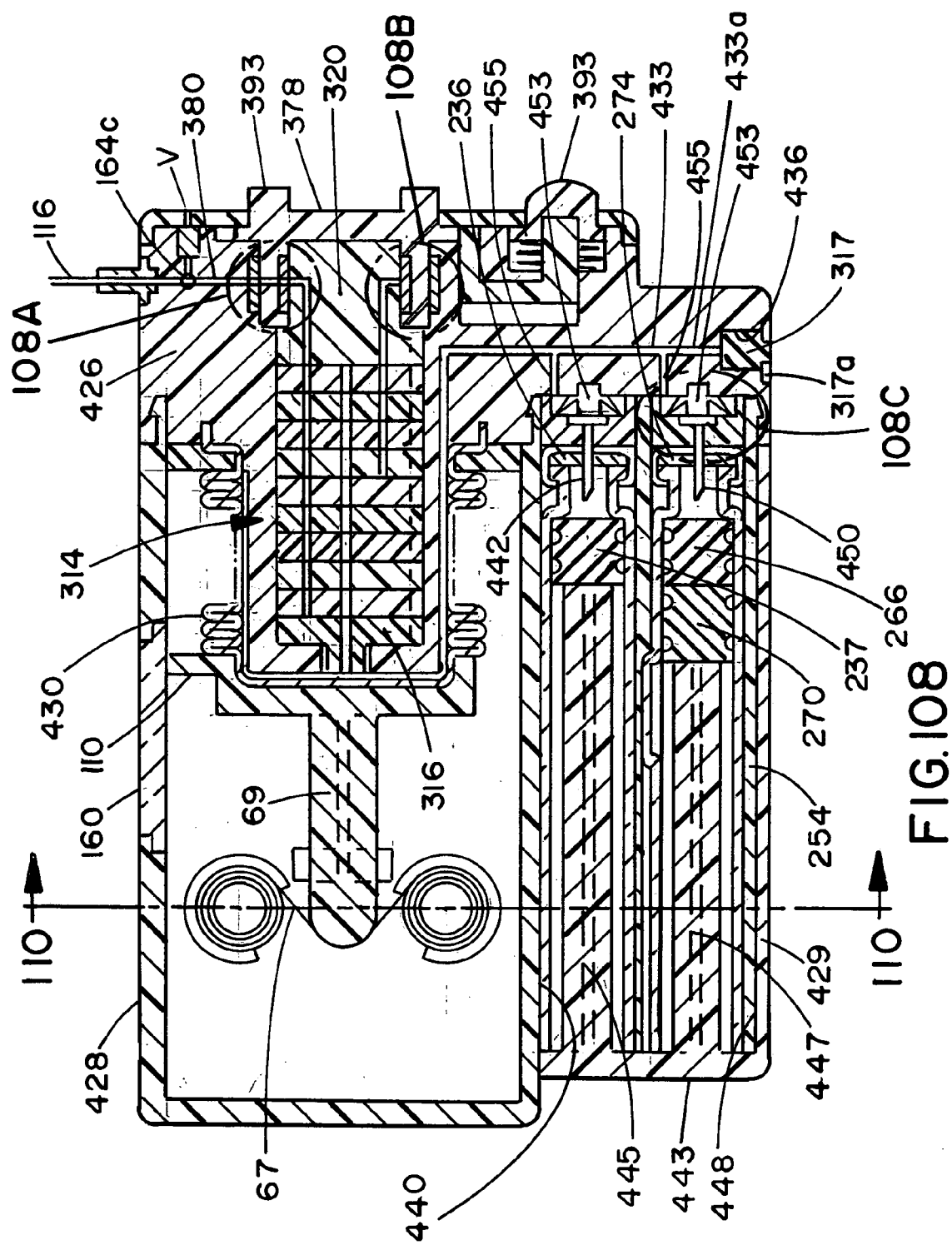

FIG. 108 is a longitudinal, cross-sectional view of the apparatus shown in FIG. 107.

Figure 108A:
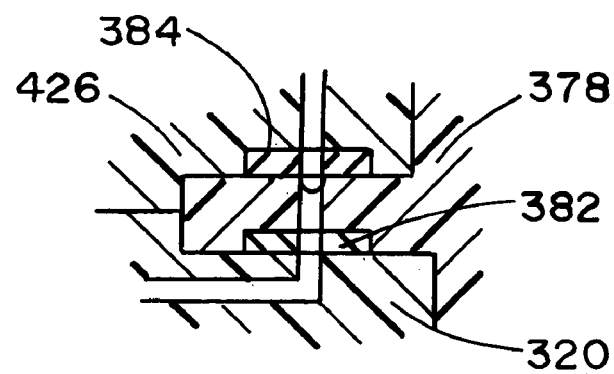

FIG. 108A is an enlarged, cross-sectional view of the area designated as 108A of FIG. 108.

Figure 108B:
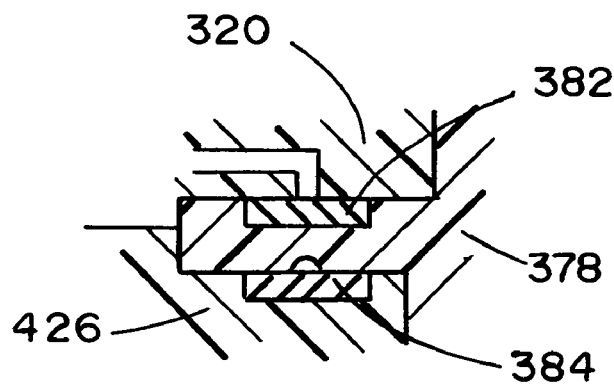

FIG. 108B is an enlarged, cross-sectional view of the area designated as 108B in FIG. 108.

Figure 108C:
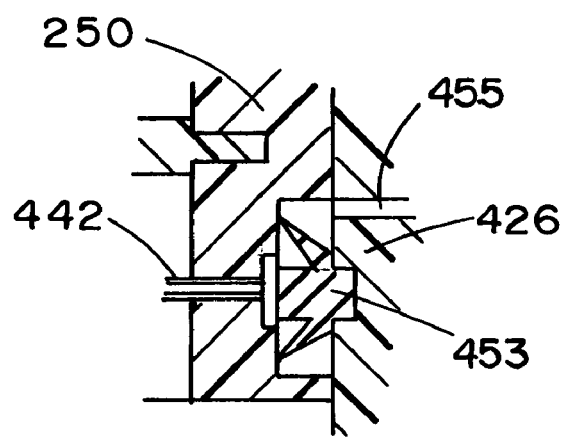

FIG. 108C is an enlarged, cross-sectional view of the area designated as 108C in FIG. 108.

FIG. 109 is a left-end view of the apparatus shown in FIG. 107.

FIG. 110 is a cross-sectional view taken along lines 110—110 of FIG. 108.

FIG. 110A is a view taken along lines 110A—110A of FIG. 110.

FIG. 111 is a side elevational view of the vial cover portion of the apparatus shown in FIG. 108.

FIG. 112 is a view taken along lines 112—112 of FIG. 111.

FIG. 113 is an enlarged, cross-sectional view of the upper fill vial of the apparatus of the invention shown in FIG. 108.

FIG. 114 is a view taken along lines 114—114 of FIG. 113.

FIG. 115 is an enlarged cross-sectional view of the lowermost cartridge fill vial of the apparatus of the invention shown in FIG. 108.

FIG. 116 is a view taken along lines 116—116 of FIG. 115.

FIG. 117 is an enlarged cross-sectional view of an alternate form of the lowermost cartridge fill vial of the apparatus of the invention shown in FIG. 108.

FIG. 118 is a view taken along lines 118—118 of FIG. 117.

DESCRIPTION OF THE INVENTION

Referring to the drawings and particularly to FIGS. 1 through 14, one embodiment of the dispensing apparatus of the present invention is there illustrated and generally designated by the numeral 52. The apparatus here comprises a snap and bond moldable plastic outer housing 54 having a first, second and third portions 54a, 54b and 54c respectively. Disposed within outer housing 54 is a first, expandable housing 56 having a fluid reservoir 58 (FIGS. 4 and 8) that is provided with an inlet passageway 60 for permitting fluid flow into the fluid reservoir and an outlet 64 for permitting fluid flow from the fluid reservoir. Expandable housing 56, which can be constructed from a metal or plastic material and can include a surface treatment and coating of the character presently to be described, comprises a bellows structure having an expandable and compressible, accordion like, annular-shaped sidewall 56a, the configuration of which is best seen in FIGS. 4 and 8.

Disposed within second portion 54b of outer housing 54 is the novel stored energy means of the invention for acting upon inner expandable housing 56 in a manner to cause the fluid contained within fluid reservoir 58 to controllably flow outwardly of the housing. In the present form of the invention, this important stored energy means comprises a constant force extension spring member 67 that is carried within cavities or wells 54a formed in the second portion 54b of the outer housing (see FIG. 14).

Figure 4:
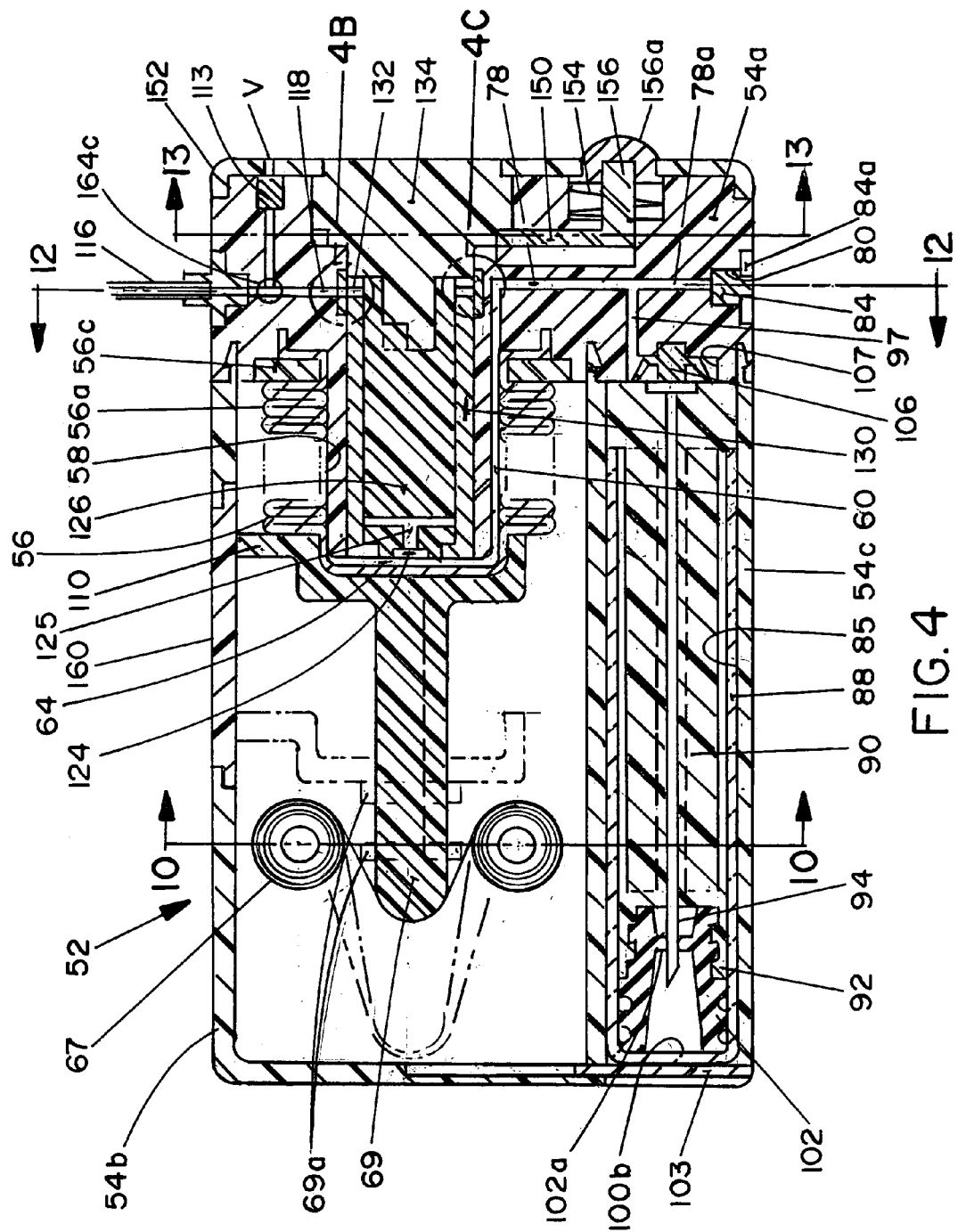
FIG. 4 is a cross-sectional view taken along lines 4—4 of FIG. 3.

Spring member 67 is first extended in the manner shown in FIG. 8 by fluid flowing into reservoir 58 and then controllably retracts in the manner shown in FIG. 4 to cause fluid flow from the outer housing through the dispensing means of the invention. Stored energy member or constant-force, double-spool, single-layer spring 67, which is a special variety of extension spring, is readily commercially available from several sources, including Barnes Group Inc. of Bristol, Conn.; Stock Drive Products/Sterling Instrument of Hyde Park, N.Y. and Walker Corporation of Ontario, Calif. Constant force extension spring 67 is basically a high stress, long deflection device that offers great advantages when used in applications, such as the present application, where very low or zero gradient is desired, where space is a factor and where very high reliability, accuracy, and forced tolerance is required. Constant force springs, such as spring 67, provides markedly superior constant force loading when compared to conventional helical extension or like conventional types of springs. A constant force spring is typically a roll of prestressed, strip of metal that exerts a nearly constant restraining force to resist uncoiling. The force is constant because the change in the radius of the curvature is constant. Spring 67 can be of a laminate construction, such a shown in FIGS. 5 and 6, and identified as 67a wherein the laminate construction acts on a pusher member 69 of the character shown in FIG. 4. Alternatively spring 67 can comprise a pair of cooperatively associated, individual extension springs 67a and 67b of the character shown in FIG. 7 which have free end portions 67c that are receivable within spring receiving slots 71 formed in a specially constructed pusher member 73. Springs 67, 67a and 67b can be constructed from a wide variety of materials including stainless steel and are held in position by opposing positioning means or cross members 67d which are of the construction shown in FIGS. 10 and 10A.

After the springs are extended in the manner shown by the phantom lines in FIG. 4 and by the solid lines in FIG. 8, the springs will inherently tend to uniformly return toward their starting configuration and in so doing will exert a substantially constant force (force over extension or extension overtime) on the pusher member 69 which is operably coupled with the expandable housing 56 in the manner shown in FIGS. 4 and 8. As the springs return to their starting configuration, the fluid contained within the fluid reservoir 58 will be caused to flow outwardly through outlet 64 at a substantially constant rate.

Forming an important aspect of the apparatus of the present invention is fill means carried by the third portion 54c of outer housing 54 for filling the reservoir 58 with the fluid to be dispensed. As best seen in FIG. 4, third portion 54c of the outer housing includes a fluid passageway 78 that is in communication with inlet 60 of fluid reservoir 58. Proximate its lower end 78a, fluid passageway 78 communicates with a cavity 80 formed within the third portion 54c of the housing. Disposed within cavity 80 is a pierceable septum 84 that comprises a part of one form of the fill means of this latest form of the invention. Septum 84, which is of conventional construction, is held in position by a retainer 84a and is pierceable by the needle of the syringe which contains the medicinal fluid to be dispensed and which can be used in a conventional manner to fill or partially fill reservoir 58 via passageway 78. Septum 84 can also be used to accomplish residual drug recovery from reservoir 58.

Third portion 54c of housing 54 also includes a chamber 85 for telescopically receiving a medicament containing shell fill vial 88. An elongated support 90, which is disposed within chamber 85, includes a threaded end portion 92 and carries a longitudinally extending, elongated hollow needle 94 having a flow passageway that communicates with fluid passageway 78 via a stub passageway 97. Chamber 85, elongated support 90 and hollow needle 94 together comprise an alternate form of fill means of the apparatus of the invention. The method of operation of this alternate form of fill means will presently be described.

Referring particularly to FIG. 8A, the medicament containing fill vial 88 includes a body portion 88a, having a fluid chamber 100 for containing the injectable fluid medicament "F". Chamber 100 is provided with a first open end 100a and second closed end 100b. First open end 100a is sealably closed by closure means here provided in the form of an externally threaded elastomeric plunger 102, which is telescopically movable within the vial from a first location, where the plunger is disposed proximate first open end 100a to a second, device-fill location where the plunger is disposed proximate second closed end 100b.

After removal of the vial chamber cover 103, which forms a part of the third portion 54c of the snap and bond together housing 52 (FIGS. 4 and 14), vial 88 can be inserted into chamber 85. As the fill vial is so introduced and the plunger 102 is threadably interconnected with end 92 of support 90 (FIG. 4), the sharp end of the elongated needle 94 will pierce the central wall 102a of the elastomeric plunger. Continuous pushing movement of the vial into chamber 85 will cause the structural support 90 to move the elastomeric plunger inwardly of the vial chamber 100 in a direction toward the second, or closed end 100b of the vial chamber. As the plunger is moved inwardly of the vial, the fluid "F" contained within the vial chamber will be expelled there from into the hollow elongated needle 94. As best seen in FIG. 4, the fluid will then flow past a conventional elastomeric umbrella type check valve 106, which is mounted within a cavity 107 formed in lower portion 54c of the outer housing. Next, the fluid will flow into stub passageway 97 and thence into passageway 78. Umbrella type check valve 106 functions in a conventional manner to control fluid flow from the elongated hollow needle 94 toward fluid passageway 78. From passageway 78, the fluid will flow into inlet passageway 60 and then into reservoir 58 of the bellows component 56.

As the fluid flows from either of the fill means of the invention into the bellows reservoir 58, the bellows will expand from the collapsed configuration shown in FIG. 4 into the expanded configuration shown in FIG. 8. As best seen in FIG. 4A, the inner wall of the bellows is provided with one or more protective coatings "C" that is compatible with the fluids contained within reservoir 58. This coating can be accomplished by several different processes. One process that is extremely clean, fast and effective is plasma processing. In particular this technique allows for any of the following: plasma activation, plasma induced grafting and plasma polymerization of molecular entities on the surface of the bellows. For cases where an inert hydrophobic interface is desired, plasma using fluorine-containing molecules may be employed. In this regard, the bellows surface may be cleaned with an inert gas plasma, and subsequently, a fluorine containing plasma may be used to graft these molecules to the surface. Alternatively, if a hydrophilic surface is desired (e.g. for drug solutions that are highly corrosive or in oil based solvents) an initial plasma cleaning may be done, followed by a plasma polymerization using hydrophilic monomers.

As the bellows member expands it will urge a telescopically movable volume indicator member 110, which is carried within a second portion 54b of the housing and which is interconnected with pusher member 69, rearwardly of the apparatus housing in the manner shown in FIG. 8. Pusher member 69 is stabilized by controller struts 69a which are located on the housing of body half shells 54c. The forces thus exerted on the spring member 67 by the rearwardly moving pusher member 69 will cause the spring member 67 to expand from its retracted configuration shown in FIG. 4 into the expanded configuration shown in FIG. 8. As the reservoir 58 fills with fluid, any gases trapped within the reservoir will be vented to atmosphere via vent means "V" mounted in portion 54a of the housing. This vent means here comprises a gas vent 113 (FIG. 8) that can be constructed of a suitable hydrophobic porous material such as a porous plastic.

Upon opening the fluid delivery path to the fluid delivery means of the invention, shown here as a conventional administration set 114 (FIG. 1), the stored energy means, or spring 67, will tend to return to its starting configuration thereby controllably urging fluid flow outwardly of reservoir 58 via the flow control means of the invention the character of which will presently be described.

Figure 1:
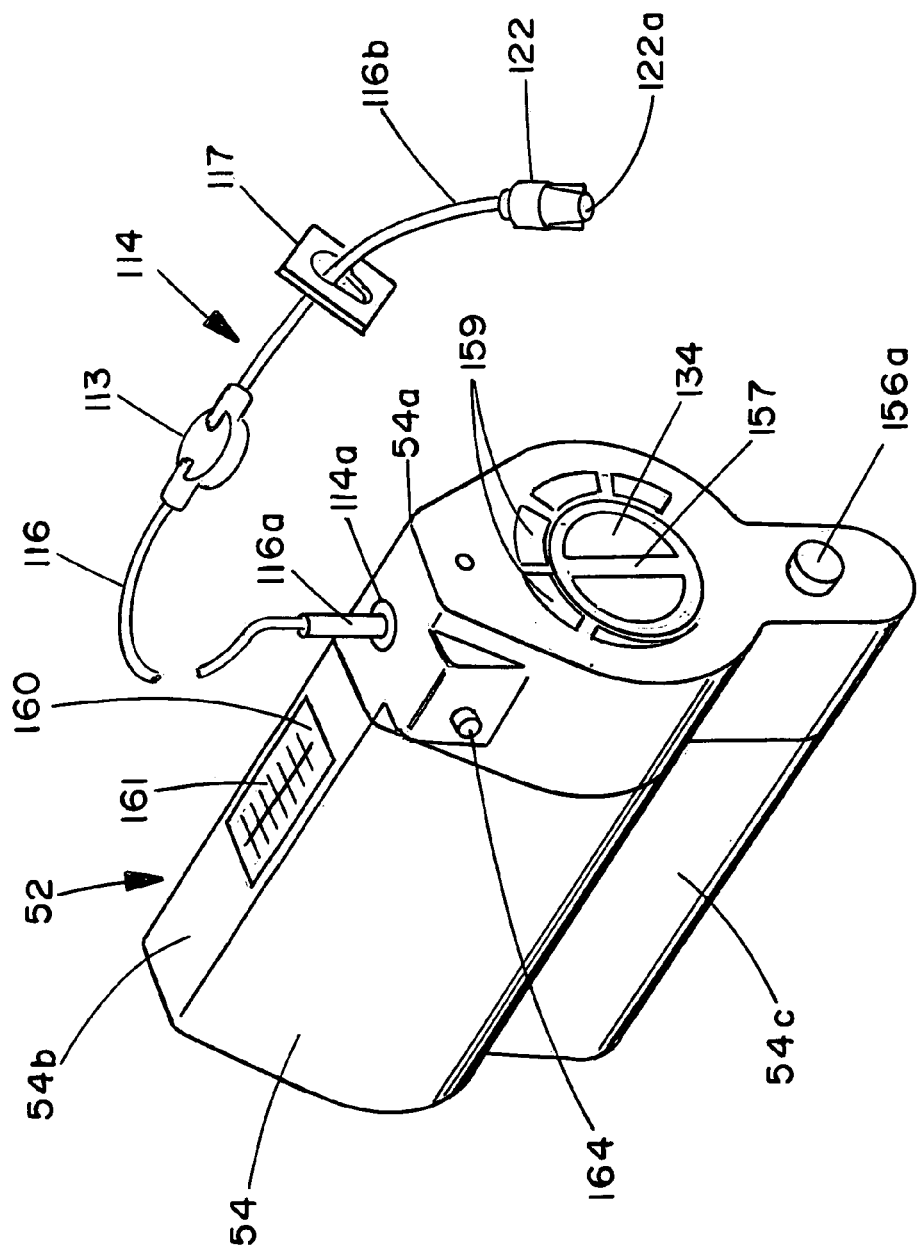
FIG. 1 is a generally perspective view of one embodiment of the medicament infusion apparatus of the present invention for dispensing fluids at a uniform rate.

Administration set 114 is sealably connected to the first portion 54a of housing 54 by a connector 114a in the manner shown in FIG. 1 of the drawings. As illustrated in FIGS. 1 and 4, the proximal end 116a of administration line 116 of the administration set is in communication with an outlet fluid passageway 118 which is formed in portion 54a of the outer housing. Disposed between the proximal end 116a and the distal end 116b of the administration line are a conventional clamp 117, a conventional gas vent and a conventional filter 113. Provided at the distal end 116b of the administration line is a luer connector 122 and luer cap 122a of conventional construction (FIG. 1).

A number of beneficial agents can be contained within shell vial 88 and can be controllably dispensed from the fluid dispenser to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As the fluid contained within the bellows reservoir 58 is urged outwardly thereof by the stored energy means, the fluid will flow under pressure through a filter means, shown here as a filter 124 that is carried in a cavity provided in a generally cylindrically shaped flow rate control member 126 (FIG. 19). Flow rate control member 126 forms a part of the flow control means, or flow control assembly 129 of the invention. As will be better understood from the discussion which follows, this important flow control means functions to precisely control the rate of fluid flow outwardly from reservoir 58 and toward the patient via the administration set.

Peripherally bonded filter 124, which functions to filter particulate matter from the fluid flowing outwardly from reservoir 58 is of a character well known to those skilled in the art and can be constructed from various readily available materials such as polysolfone and polypropylene wafers having a desired porosity. After flowing through filter 124, the fluid will flow, via a stub passageway 125 (FIG. 4) into the fluid flow distribution means of flow rate control member 126, which functions, in a manner presently to be described, to distribute the fluid into the flow control channels strategically formed in member 126.

Referring particularly to FIGS. 15 through 26, it can be seen that flow control assembly 129 comprises an outer casing 130 having a plurality of circumferentially spaced apart fluid outlets 132, a flow rate control member 126, which is telescopically receivable within casing 130 and a selector knob 134 that is interconnected with rate control member 126 in the manner best seen in FIGS. 15, 16, 18, 19 and 23. A compressibly deformable elastomeric band 131 sealably interconnects casing 130 with the housing portion 54a in the manner shown in FIGS. 4B and 4C. As illustrated in the drawings, flow rate control member 126 is uniquely provided with a plurality of elongated flow control channels 128, each having an inlet 128b and an outlet 128a. The flow channels 128 may be of different sizes, lengths, depths, widths and configurations as shown by FIGS. 20 and 21, which depict alternate forms of the flow control member. These alternate forms of flow control members with alternate microchannel configurations, which are identified in the drawings as 126a and 126b, have uniquely configured flow control channels 128c. As used herein, the term "micro channel" is interchangeable with the term "minichannel". As illustrated in FIG. 17, the flow control channels may be rectangular in cross-section. Alternatively, the flow control channels can be semicircular in cross-section, U-shaped in cross-section, or they may have any other crosssectional configuration that may be appropriate to achieve the desired fluid flow characteristics. As previously discussed, where appropriate, channels 128 can be coated with one or more special coating "C" with appropriate surface modification in the manner shown in FIG. 17.

When the flow control member is properly positioned and appropriately registered within outer casing 130, the inner surface of the outer casing wall sealably cooperates with the flow control member channels 128 to form a plurality of generally spiral shaped fluid flow passageways of different overall lengths and flow capacities. When the flow control member is positioned within the outer casing, a notch 138 formed in member 126 receives a tongue 140 provided on casing 130 so precisely align the outlets 128a of the flow channels 128 with fluid outlets 132 formed in casing 130.

Figure 14:
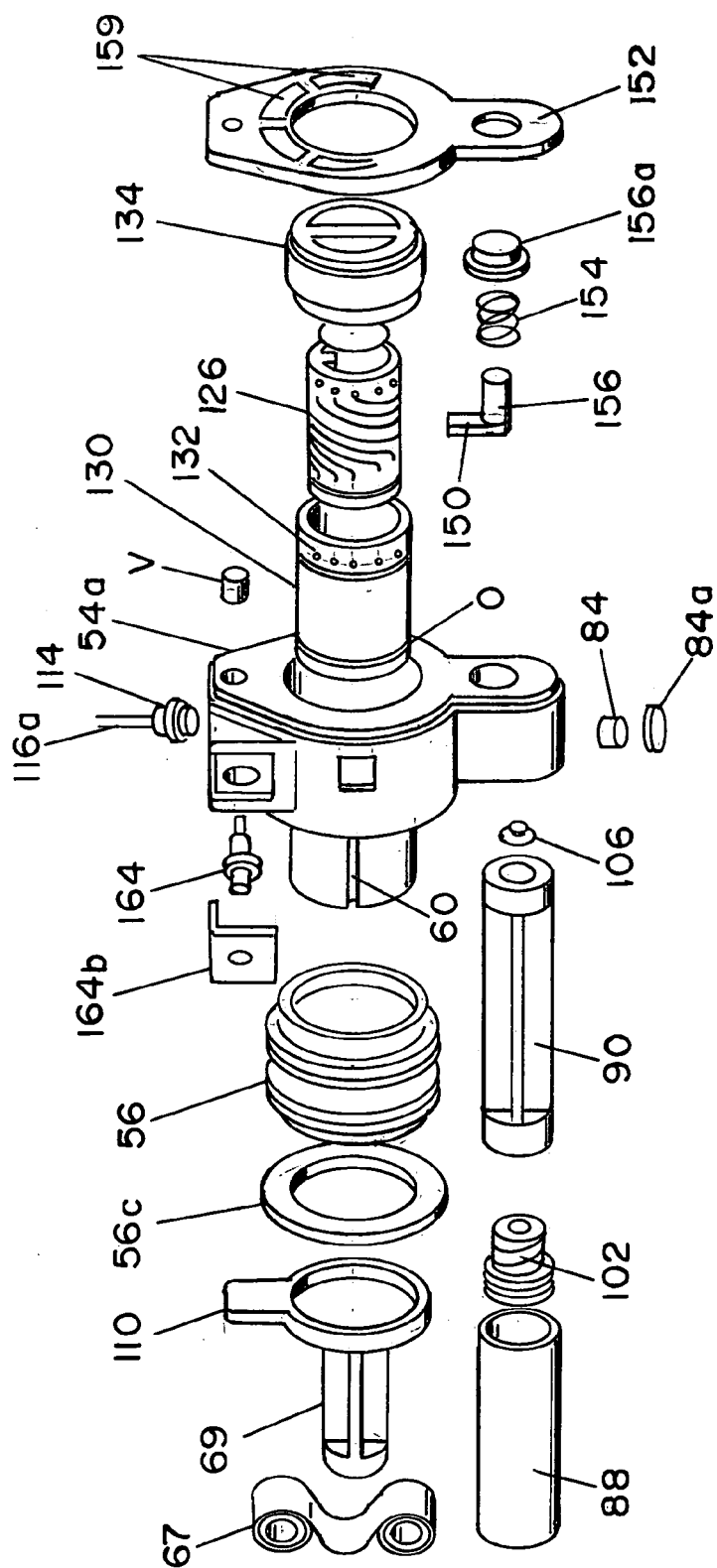
FIGS. 14A, and 14B when considered together comprise a generally perspective, exploded view of the assembly shown in FIG. 4. (hereinafter collectively referred to as FIG. 14)
FIG. 14C is a view taken along lines 14C—14C of FIG. 14B.

Selector knob 134, which comprises a part of the selector means of the invention, is rotatably connected to portion 54a of the outer housing and, in a manner presently to be described, functions to rotate the assemblage made up of outer casing 130 and flow control member 126 (FIGS. 4 and 14). In this way, a selected outlet 132 in casing 130 can be selectively aligned with flow passageway 118 provided in portion 54a (FIG. 4).

As previously discussed herein, as the fluid contained within the bellows reservoir 58 is urged outwardly thereof by the stored energy means, the fluid will flow under pressure through filter 124, into stub passageway 125 and then into the distribution means of the invention which functions to distribute fluid from the fluid reservoir to each of the plurality of spiral passageways 128 via passageway 142. This distribution means here comprises several radially outwardly extending flow passageways 142 formed in flow control member 126 (FIG. 25). The filtered fluid will fill passageways 142 and then will flow into the plurality of spiral passageways 128 formed in member 126 via outlets 128b, which communicate with passageways 142 (see FIG. 25). The fluid contained within spiral passageways 128 can flow outwardly of the device only when one of the fluid outlets 132 formed in casing 130 is aligned with reservoir outlet passageway 118 (FIGS. 8, 18 and 20).

Selection of the passageway from which the fluid is to be dispensed is accomplished by rotation of the selector knob 134 which, as best seen in FIG. 19 includes a reduced diameter portion 134a having a slot 134b formed therein. As illustrated in FIGS. 16 and 19, slot 134b is adapted to receive a spline 146 formed anteriorly of member 126. With this construction, rotation of selector knob 134 will impart part rotation to member 126. As seen in FIG. 19, inwardly extending spline segment 140 is received within slot 138 formed in member 126. Accordingly, rotation of member 126 will also impart concomitant rotation to casing member 130.

As shown in FIGS. 18 and 19, selector knob 134 is provided with a plurality of circumferentially spaced apart indexing cavities 147 that closely receive an indexing finger 150, which forms a part of the indexing means of the invention, which means comprises a front bezel 152 that is connected to the apparatus housing (see FIGS. 4 and 14). Indexing finger 150 is continuously urged into engagement with a selected one of the indexing cavities 147 by a coil spring 154 that also forms a part of the indexing means of the invention. Coil spring 154 can be compressed by an inward force exerted on an indexing shaft 156 and button 156a that is mounted in locking shaft cover 152 and is movable from an extended position to an inward, finger release position wherein spring 154 is compressed and finger 150 is retracted from a selected indexing cavity 147. With finger 150 in its retracted position, it is apparent that control knob 134 can be freely rotated to a position wherein a gripping member 157 can be aligned with selected flow rate indicia 159 formed on the front bezel 152 of the apparatus housing. The indicia may be symbols as shown in FIG. 1 or it may be numbers as shown in FIG. 11.

When the selector knob is in the desired position and pressure is released on indexing button 156a, spring 154 will urge finger 150 of the indexing means of the invention into locking engagement with one of the indexing cavities 147 thereby placing a selected one of the spiral shaped flow control channels 128 that corresponds with the indicia 159 in communication with the fluid reservoir 58 via passageways 125 and 124. As the fluid flows outwardly of the apparatus due to the urging of the stored energy means or spring member 67, the bellows structure 56 will be collapsed and at the same time pusher member 69 will travel inwardly of the housing. Member 69, which forms a part of the volume indicator means of the invention is guided by integral internal wall structure 69a of portion 54c and includes a radially outwardly extending indicating finger 110 that is visible through a volume indicator window 160 that is provided in a second portion 54b of the apparatus housing and also comprises a part of the volume indicator means of the invention (FIGS. 1, 2, 10 and 14). Indicia 161, which are provided on indicator window 160 (FIGS. 2 and 14), function to readily indicate to the caregiver the amount of fluid remaining within fluid reservoir 58 at any point in time.

Referring to FIGS. 11 and 12, disabling means, shown here as a disabling shaft 164 that is telescopically movable within a passageway 166 formed within housing portion 54a functions to irrevocably disable the device and render it inert. More particularly, shaft 164 has a distal end 164a, which, upon insertion of the shaft distal end 164a into bore 164c (FIG. 12), will block fluid flow through passageway 118. A friction fit retainer 164b normally holds shaft 164 in the retracted position (FIGS. 12 and 14). As shown in FIG. 8, a receptacle bore 164c is provided for receipt of shaft 164.

Referring now to FIGS. 27 through 37, another embodiment of the dispensing apparatus of the present invention is there illustrated and generally designated by the numeral 172. This alternate form of the apparatus of the invention is similar in many respects to that shown in FIGS. 1 through 26 and like numerals are used in FIGS. 27 through 37 to identify like components. The primary differences between this latest form of the invention and that shown in FIGS. 1 through 26 concern the provision of a differently configured internal housing and the provision of a different reservoir fill means for filling the device reservoir. More particularly, as will presently be described in greater detail, this alternate form of fill means comprises two specially designed fill vials or containers.

Figure 27:
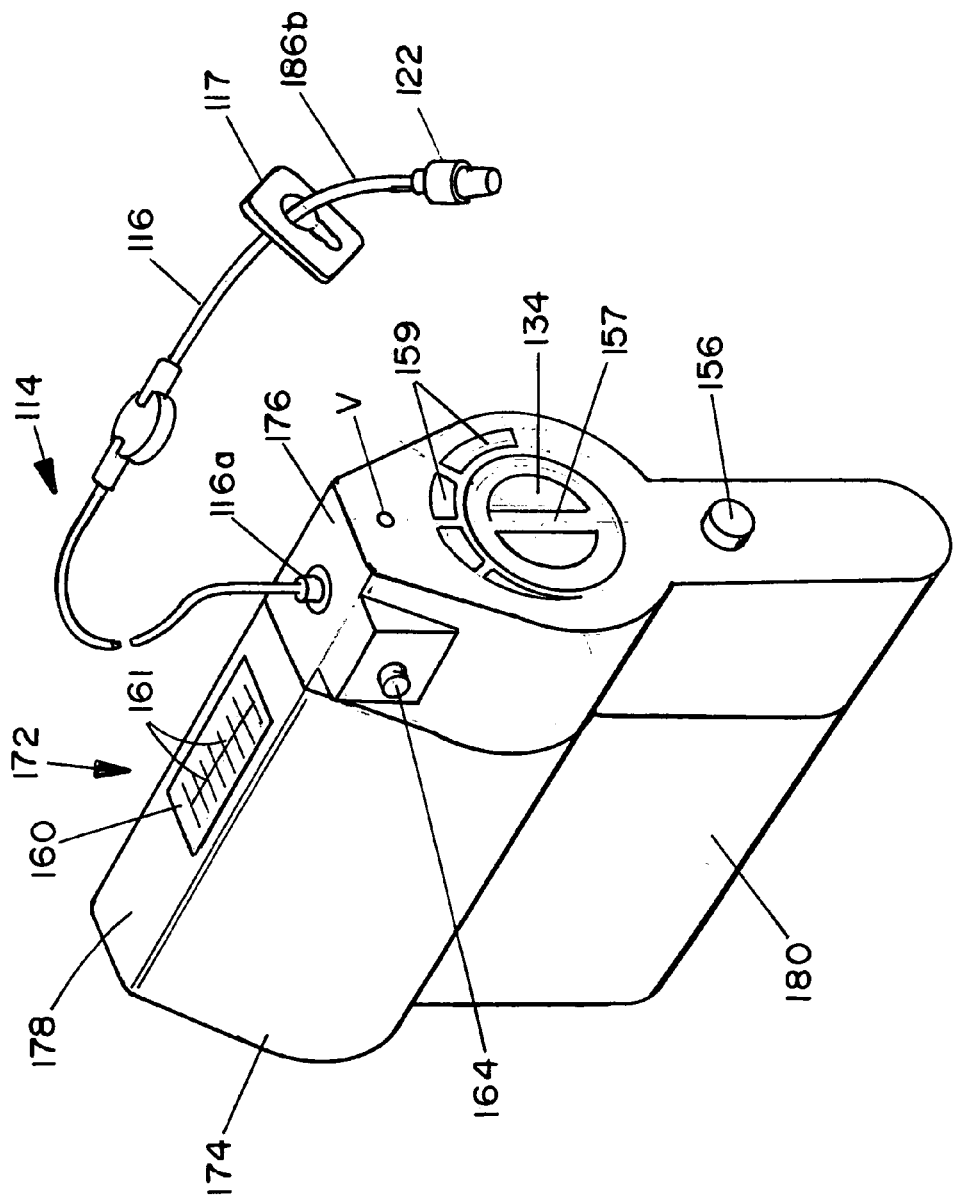
FIG. 27 is a generally perspective view of an alternate embodiment of the medicament infusion apparatus of the present invention for dispensing fluids at a uniform rate.

As best seen in FIG. 27, the apparatus here comprises an outer housing 174 having a first, second and third portions 176, 178 and 180 respectively. Disposed within outer housing 174 is an inner, expandable housing 56 which is identical in construction and operation to that described in connection with the embodiment of FIGS. 1 through 26.

Disposed within second portion 178 of outer housing 174 is the novel stored energy means of the invention for acting upon inner expandable housing 56 in a manner to cause the fluid contained within fluid reservoir 58 thereof to controllably flow outwardly of the housing. In this latest form of the invention, this stored energy means is also identical in construction and operation to that previously described and comprises a constant force spring 67.

With regard to the fill means of this latest form of the invention, which is carried by the third portion 180 of the outer housing, this important fill means once again functions to fill the reservoir 58 with the fluid to be dispensed. This fill means here comprises the previously described septum fill and recovery means, which is identical to that previously described, and also includes a vial fill means which includes two, rather than the one, shell fill vials or fill containers.

Figure 30:
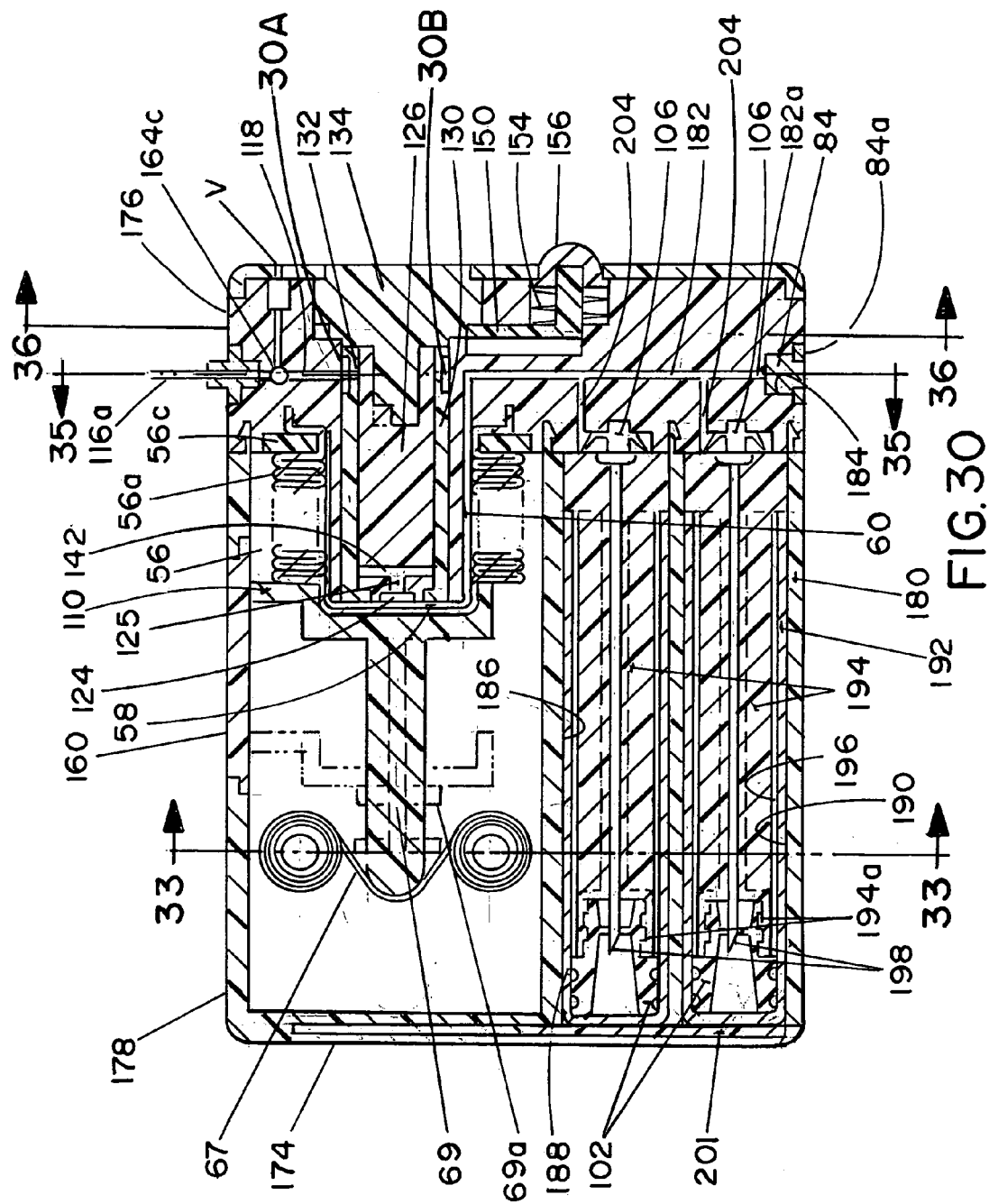
FIG. 30 is a cross-sectional view taken along lines 30—30 of FIG. 29.
Figure 30B:
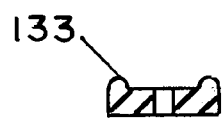
FIG. 30B is an enlarged, cross-sectional view of the elastomeric seal shown in FIG. 30.
Figure 30A:
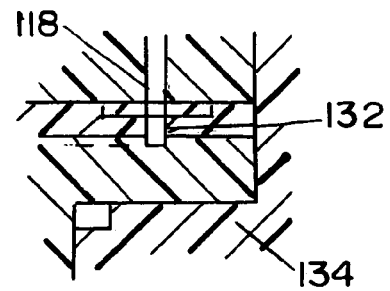
FIG. 30A is an enlarged, cross-sectional view of the area designated as 30A in FIG. 30.
Figure 35:
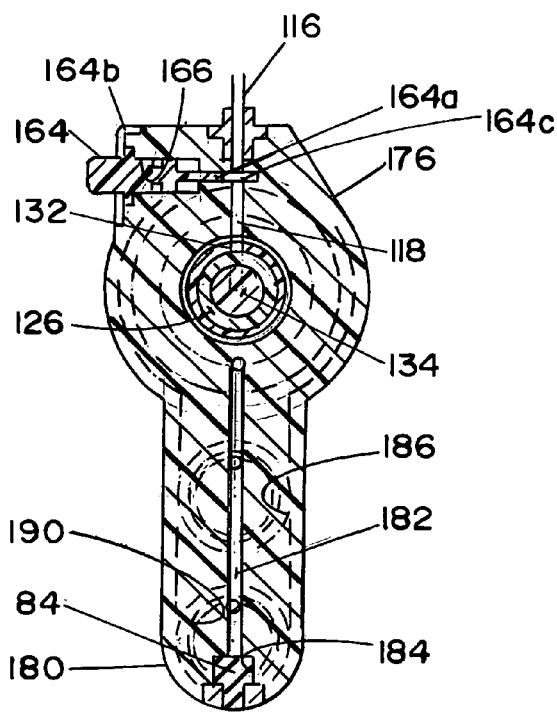
FIG. 35 is a cross-sectional view taken along lines 35—35 of FIG. 30.
Figure 36:
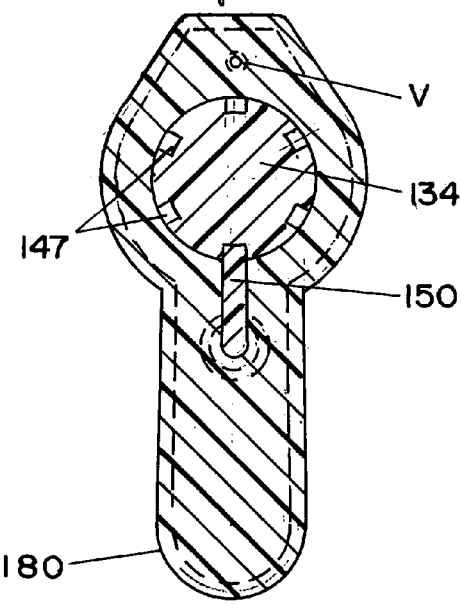
FIG. 36 is a cross-sectional view taken along lines 36—36 of FIG. 30.

With respect to the septum fill means, as illustrated in FIGS. 30 and 35, third portion 180 of the outer housing here includes a fluid passageway 182 which is in communication with inlet 60 of fluid reservoir 58. Proximate its lower end 182a, fluid passageway 182 communicates with a cavity 184 formed within the third portion 180 of the housing. Disposed within cavity 184 is a pierceable septum 84 that comprises a part of the septum fill means of this latest form of the invention. As before, septum 84, which can be a slit septum, is held in position by a retainer 84a and is pierceable by the cannula of the syringe which contains the medicinal fluid to be dispensed and which can be used in a conventional manner to fill or partially fill reservoir 58 via passageway 182.

As best seen in FIG. 30, third portion 180 of the housing also includes a first chamber 186 for telescopically receiving a first medicament containing fill vial 188 and a second chamber 190 for telescopically receiving a second medicament containing vial 192. Fill vials 188 and 192, which are of identical construction, each cooperates with an elongated support 194 that is disposed within fluid chambers 196 of the vials. Each of the elongated supports has an integrally threaded end portion 194a and carries a longitudinally extending, elongated hollow needle 198. Each of the hollow needles 198 has a flow passageway that communicates with fluid passageway 182 via the umbrella check valves and stub passageway 204. First chamber 186, second chamber 190, elongated supports 194, and hollow needles 198 together comprise the alternate form of the vial fill means of the apparatus of the invention. The method of operation of this alternate form of fill means will presently be described.

Figure 37:
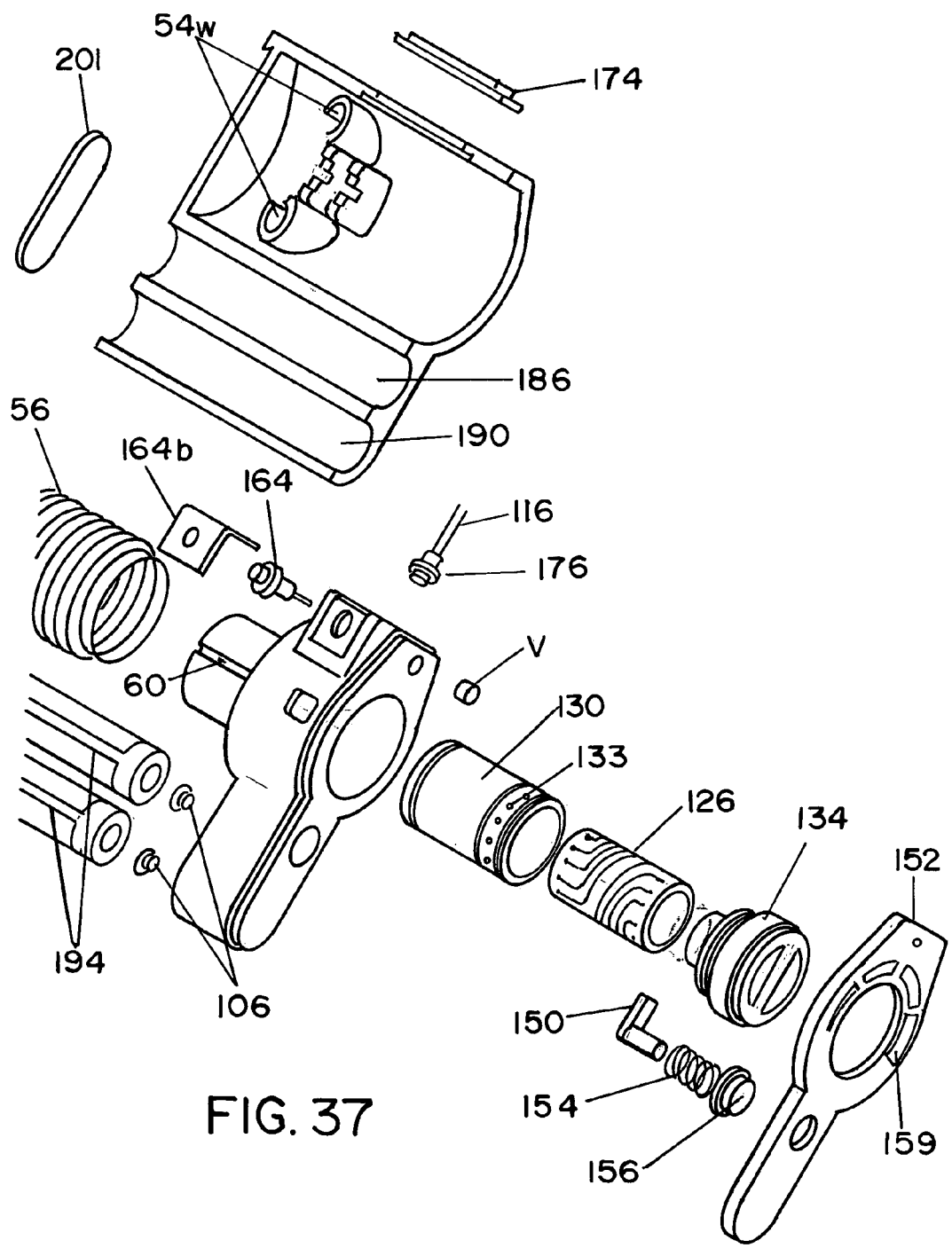
FIGS. 37 and 37A when considered together comprise a generally perspective, exploded view of the assembly shown in FIG. 30 (hereinafter collectively referred to as FIG. 37)
Figures 37A, 37B, 37C:
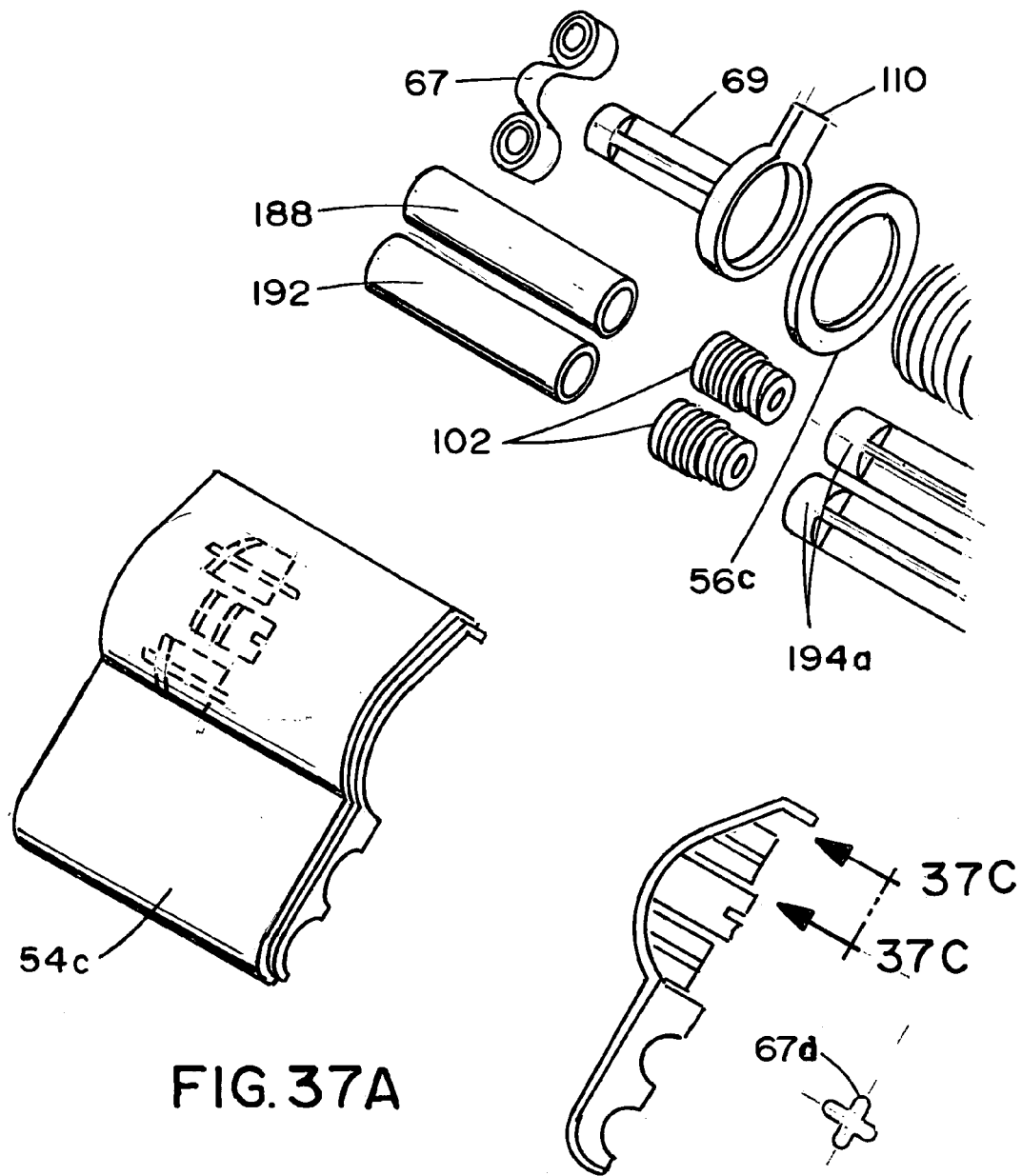
FIG. 37B is an end view of the snap together housing component shown in the lower left hand portion of FIG. 37A.
FIG. 37C is a view taken along lines 37C—37C of FIG. 37B.

Forming another very important aspect of the apparatus of this latest form of the invention is a novel flow control means that is connected to first portion 176 of outer housing 174. This flow control means, which is identical in construction and operation to that described in connection with the first embodiment of the invention, functions to precisely control the rate outwardly of fluid flow from reservoir 58 (FIG. 31) and toward the patient. As before, the flow control means comprises a flow control member 126 that is telescopically receivable within casing 130 and a selector knob 134 that is interconnected with control member 126 in the manner shown in FIGS. 15 and 16. When the flow control member is properly positioned within outer casing 130, the inner surface of the outer casing wall cooperates with channels 128 provided in the control member to form a plurality of generally spiral shaped fluid flow passageways of different overall lengths and flow capacities. Selector knob 134, which is rotatably mounted within housing portion 176, functions to rotate the assembly made up of outer casing 130 and flow control member 126 (FIG. 37). In this way, a selected outlet 132 in casing 130 can be selectively aligned with an outlet flow passageway 118 provided in forward housing portion 176 (FIG. 30).

Also forming a part of the fluid dispensing apparatus of this latest form of the invention is dispensing means for dispensing fluid to the patient. This dispensing means is also identical to that previously described and comprises an administration set 114 that is connected to the first portion 176 of housing 174 in the manner shown in FIG. 27 of the drawings. The proximal end 116a of administration line 116 of the administration set is in communication with fluid passageway 118 in the manner best seen in FIGS. 30 and 31.

Figure 31:
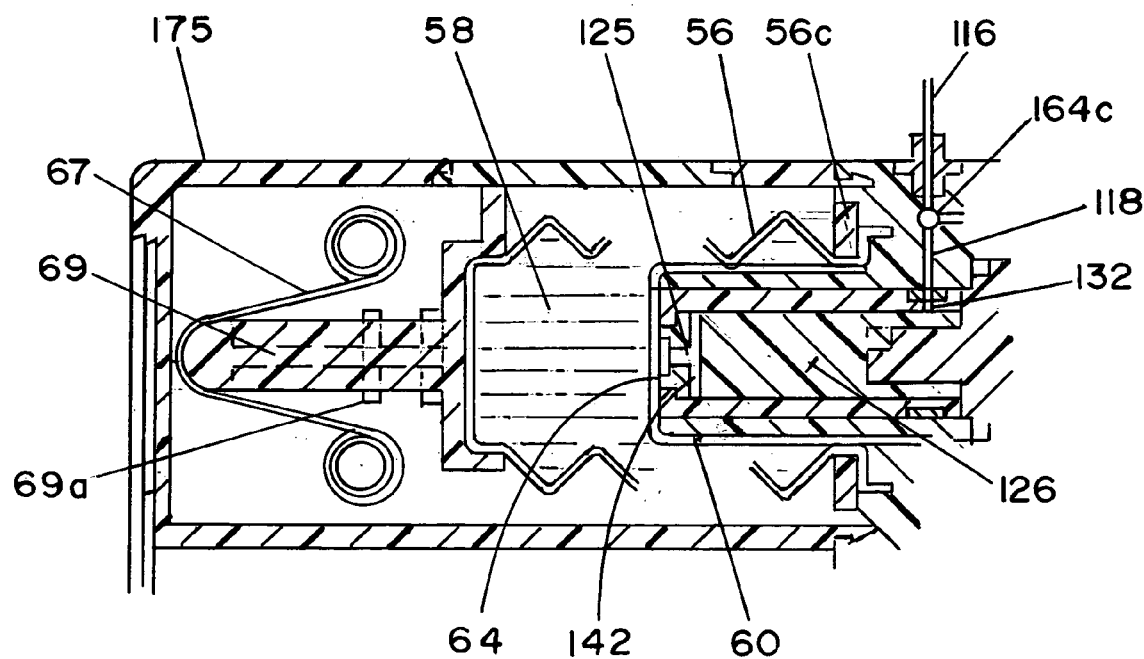
FIG. 31 is a cross-sectional view similar to FIG. 30, but showing the fluid reservoir filled with fluid.
Figure 33:
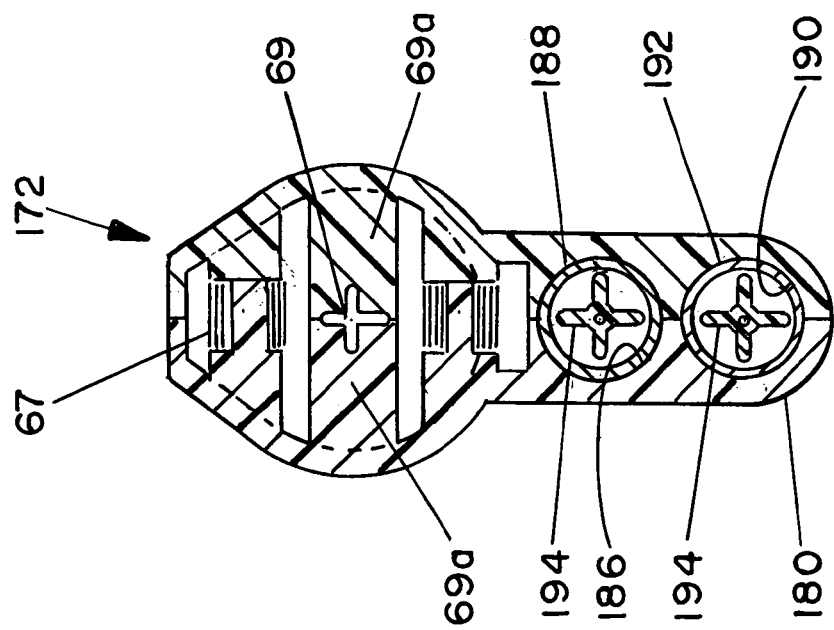
FIG. 33 is a cross-sectional view taken along lines 33—33 of FIG. 30.
Figure 32:
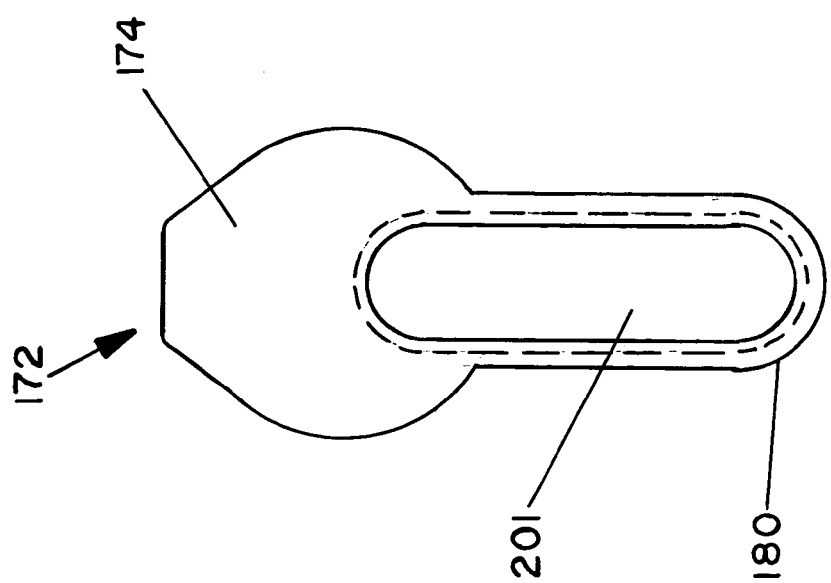
FIG. 32 is a left end view of the apparatus shown in FIG. 27.
Figure 34:
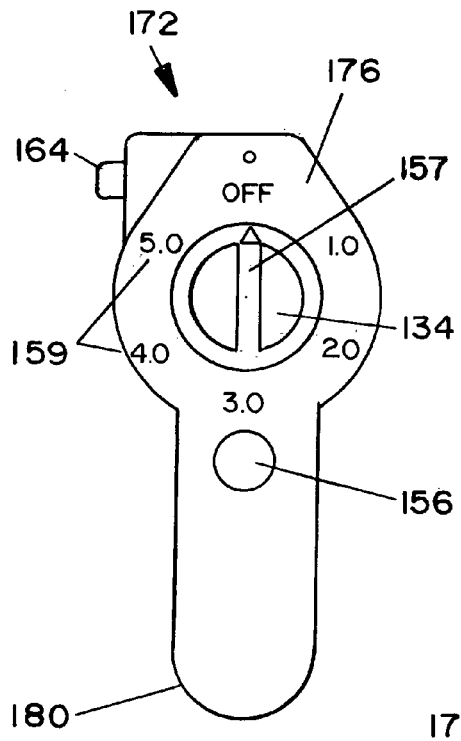
FIG. 34 is a right end view of the apparatus shown in FIG. 27.

Turning particularly to FIGS. 30 and 37, each of the shell vials 188 and 192 can be seen to be of the same construction as the shell vial illustrated in FIG. 8A and as earlier described herein. After removal of the vial cover 201, which forms a part of the third portion of housing 174 (FIGS. 30 and 37), vials 188 and 192 can be inserted into chambers 186 and 190 respectively. As the fill vials are so introduced and the plungers 102 thereof are threadably interconnected with ends 194a of supports 194, the sharp ends of the elongated needles 198 will pierce the central walls 102a of the elastomeric plungers. Continuous pushing movement of the vials into chambers 186 and 190 will cause the structural supports 194 to move the elastomeric plungers inwardly of the vial chambers. As the plungers move inwardly of the vial, the fluid contained within the vial chambers will be expelled there from into the hollow elongated needles 198. As best seen in FIG. 30, the fluid will then flow past umbrella type check valves 106 and into passageways 204 formed in third portion 180 of the apparatus housing. From passageway 204 the fluid will flow into passageway 182 and then into reservoir 58 of the bellows component 56 via inlet channel 60 (FIGS. 30, 31, and 37). It is to be understood that the vials 188 and 192 can contain the same or different medicinal fluids and can be introduced into their respective chambers either one at a time, or simultaneously.

It is also to be understood that, if desired, the reservoir of the bellows component can be filled by alternate filling means of the character previously described, namely a filling means which comprises a syringe having a needle adapted to pierce the pierceable septum 84 which is mounted within third portion 180 of the apparatus housing. As the reservoir 58 fills with fluid either from the fill vials or from the filling syringe, any gases trapped within the reservoir will be vented to atmosphere via vent means "V" mounted in portion 176 of the housing.

Upon opening the fluid delivery path to the administration set in a conventional manner, the stored energy means, or member 67, will tend to return to its starting configuration thereby controllably urging fluid flow outwardly of reservoir 58 via the flow control means of the invention which functions in the manner previously described. Indexing means of the character previously described functions to index the position of the selector knob. Similarly disabling means of the character previously described can be used to disable the apparatus of this latest form of the invention Turning next to FIGS. 38 through 48, still another form of the dispensing apparatus of the present invention is there illustrated and generally designated by the numeral 212. This alternate form of the apparatus of the invention is also similar in many respects to that shown in FIGS. 1 through 26 and like numerals are used in FIGS. 38 through 48 to identify like components. The primary difference between this latest form of the invention and that shown in FIGS. 1 through 26 is that the vial fill means for filling the device reservoir is of a different configuration from that used in both the first and second previously described embodiments of the invention. More particularly, as will presently be described in greater detail, this alternate form of vial fill means comprises a vial cartridge having a hollow glass or plastic body portion that defines a fluid chamber that is closed by a pierceable, elastomeric septum.

Figure 38:
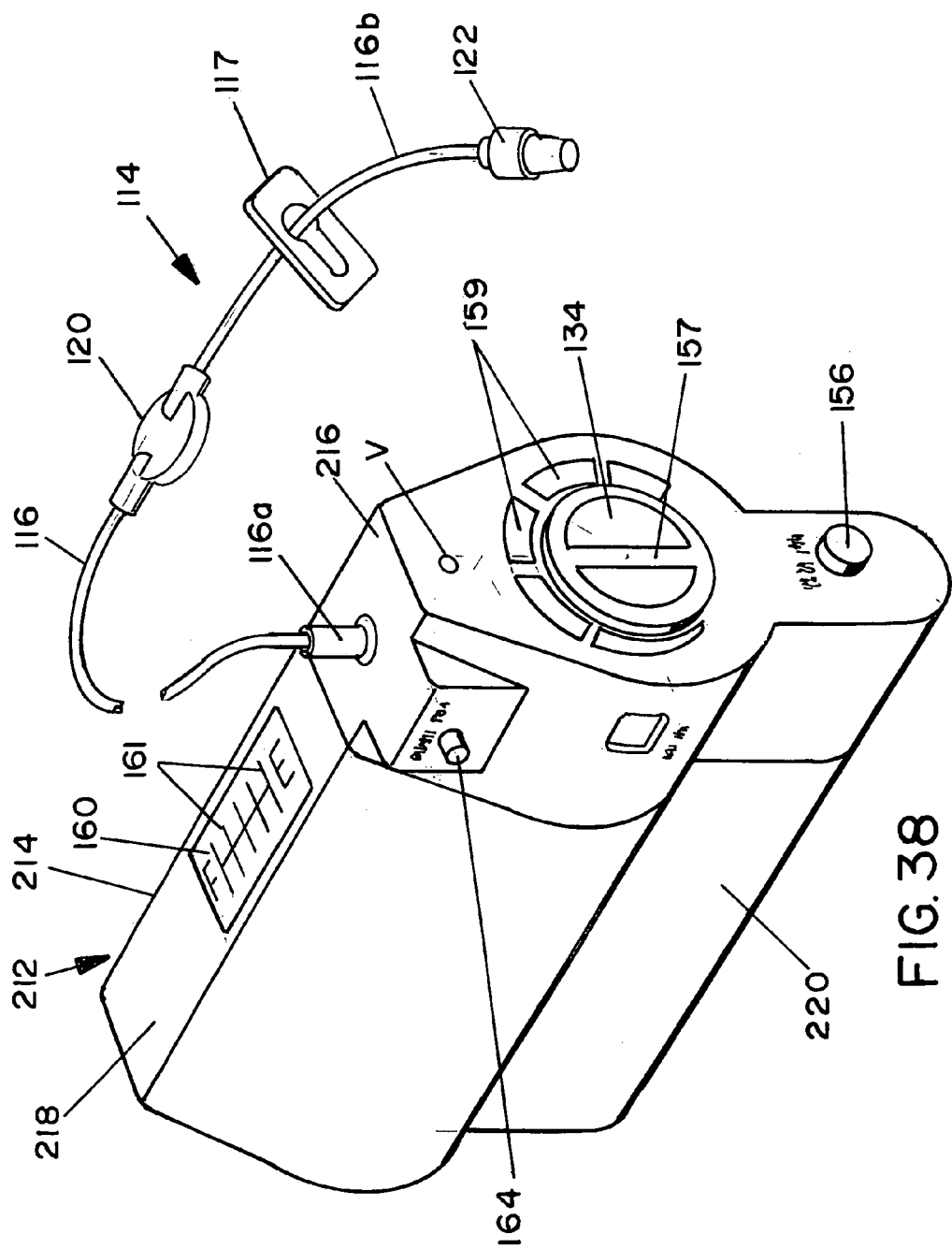
FIG. 38 is a generally perspective view of yet another embodiment of the medicament infusion apparatus of the present invention for dispensing fluids at a uniform rate.
Figure 39:
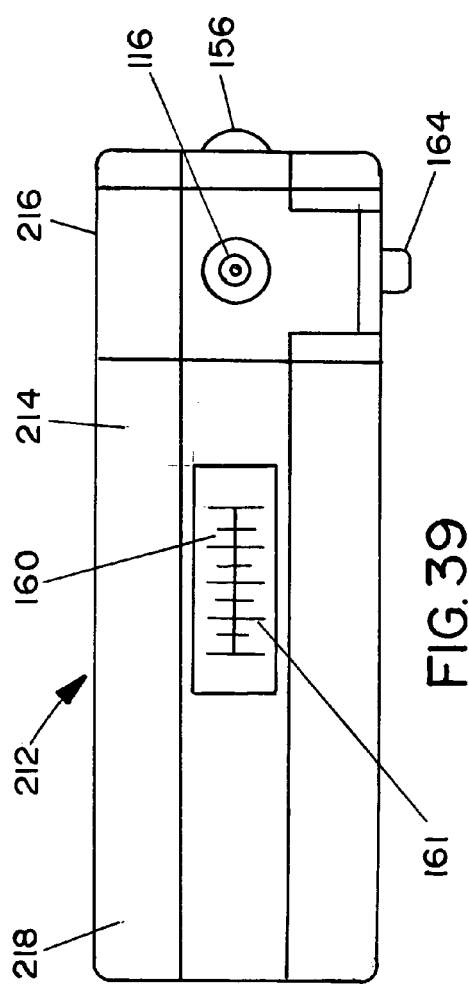
FIG. 39 is a top plan view of the embodiment of the medicament infusion apparatus shown in FIG. 38.
Figure 40:
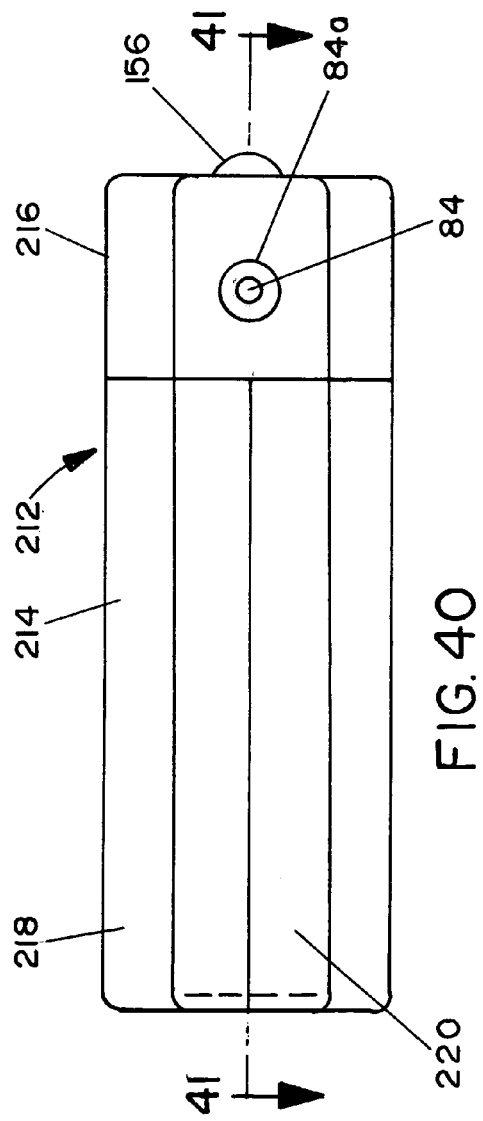
FIG. 40 is a bottom plan view of the apparatus shown in FIG. 38.

As best seen in FIG. 38, the apparatus here comprises an outer housing 214 having a first, second and third portions 216, 218 and 220 respectively. Disposed within outer housing 214 is an inner, expandable housing 56 which is identical in construction and operation to that described in connection with the embodiment of FIGS. 1 through 26.

Disposed within second portion 218 of outer housing 214 is the novel stored energy means of the invention for acting upon inner expandable housing 56 in a manner to cause the fluid contained within fluid reservoir 58 thereof to controllably flow outwardly of the housing. In this latest form of the invention, this stored energy means is also identical in construction and operation to that previously described and comprises a constant force spring 67.

With regard to the fill means of this latest form of the invention, which is carried by the third portion 220 of the outer housing, as before, this important fill means functions to fill the reservoir 58 with the fluid to be dispensed. This fill means here comprises the previously described septum fill means, which is identical to that previously described, and also includes the previously mentioned, cartridge type fill vial which is of the construction best seen in FIG. 41A of the drawings.

Figure 41:
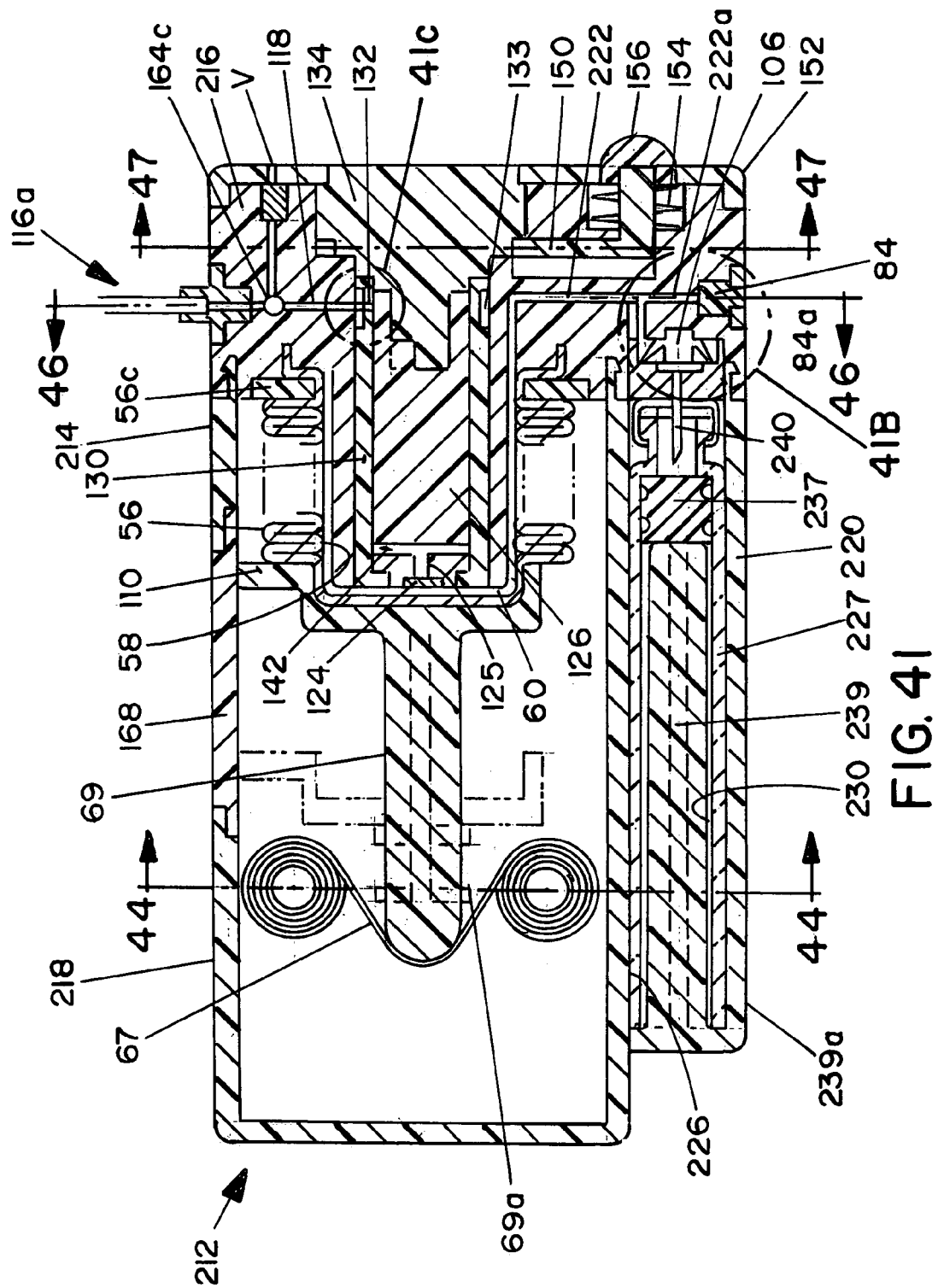
FIG. 41 is a cross-sectional view taken along lines 41—41 of FIG. 40.

As to the septum fill means, as illustrated in FIG. 41, third portion 220 includes a fluid passageway 222 which is in communication with inlet 60 of fluid reservoir 58. Proximate its lower end 222a, fluid passageway 222 communicates with a cavity formed within the third portion 220 of the housing. Disposed within cavity is a pierceable septum 84 that comprises a part of the septum fill means of this latest form of the invention. As before, elastomeric septum 84 is held in position by a retainer 84a and is pierceable by the needle of the syringe which contains the medicinal fluid to be dispensed and which can be used in a conventional manner to fill or partially fill reservoir 58 via passageway 222.

Figure 41A:
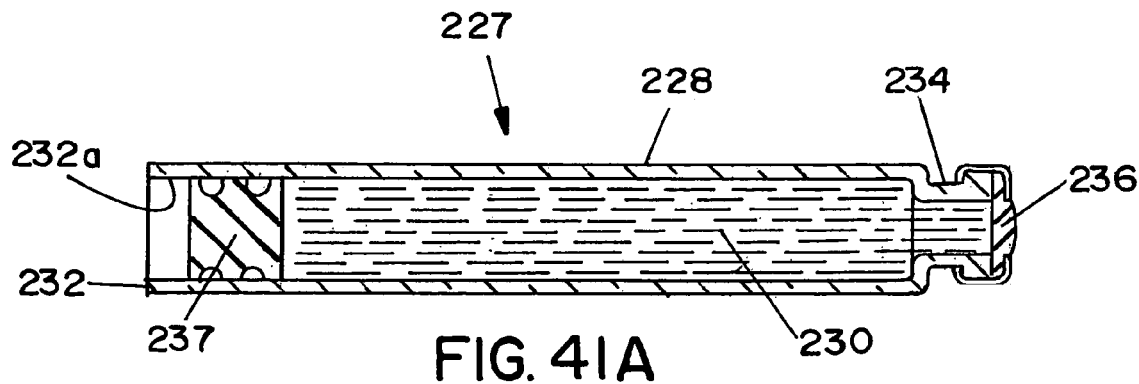
FIG. 41A is an enlarged, cross-sectional view of the fill vial cartridge of the apparatus of the invention shown in FIG. 41
Figure 41D:
FIG. 41D is an enlarged, cross-sectional view of the elastomeric sealing band shown in FIG. 41C.
Figure 41B:
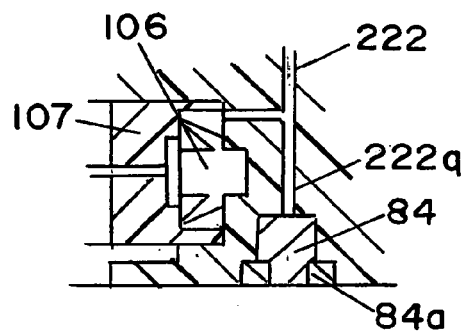
FIG. 41B is an enlarged, cross-sectional view of the area designated as 41B in FIG. 41.
Figure 41C:
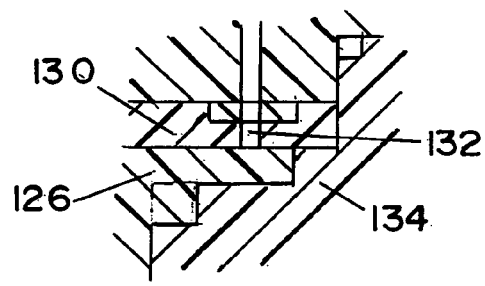
FIG. 41C is an enlarged, cross-sectional view of the area designated as 41C in FIG. 41.
Figure 42:
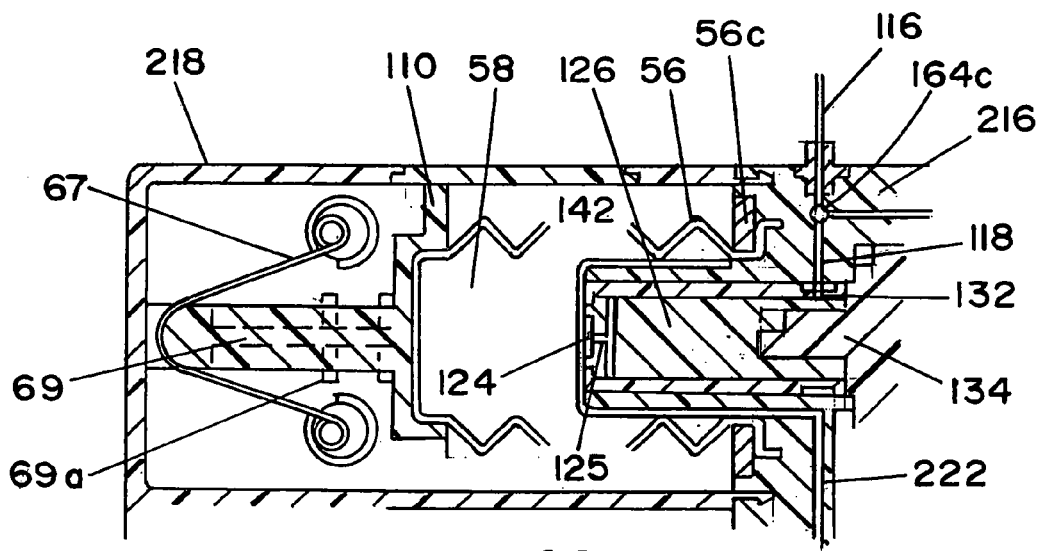
FIG. 42 is a cross-sectional view similar to FIG. 41, but showing the fluid reservoir filled with fluid.
Figure 44:
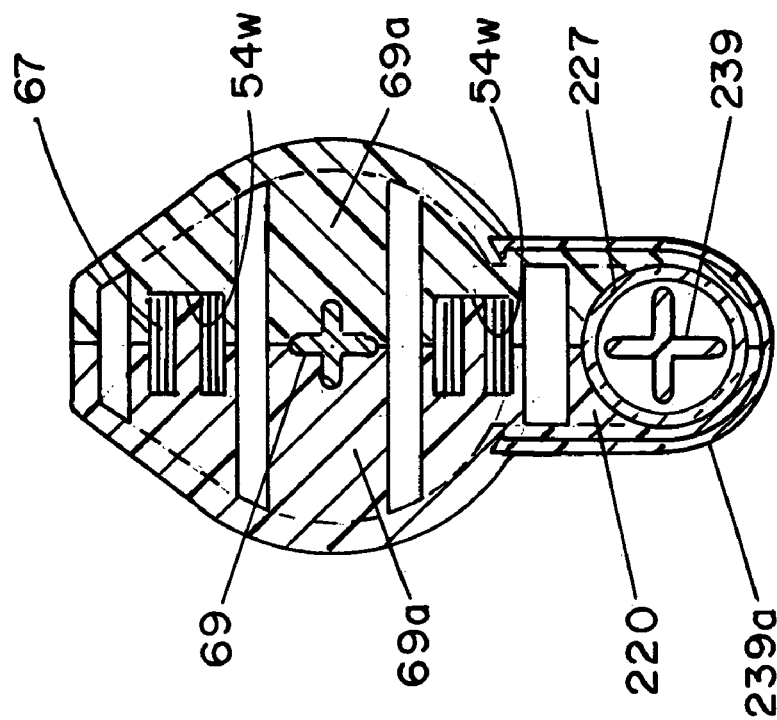
FIG. 44 is a cross-sectional view taken along lines 44—44 of FIG. 41.
Figure 43:
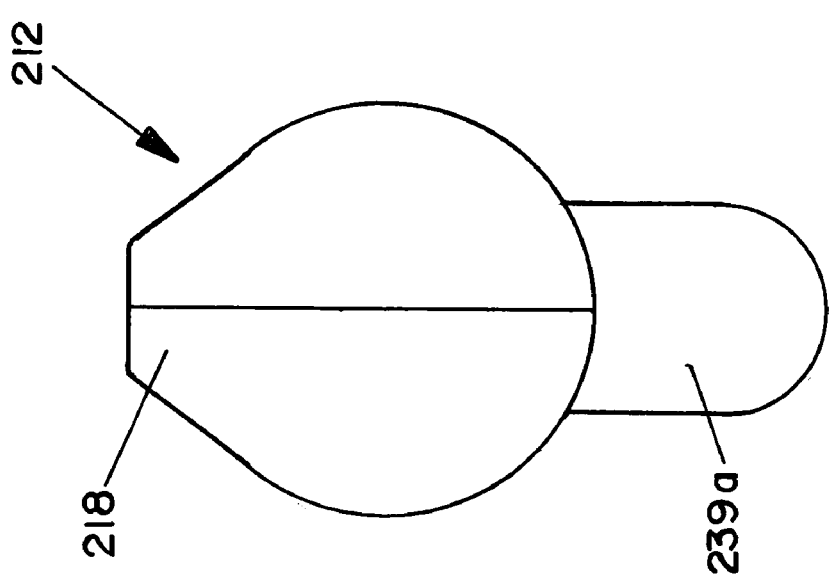
FIG. 43 is a left end view of the apparatus shown in FIG. 38.
Figure 45:
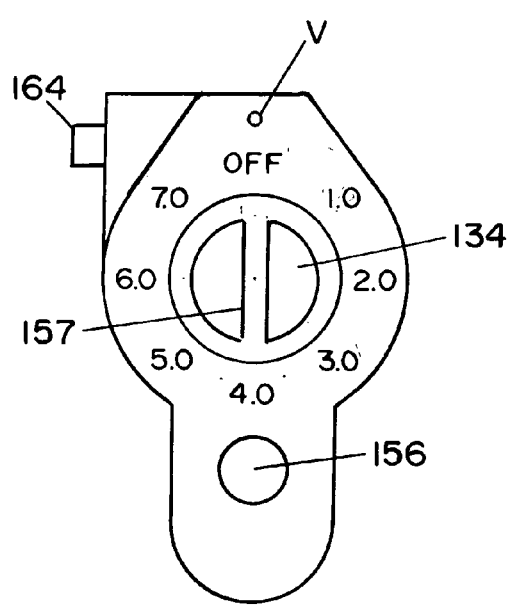
FIG. 45 is a right end view of the apparatus shown in FIG. 38.
Figure 46:
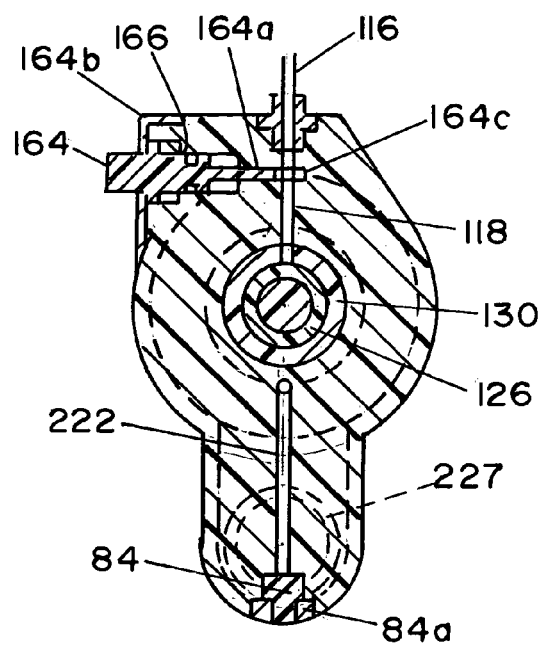
FIG. 46 is a cross-sectional view taken along lines 46—46 of FIG. 41.
Figure 47:
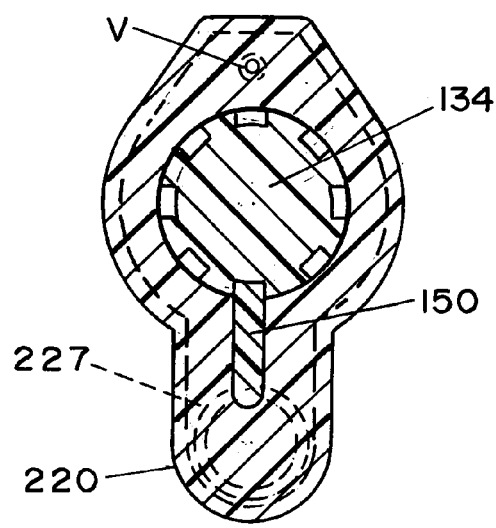
FIG. 47 is a cross-sectional view taken along lines 47—47 of FIG. 41.
Figure 48:
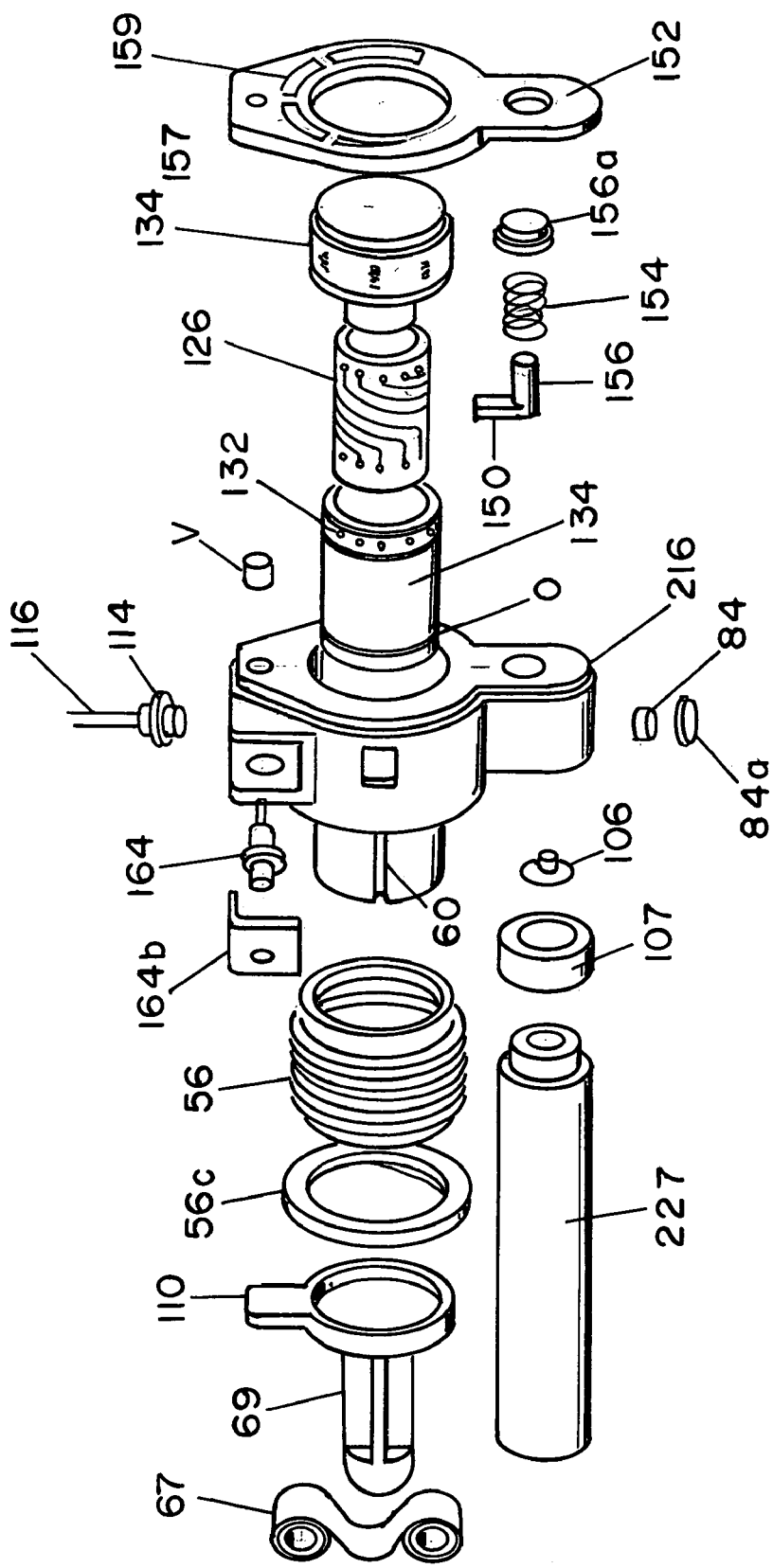

Third portion 220 of the housing also includes a first chamber 226 for telescopically receiving the previously mentioned cartridge fill vial, which is generally designated in the drawings by the numeral 227. As shown in FIG. 41A, cartridge fill vial 227 comprises a hollow glass or plastic body portion 228 that defines a fluid chamber 230. Fill vial 227 has an open first end 232 and a second end 234 that is closed by a pierceable, elastomeric septum 236. An elastomeric plunger 237 is reciprocally movable within fluid chamber 230. As shown in FIG. 41, a hollow needle to 240 is mounted within third portion 220 of the device housing and is located proximate the inboard end of chamber 226. Hollow needle 240 is adapted to pierce septum 236 when the fill vial is inserted into chamber 226 and pushed into the position shown in FIG. 41. More particularly, a pusher member 239 which is housed within a casing 239a (FIG. 48) pushes the fill vial inwardly of chamber 226.

Forming an important aspect of the apparatus of this latest form of the invention is a novel flow control means that is connected to first portion 216 of outer housing 214. This flow control means, which is identical in construction and operation to that described in connection with the first embodiment of the invention, functions to precisely control the rate outwardly of fluid flow from reservoir 58 and toward the patient. As before, the flow control means comprises a flow control member 126 that is telescopically receivable within casing 130 and a selector knob 134 that is interconnected with control member 126 in the manner 134 that is interconnected with control member 126 in the manner shown in FIGS. 15 and 16. When the flow control member is properly sealably positioned within outer casing 130, the inner surface of the outer casing wall cooperates with channels 128 provided in the control member to form a plurality of generally spiral shaped fluid flow passageways of different overall lengths, width, depths and flow capacities. Selector knob 134, which is rotatably mounted within housing portion 216, functions to rotate the assembly made up of outer casing 130 and flow control member 126. In this way, a selected outlet 132 in casing 130 can be selectively aligned with an outlet flow passageway 118 provided in forward housing portion 216 (FIG. 41).

Also forming a part of the fluid dispensing apparatus of the latest form of the invention is dispensing means for dispensing fluid to the patient. This dispensing means is also identical to that previously described and comprises an administration set that is connected to the first portion 216 of housing 214 in the manner shown in FIG. 38 of the drawings. The proximal end 116a of administration line 116 of the administration set is in communication with fluid passageway 118 in the manner best seen in FIG. 41.

It is also to be understood that, if desired, the reservoir of the bellows component can also be filled by alternate filling means of the character previously described which comprises a syringe having a needle adapted to pierce the pierceable septum 84 which is mounted within third portion 220 of the apparatus housing. As the reservoir 58 fills with fluid from the fill vials or from the filling syringe, any gases trapped within the reservoir will be vented to atmosphere via vent means "V" mounted in portion 216 of the housing.

Upon opening the fluid delivery path to the administration set, the stored energy means, or member 67, will tend to return to its starting configuration thereby controllably urging fluid flow outwardly of reservoir 58 via the flow control means of the invention which functions in the manner previously described. Indexing means of the character previously described functions to index the position of the selector knob. Similarly, as in the earlier described embodiments, disabling means of the character previously described can be used to disable the apparatus of this latest form of the invention.

Turning next to FIGS. 49 through 63, still another form of the dispensing apparatus of the present invention is there illustrated and generally designated by the numeral 242. This alternate form of the apparatus of the invention is also similar in many respects to that shown in FIGS. 1 through 26 and like numerals are used in FIGS. 49 through 63 to identify like components. The primary difference between this latest form of the invention and that shown in FIGS. 1 through 26 is that the vial fill means for filling the device reservoir is of a different configuration from that used in each of the previously described embodiments of the invention. More particularly, as will presently be described in greater detail, this alternate form of vial fill means comprises a first vial cartridge that is of identical construction and operation to that described in connection with the embodiment of the invention shown in FIGS. 38 through 48. However, the vial fill means also here includes a second vial cartridge that is of a uniquely different construction from the previously described medicament containing vials. More particularly, this second vial cartridge is specially designed to enable the intermixing of an internally contained lypholized drug with a suitable diluent or mixing agent prior to the delivery of the mixture of the fluid reservoir of the device.

Figure 49:
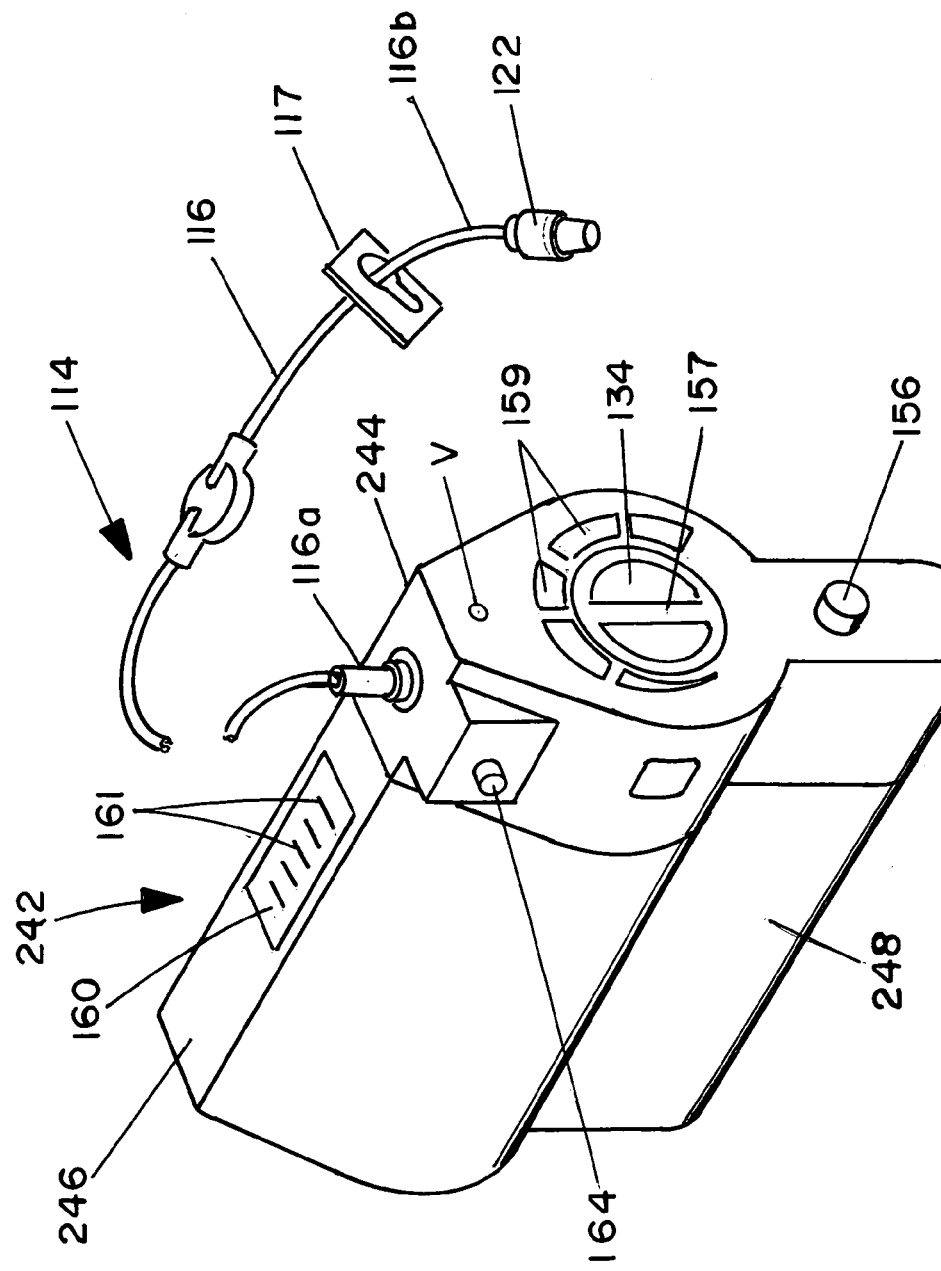
FIG. 49 is a generally perspective view of still another embodiment of the medicament infusion apparatus of the present invention for dispensing fluids at a uniform rate.
Figure 50:
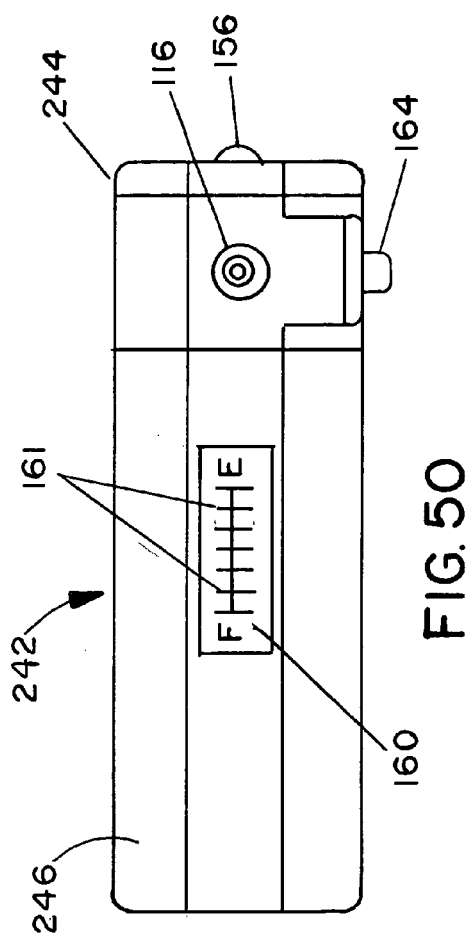
FIG. 50 is a top plan view of the embodiment of the medicament infusion apparatus shown in FIG. 49.
Figure 51:
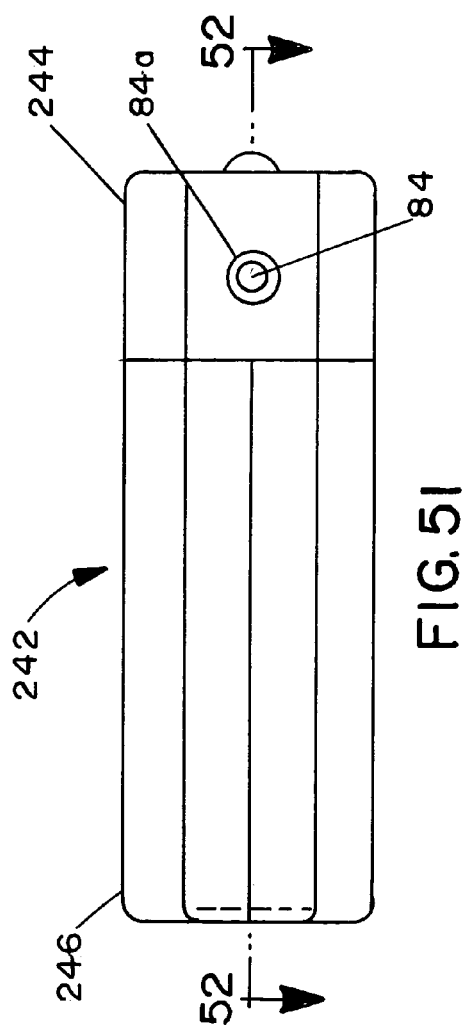
FIG. 51 is a bottom plan view of the apparatus shown in FIG. 49.
Figure 57:
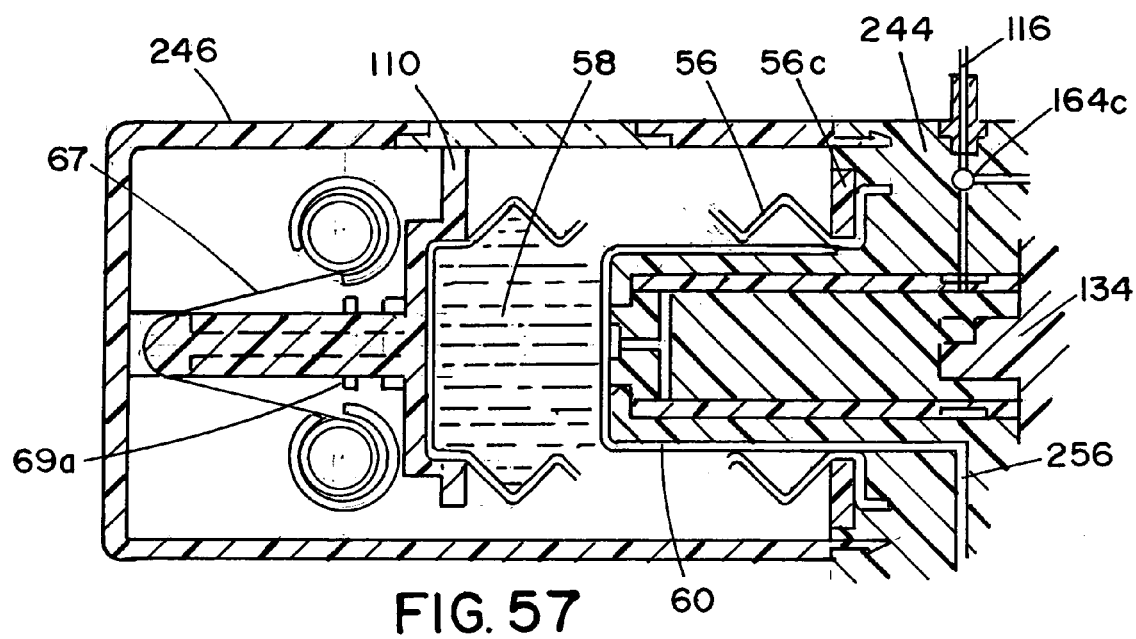
FIG. 57 is a cross-sectional view similar to FIG. 52, but showing the fluid reservoir filled with fluid.
Figures 58, 59:
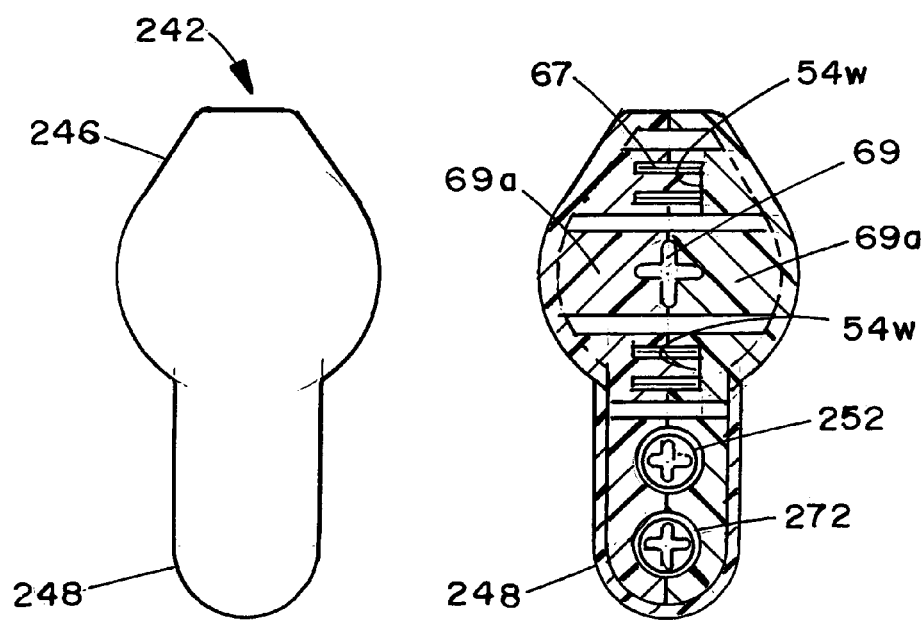
FIG. 58 is a left end view of the apparatus shown in FIG. 49.
FIG. 59 is a cross-sectional view taken along lines 59—59 of FIG. 52.
Figure 60:
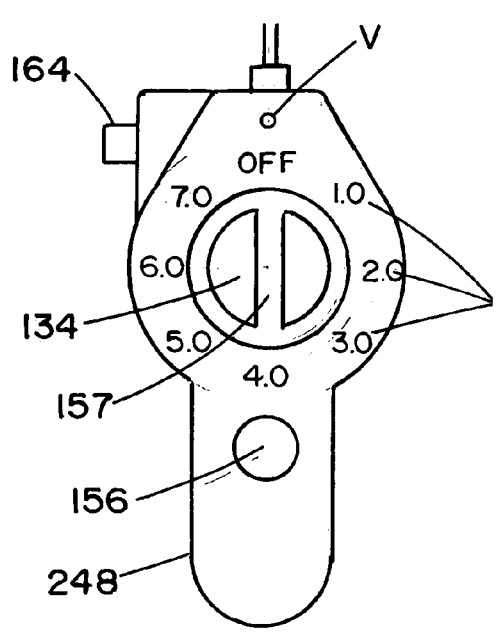
FIG. 60 is a right end view of the apparatus shown in FIG. 49.
Figure 61:
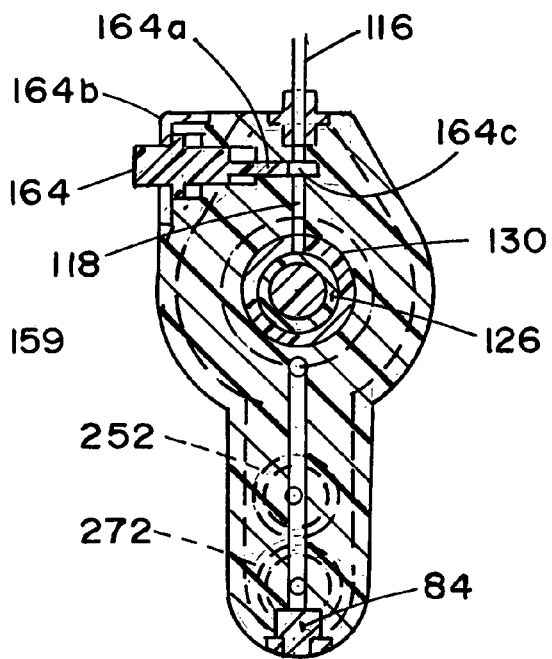
FIG. 61 is a cross-sectional view taken along lines 61—61 of FIG. 52.
Figure 62:
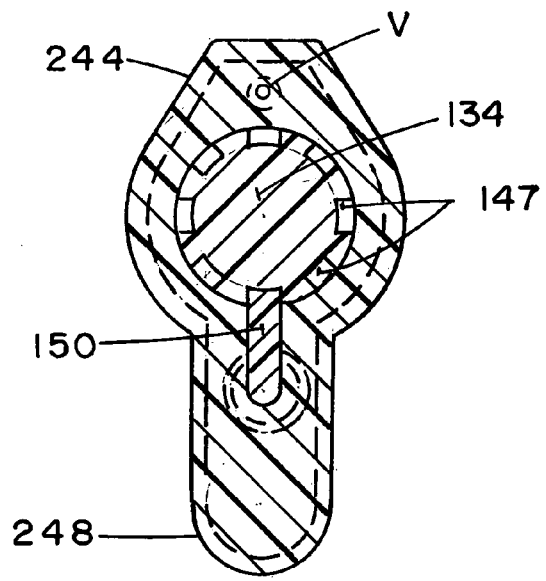
FIG. 62 is a cross-sectional view taken along lines 62—62 of FIG. 52.
Figure 63:
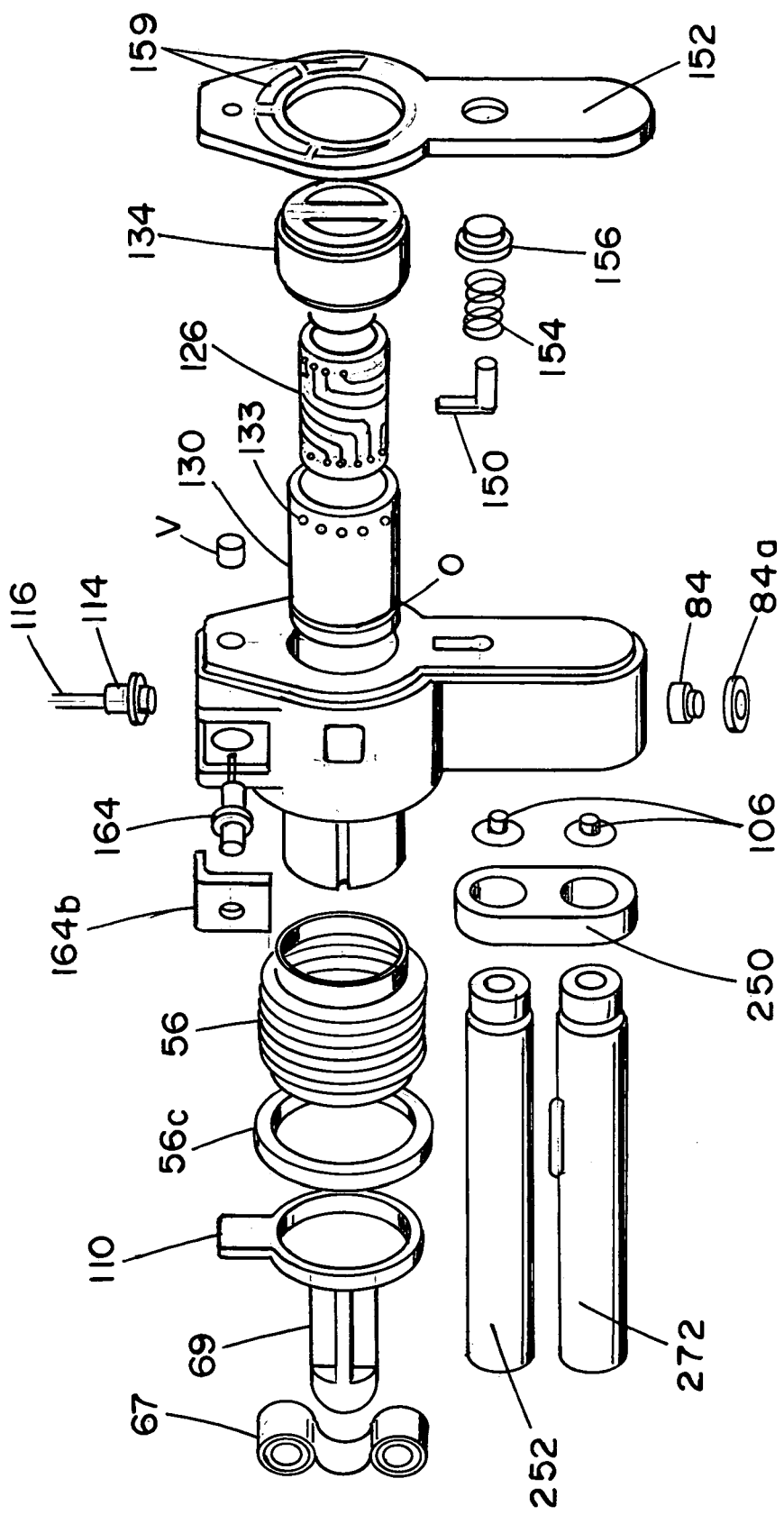

As best seen in FIG. 49, the apparatus here comprises an outer housing 242 having a first, second and third portions 244, 246 and 248 respectively. Disposed within outer housing 242 is an inner, expandable housing 56 which is identical in construction and operation to that described in connection with the embodiment of FIGS. 1 through 26.

Disposed within second portion 246 of outer housing 242 is the novel stored energy means of the invention for acting upon inner expandable housing 56 in a manner to cause the fluid contained within fluid reservoir 58 thereof to controllably flow outwardly of the housing. In this latest form of the invention, this stored energy means is also identical in construction and operation to that previously described and comprises a constant force spring 67.

With regard to the fill means of this latest form of the invention, which is carried by the third portion 248 of the outer housing, as before, this important fill means functions to fill the reservoir 58 with the fluid to be dispensed. This fill means here comprises the previously described septum fill means, which is identical to that previously described, and also includes the previously mentioned, first and second cartridge type vial fill vials generally designated in FIG. 52 by the numerals 252 and 272 respectively. As to the septum fill means, as illustrated in FIG. 52, third portion 248 includes a fluid passageway 256 which is in communication with inlet 60 of fluid reservoir 58. Proximate its lower end 256a, fluid passageway 256 communicates with a cavity 258 formed within the third portion 248 of the housing. Disposed within cavity 258 is an elastomeric pierceable septum 84 that comprises a part of the septum fill means of this latest form of the invention. As before, septum 84 is held in position by a retainer 84a and is pierceable by the needle of the syringe which contains the medicinal fluid to be dispensed and which can be used in a conventional manner to fill or partially fill reservoir 58 via passageway 256.

Third portion 248 of the housing also includes a first chamber 260 for telescopically receiving the previously mentioned, first cartridge fill vial 252, which is identical in construction and operation to the previously described cartridge fill vial 228, the construction of which is shown in FIG. 41A. As illustrated in FIG. 52, a hollow needle 240 is mounted within third portion 248 of the device housing and is located proximate the inboard end of chamber 260. Hollow needle 240 is adapted to pierce septum 236 when the first cartridge fill vial is inserted into chamber 260 and pushed forwardly into the position shown in FIG. 52.

With respect to second reconstitution cartridge fill vial 272, this fill vial, which is more clearly illustrated in FIGS. 53 and 54 of the drawings, comprises a container of special design that uniquely contains a lyophilized drug 262 that is separated from a reconstituting fluid 264 by a barrier stopper 266 (FIG. 53). Lyophilized drug 262 can, by way of example, comprise anti-infectives, cardiac drugs or various other types of beneficial agents.

As illustrated in FIG. 52, portion 248 of the device housing includes a pair of spaced apart pusher members 268 and 270 which engage plungers 237 and 271 respectively to push them forwardly of their respective container reservoirs.

Considering in more detail the novel bypass cartridge assembly 272, as best seen in FIG. 53, this cartridge assembly includes a vial 272 that is sealed at one end by elastomeric plunger 271 and at the other end by a pierceable septum 274 (FIGS. 52 and 53). Formed intermediate the ends of vial 254 is a raised outer wall portion 272a which after installation of the cartridge permits fluid 264 to bypass a barrier stopper 266 as the barrier stopper is urged inwardly of the container by pressure exerted thereon by the fluid 264, which is being pushed by plunger/stopper 271 resulting from force exerted on pusher element member 270. Fluid 264 exerts pressure on barrier member 266 as a result of the inward movement of plunger 271 by the pusher member as the vial is fully mated with the apparatus housing.

A continued inward pressure exerted on plunger 271 will cause fluid 264 to flow past baffler member 266 via the internal passageway defined wall portion 272a so as to reconstitute the lyophulized drug 262. A continued pressure exerted on plunger 271 by the pusher member will cause the reconstituted drug formed by the fluid 264 which has been intermixed with drug 262 to flow through a hollow cannula 240 past check valve 106, into a stub passageway 282 and then into a passageway 256 and finally into the device reservoir 58.

As previously mentioned, plunger 237, which is disposed within vial 252, is moved by a support 268 of a vial cover 280 (FIG. 52) as the vial cover is mated with the apparatus housing and locked in position. As plunger 237 is moved inwardly of vial reservoir 252, the fluid contained in the reservoir will be forced through the upper hollow needle 240, passed the upper umbrella check valve 106 mounted within third housing portion 248, into a stub passageway 282, into a passageway 256 and finally into the device reservoir. As the fluid flows into the device reservoir, it will compress the stored energy means, or constant force spring 67 in the manner previously described.

Turning to FIGS. 55 and 56, an alternate form of drug intermixing vial is there shown. This fill cartridge is similar in some respects to fill cartridge 254 and includes a vial 285 that is sealed at one end by a plunger 286 and at the other end by a pierceable septum 274. Formed intermediate the ends of vial 285 is a plurality of internal fluid flow passageways 292 which permit fluid 264 to bypass member or elastomeric barrier stopper 290 as the barrier stopper is urged inwardly of the container by pressure exerted thereon by fluid 264. Fluid 264 exerts pressure on barrier member 290 as a result of pusher member 270 of the housing exerting inward pressure on plunger 286, which pressure is, in turn, caused by the inward movement of plunger 286 as vial housing 285 is mated with the device housing portion 248.

A continued inward pressure exerted on plunger 286 will cause fluid 264 to flow past barrier member 290 via flow passageways 292 so as to reconstitute lyophilized drug 262 (FIG. 55). Further pressure exerted on plunger 286 will cause the reconstituted drug formed by the fluid 264 which has been intermixed with drug 262 to flow through hollow cannula 240, past lower check valve 106, into a stub passageway 277, into a passageway 256 and finally into the device reservoir 58 (FIG. 52).

Forming an important aspect of the apparatus of this latest form of the invention is a novel flow control means that is connected to first portion 244 of the outer housing. This flow control means, which is identical in construction and operation to that described in connection with the first embodiment of the invention, once again functions to precisely control the rate outwardly of fluid flow from reservoir 58 and toward the patient. As before, the flow control means comprises a flow control member 126 that is telescopically receivable within casing 130 and a selector knob 134 that is interconnected with control member 126 in the manner shown in FIGS. 15 and 16. When the flow control member is properly positioned within outer casing 130, the inner surface of the outer casing wall cooperates with channels 128 provided in the control member to form a plurality of generally spiral shaped fluid flow passageways of different overall lengths and flow capacities. Selector knob 134, which is rotatably mounted within housing portion 244, functions to rotate the assembly made up of outer casing 130 and flow control member 126. In this way, a selected outlet 132 in casing 130 can be selectively aligned with an outlet flow passageway 118 provided in forward housing portion 244 (FIG. 52).

Also forming a part of the fluid dispensing apparatus of this latest form of the invention is dispensing means for dispensing fluid to the patient. This dispensing means is also identical to that previously described and comprises an administration set 114 that is connected to the first portion 244 of housing 242 in the manner shown in FIG. 49 of the drawings. The proximal end 116a of administration line 116 of the administration set is in communication with fluid passageway 118 in the manner best seen in FIG. 52.

It is also to be understood that, if desired, the reservoir of the bellows component can also be filled by alternate filling means of the character previously described which comprises a syringe having a needle adapted to pierce the pierceable septum 84 which is mounted within third portion 248 of the apparatus housing. As the reservoir 58 fills with fluid either from the fill vials or from the filling syringe, any gases trapped within the reservoir will be vented to atmosphere via vent means "V" mounted in portion 244 of the housing.

Referring now to FIGS. 64 through 95, yet another embodiment of the dispensing apparatus of the present invention is there illustrated and generally designated by the numeral 302. This alternate form of the apparatus of the invention is similar in some respects to that shown in FIGS. 1 through 26 and like numerals are used in FIGS. 64 through 84 to identify like components. The primary difference between this latest form of the invention and those previously discussed concerns the provision of a differently configured device housing and a differently configured flow rate control means.

Figure 64:
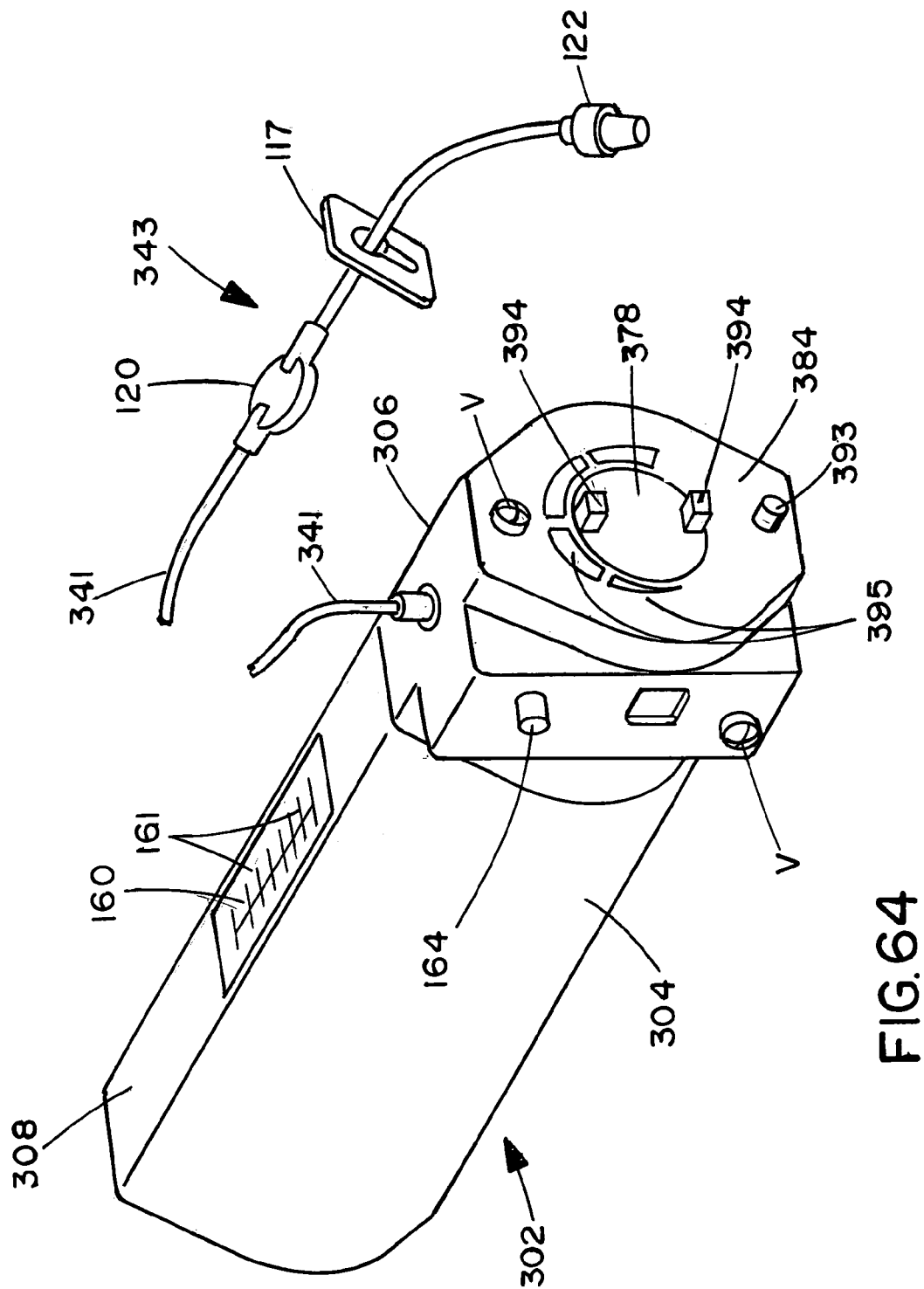
FIG. 64 is a generally perspective view of still another embodiment of the medicament infusion apparatus of the present invention for dispensing fluids at a uniform rate.
Figure 65:
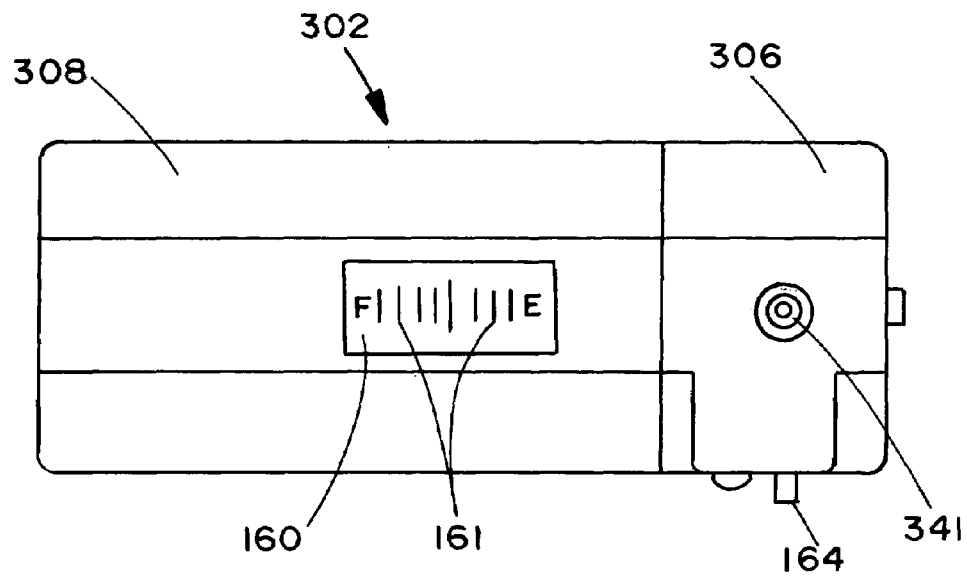
FIG. 65 is a top plan view of the embodiment of the medicament infusion apparatus shown in FIG. 64.
Figure 66:
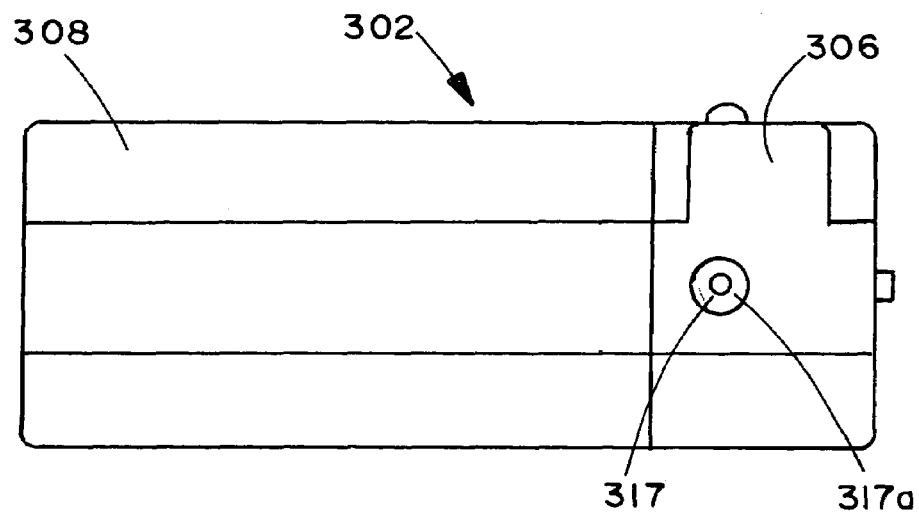
FIG. 66 is a bottom plan view of the apparatus shown in FIG. 64.

As best seen in FIG. 64, the apparatus here comprises an outer housing 304 having first and second portions 306 and 308 respectively. Disposed within outer housing 304 is an inner, expandable housing 310, which is generally similar in construction and operation to expandable housing 56, which housing was described in connection with the embodiment of FIGS. 1 through 26.

Also disposed within second portion 308 of outer housing 304 is the novel stored energy means of the invention for acting upon inner expandable housing 310 in a manner to cause the fluid contained within fluid reservoir 312 thereof to controllably flow outwardly of the housing. In this latest form of the invention, this stored energy means is identical in construction and operation to that previously described and here comprises a constant force spring 67 of the character previously described herein.

Figure 67:
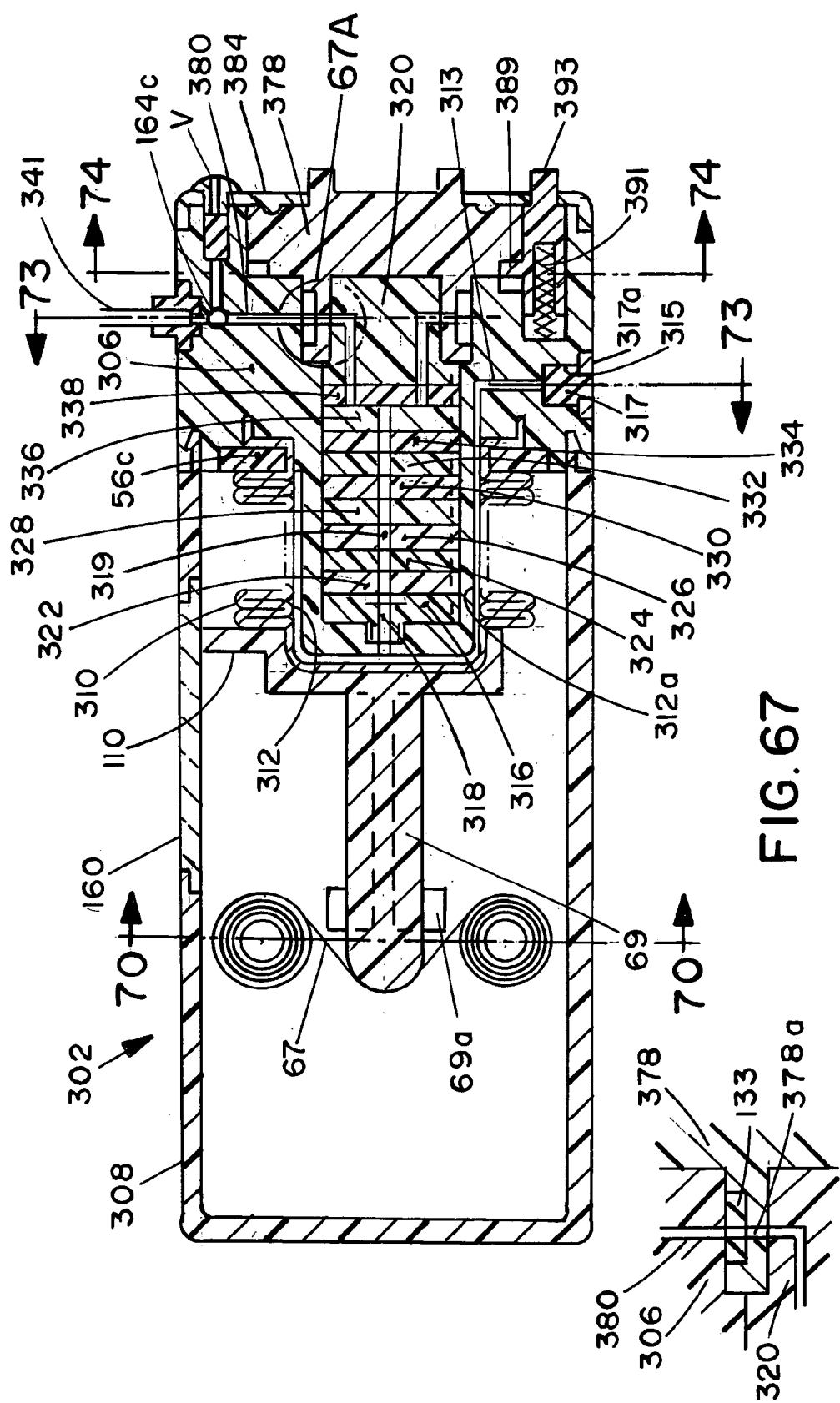
FIG. 67 is a longitudinal, cross-sectional view of the apparatus shown in FIG. 64.
Figure 68:
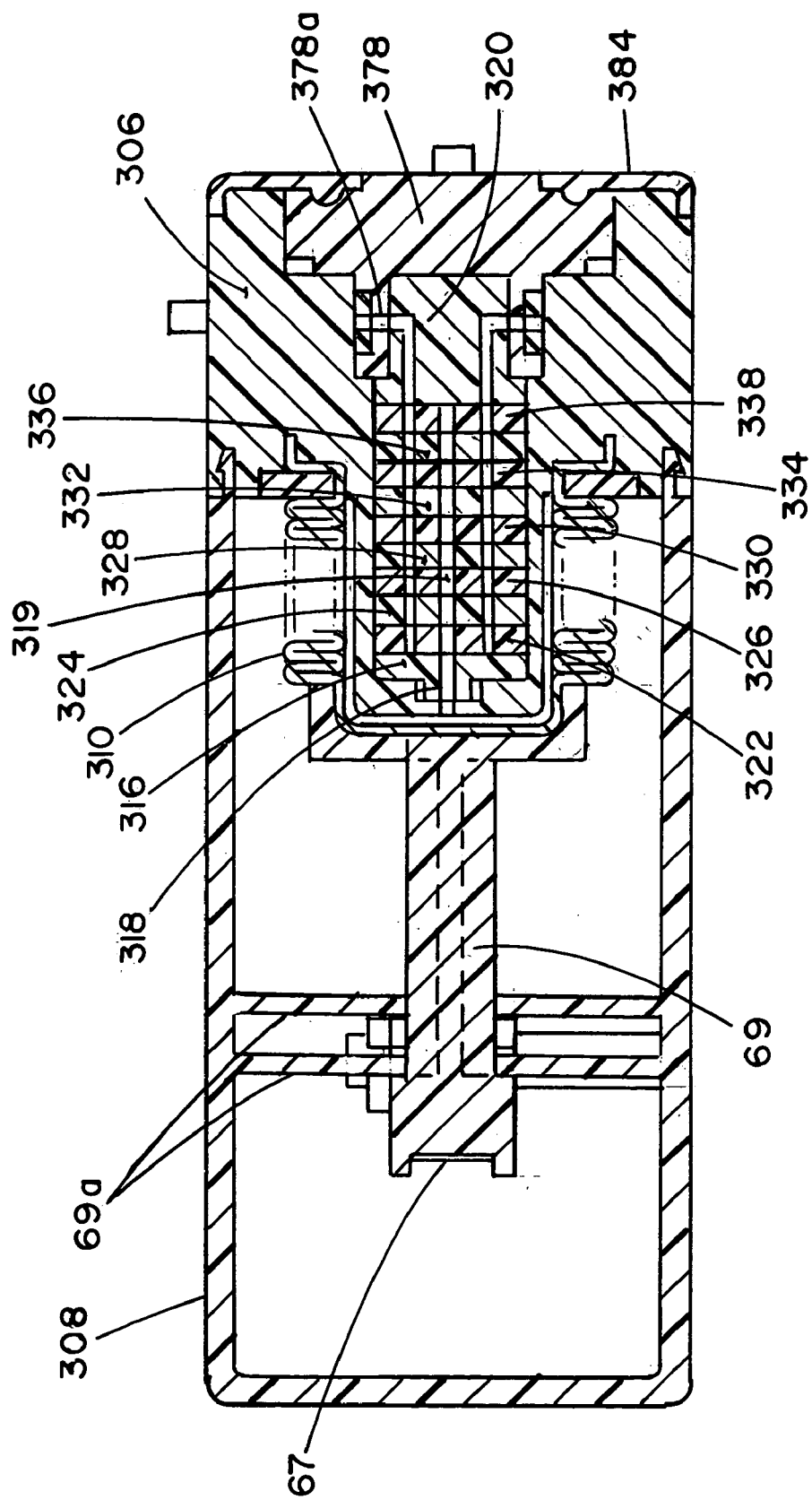
FIG. 68 is a cross-sectional view taken along lines 68—68 of FIG. 67.
Figure 69:
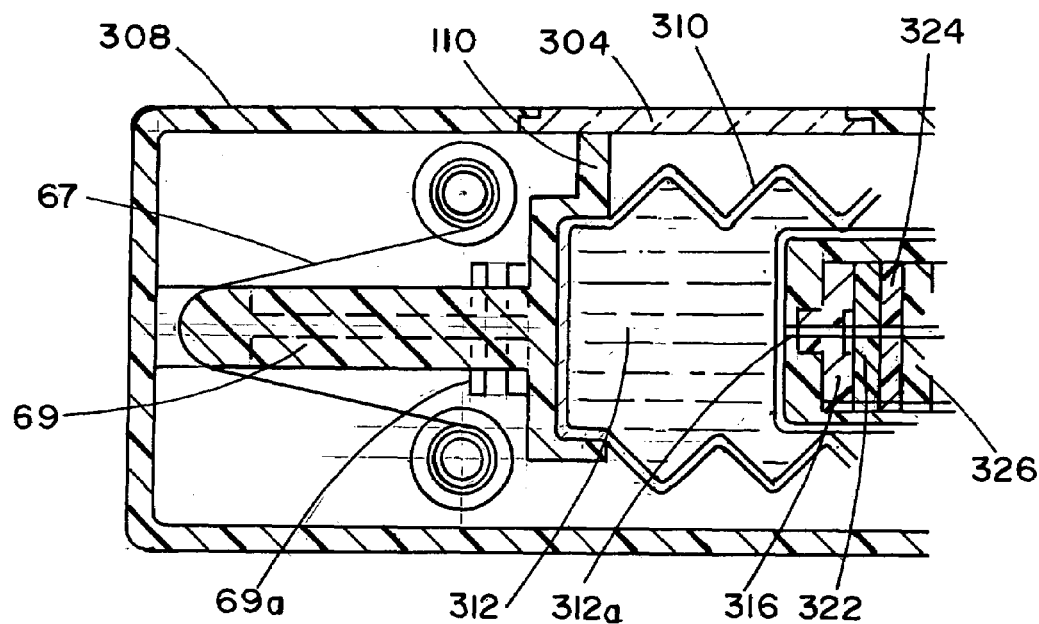
FIG. 69 is a cross-sectional view similar to FIG. 67, but showing the fluid reservoir filled with fluid.
Figures 70, 71:
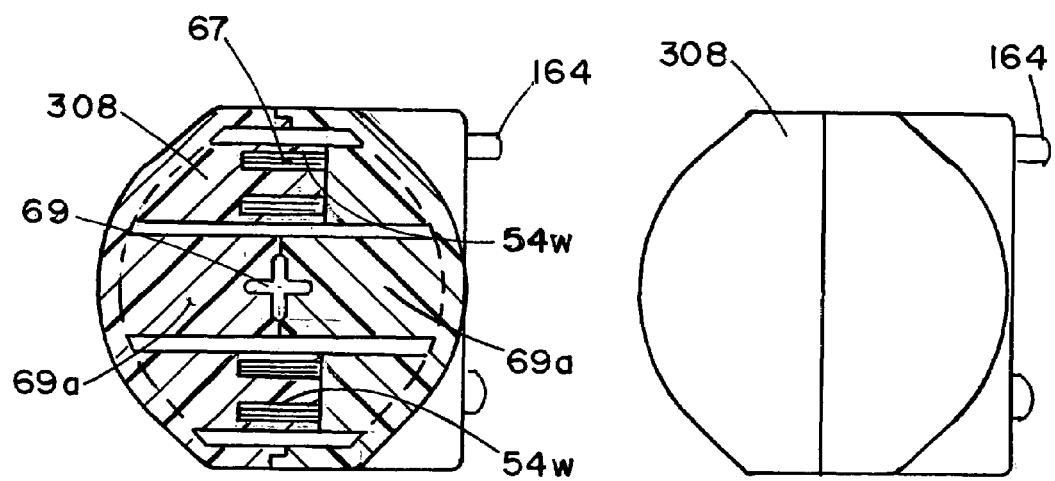
FIG. 70 is a cross-sectional view taken along lines 70—70 of FIG. 67.
FIG. 71 is a left end view of the apparatus shown in FIG. 64.

As in the earlier described embodiments of the invention, the present invention includes fill means, which are here carried by the first portion 306 of the outer housing. As before, the fill means functions to fill the reservoir 312 with the fluid to be dispensed. As best seen in FIG. 67, first housing portion 306 includes a fluid passageway 313 that is in communication with the inlet 312a of fluid reservoir 312. Proximate its lower end 313a, fluid passageway 313 communicates with a cavity 315 formed within the first portion of the housing. Disposed within cavity 315 is a pierceable elastomeric septum 317 that comprises a part of the fill means of this latest form of the invention. Septum 317 is held in position by a retainer 317a and is pierceable by the needle of the syringe which contains the medicinal fluid to be dispensed and which can be used in a conventional manner to fill or partially fill reservoir 312 via passageway 313. As the reservoir fills, and gases trapped within the reservoir will be vented via vents "V".

Turning particularly to FIGS. 76 through 83, the novel flow control means of the apparatus of this latest form of the invention is there shown. This important flow control means functions to precisely control the rate outwardly of fluid flow from reservoir 312 and toward the patient. In this latest form of the invention, the flow control means comprises a flow rate control assembly generally designated in the drawings by the numeral 314. This flow rate control assembly is non-rotatably mounted within housing portion 306 and includes an elongated spline 315 that functions to align the assembly within the outer housing, As best seen in FIGS. 76 and 77, this novel flow rate control assembly here comprises an inlet manifold 316 having an inlet port 318 (FIG. 76) that is in communication with the outlet 312a of the fluid reservoir 312 (FIG. 69) and an outlet manifold 320 that is interconnected with inlet manifold 316 by means of a plurality of interconnected flow rate control plates 322, 324, 326, 328, 330, 332, 334, 336, 338 and 340 (see also FIG. 80). The rate control plates can be interconnected by various well-known techniques including adhesive, sonic, thermal, laser and chemical bonding without disturbing the integrity of the flow channels. As indicated in FIGS. 83 and 84, outlet manifold 320 has a plurality of circumferentially spaced outlet ports, each of which is in communication with an outlet port of a selected one of the rate control plates. In a manner presently to be described, by using the selector means of the apparatus these circumferentially spaced outlet ports can be selectively brought into communication with outlet passageway 380 of the apparatus and with the administration line 341 of the administration set 343.

As best seen by referring to FIG. 80, each of the flow rate control plates is provided with an elongated micro channel of a particular configuration. These micro-flow channels can be formed in various ways known to those skilled in the art. For example, U.S. Pat. No. 6,176,962 issued to Soane et al. describes methods for constructing micro channel structures for use in micro fluidic manipulations. Similarly, International Publication WO 99/5694A1 describes such methods. When the rate control plates are assembled in the manner shown in FIGS. 80 and 83A, it is apparent that the micro channel formed in each of the rate control plates will cooperate with the adjacent planar surface of the next adjacent rate control plate to form a fluid flow control channel through which the fluid flowing into inlet 318 can controllably flow. As indicated in the drawings, one end of each of the micro channels is in communication with the inlet port 318 of the inlet manifold 316 via a center port 319 and the other end of each of the micro channel is in communication with a selected one of the circumferentially spaced outlet ports provided in the outlet manifold 320. More particularly, as can be seen by referring to FIGS. 80, 81 and 84 of the drawings, outlet 322a of rate control plate 322 is in communication with outlet 341 of outlet manifold 320; outlet 324a of rate control plate 324 is in communication with outlet 342 of outlet manifold 320; outlet 326a of control plate 326 is in communication with outlet 343 of manifold 320; outlet 328a of control plate 328 is in communication with outlet 344 of outlet manifold 320 and outlet 330a of rate control 330 is in communication with outlet 345 of outlet manifold 320, and. outlet 332a of rate control plate 332 is in communication with outlet 346 of outlet manifold 320. In similar fashion, outlet 334a of rate control plate 334 is in communication with outlet 347 of outlet manifold 320; outlet 336a of rate control plate 336 is in communication with outlet 348 of manifold 320 and outlet 338a of control plate 338 is in communication with outlet 349 of outlet manifold 320 and outlet 340a of rate control plate 340 is in communication with outlet 350 of outlet manifold 320.

With the construction of the flow control means shown in the drawings, fluid will flow from reservoir 312 into inlet port 318 of inlet manifold 316, through a filter member 353 (FIGS. 82A and 83) and thence into micro channel 354 formed in plate 322. By controlling the length, width and depth of the micro channel 354, the rate of fluid flow flowing outwardly of outlet 322a can be precisely controlled. In a manner presently to be described, the fluid will then flow onwardly toward the administration set via the flow regulation means of the invention. It is to be understood that micro channel 354 can take various forms and can be of varying length, width and depth to precisely control the rate of fluid flow their through.

Fluid flowing through inlet port 318 will also flow into micro channel 356 formed in rate control plate 324. Once again, depending upon the length, width and depth of micro channel 356, the rate of fluid flowing outwardly of outlet 324a can be precisely controlled. In similar manner, fluid flowing through inlet port 318 will fill micro channel 358 formed in rate control plate 326, will fill micro channel 360 formed in plate 328, will fill micro channel 362 formed in rate control plate 330, will fill rate control micro channel 364 formed in rate control plate 332, will fill rate control micro channel 366 formed in rate control plate 334, will fill rate control micro channel 368 formed in rate control plate 336, will fill flow control micro channel 370 formed in rate control plate 338 and will fill rate control micro channel 372 formed in rate control plate 340. After flowing through the rate control micro channels formed in the various indexedly aligned rate control plates, the fluid will flow onwardly toward outlet manifold 320 and will fill each of the stub passageways 375 formed therein (FIGS. 84 and 85). The rate of flow of fluid flowing outwardly of each of the outlet ports of the various rate control plates will, of course depend upon the configuration of the individual rate control micro channels formed in the rate control plates.

Figure 75:
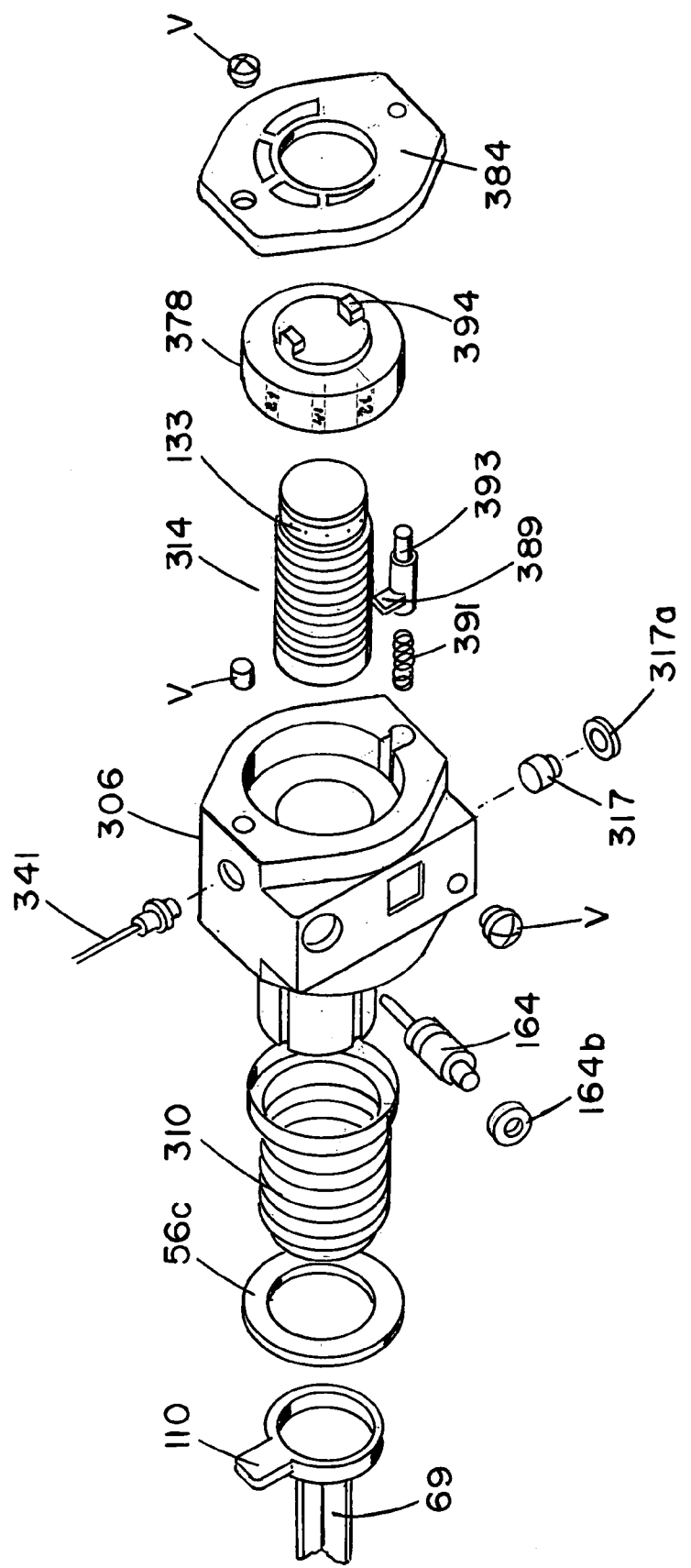
FIGS. 75 and 75C when considered together comprise a generally perspective exploded view of the assembly shown in FIG. 67. (hereinafter collectively referred to as FIG. 75)
Figures 75A, 75B, 75C:
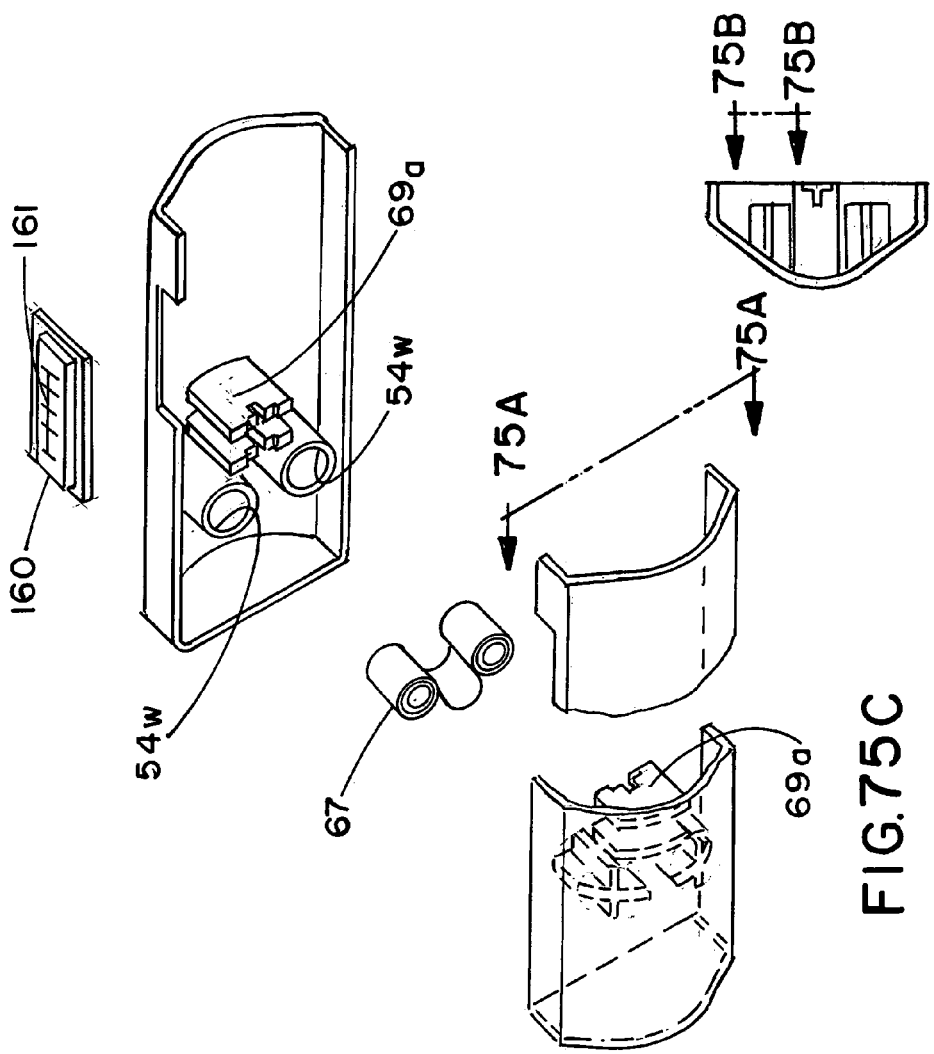
FIG. 75A is a view taken along lines 75A—75A of FIG. 75C.
FIG. 75B is a view taken along lines 75B—75B of FIG. 75A.
Figure 81:
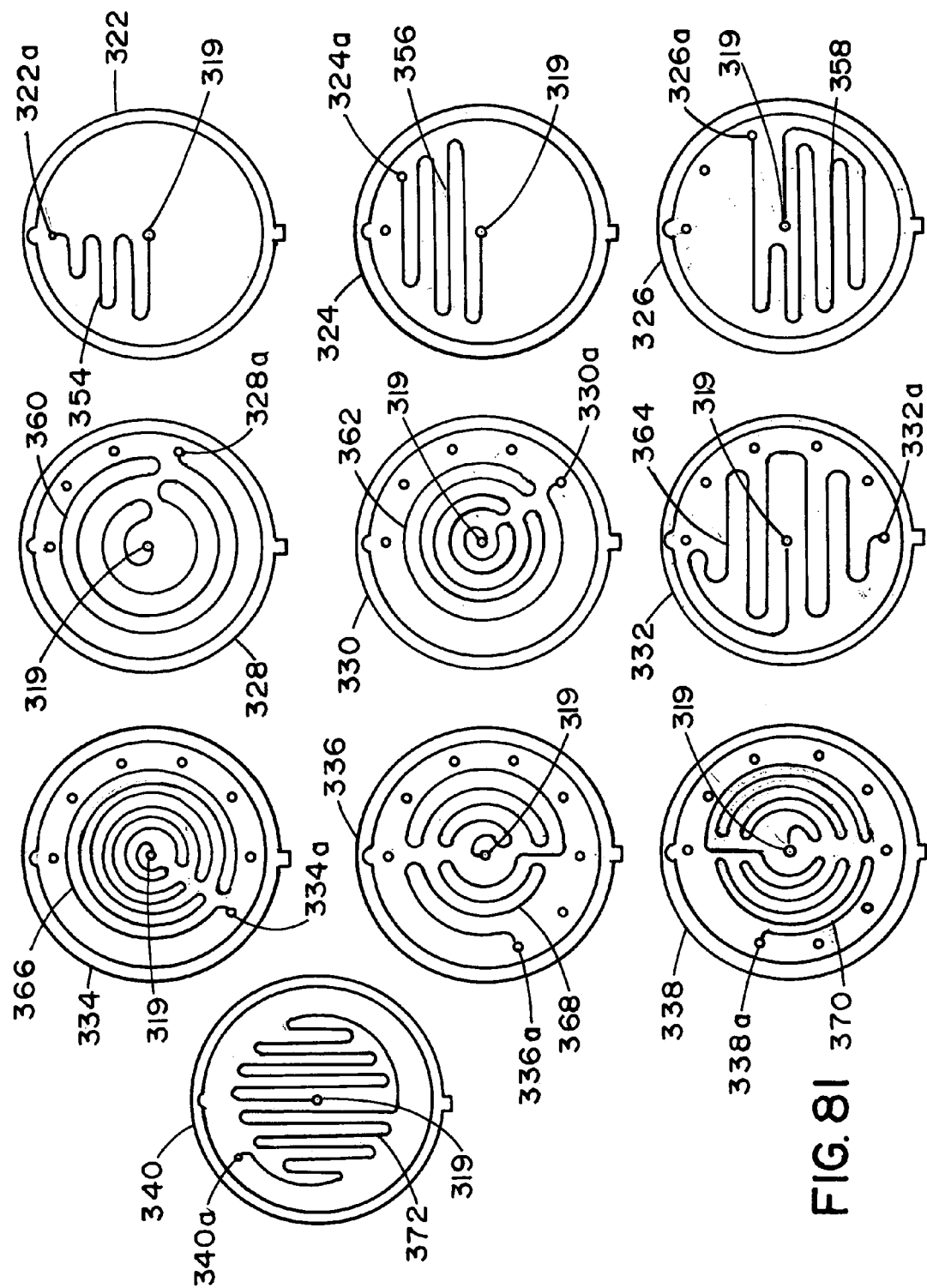
FIG. 81, when considered in its entirety, comprises a front view of each of the rate control plates of the assembly shown in FIGS. 80 and 80A.

As shown in FIG. 74, selector knob 378 is provided with a plurality of circumferentially spaced apart indexing cavities 379 that closely receive an indexing finger 389, which forms a part of the indexing means of the invention, which means comprises a front bezel 384 that is connected to the apparatus housing (see FIGS. 64 and 75). Indexing finger 389 is continuously urged into engagement with a selected one of the indexing cavities 379 by a coil spring 391 that also forms a part of the indexing means of the invention. Coil spring 391 can be compressed by an inward force exerted on an indexing shaft 393 that is movable from an extended position to an inward, finger release position wherein spring 391 is compressed and finger 389 is retracted from a selected indexing cavity 379. With finger 389 in its retracted position, it is apparent that control knob 378 can be freely rotated to a position wherein a gripping member 394 can be aligned with selected flow rate indicia 395 formed on the front bezel 384 of the apparatus housing.

When the selector knob is in the desired position and pressure is released on indexing shaft 393, spring 391 (FIG. 67) will urge finger 389 of the indexing means of the invention into locking engagement with one of the indexing cavities 379 (FIG. 74) thereby placing a selected one of flow control channels of a flow rate control plate in communication with flow passageway 378a (FIGS. 67A and 76) of the flow control knob. As the fluid flows outwardly of the apparatus due to the urging of the stored energy means or spring member 67, the bellows structure 310 will be collapsed and at the same time member 69 will travel inwardly of the housing. Member 69, which forms a part of the volume indicator means of the invention, includes a radially outwardly extending indicating finger 110 that is visible through a volume indicator window 160 that is provided in a second portion 308 of the apparatus housing and also comprises a part of the volume indicator means of the invention. Indicia 161, which are provided on indicator window 160 (FIG. 64), function to readily indicate to the caregiver the amount of fluid remaining within fluid reservoir 312 at any point in time.

Referring to FIGS. 64 and 73, disabling means, shown here as a disabling shaft 164 that is telescopically movable within a passageway formed within housing portion, functions in the manner previously described to disable the device.

Referring particularly to FIGS. 67, 76 and 77, a selector knob 378, which comprises a part of the selector means of the invention, is sealably connected to outlet manifold 320 by means of O-Rings "O" and is rotatable with respect thereto. As previously mentioned, this novel selector means of the invention functions to control the flow of fluid from outlet manifold 320 toward the administration set 343. More particularly, as illustrated in FIGS. 93, 93A and 93B, selector knob 378 is provided with a circumferentially extending flow channel 378a which is selectively in communication with stub passageways 375 of outlet manifold 320 depending upon the position of the selector knob. As illustrated in FIGS. 93A and 93B, the rearwardly extending. generally cylindrical, reduced diameter portion 378c of the control knob, which circumscribes the outlet manifold 320, is provided with a circumferentially extending, elastomeric band 382 which prevents fluid leakage between then the outlet manifold and the flange 378c. Outlet manifold 320 is also provided with a similarly configured, circumferentially extending, elastomeric band 384. As indicated in FIG. 93A, elastomeric band 384 has an opening 384a that is in alignment with fluid outlet passageway 380 formed in the first portion 306 of the outer housing (see also FIG. 67). Elastomeric band 382 also has an opening 382a which is aligned with a radially extending flow passageway 378b formed on portion 378c of the control knob, which, in turn, is in conimunication with circumferentially extending flow channel 378a (FIG. 93A). With this construction, when the control knob 378 is rotated to a position such as that illustrated in FIG. 93A, wherein one of the outlets of the outlet manifold 320 is in alignment with the opening 382a formed in the elastomeric band 382, fluid can flow from that outlet and into circumferentially extending flow channel 378a. From flow channel 378a, the fluid can flow into radially extending passageway 378b, through opening 384a and into passageway 380. From passageway 380, the fluid can flow onwardly into the dispensing means or administration set 343. The rate at which the fluid flows toward the administration set depends, of course, upon which rate control plate outlet is in communication with radial passageway 378b formed in the control knob. By way of example, with the control knob 378 in the position shown in FIG. 93A, it is to be observed that the fluid flowing toward the administration set is flowing from outlet 322a of rate control plate 322 and will flow at a rate determined by the configuration of rate control micro channel 354 (see FIGS. 80 and 80A).

Referring now to FIGS. 96 through 106, still another embodiment of the dispensing apparatus of the present invention is there illustrated and generally designated by the numeral 392. This alternate form of the apparatus of the invention is similar in some respects to that shown in FIGS. 64 through 95 and like numerals are used in FIGS. 96 through 106 to identify like components. The primary difference between this latest form of the invention and that discussed in the embodiment of FIGS. 64 through 95 concerns the provisions of a differently configured flow rate control means. More particularly, the flow rate control means of this latest form of the invention comprises a single fixed, non-variable flow rate control rather than a variable flow rate control as described in the immediately preceding paragraphs.

As best seen in FIG. 96, this latest form of the apparatus of the invention comprises an outer housing 394 having first and second portion 396 and 398 respectively. Disposed within outer housing 394 is an inner, expandable housing 310, which is identical in construction and operation to the expandable housing, which was described in connection with the embodiment of FIGS. 64 through 95.

Disposed within second portion 398 of outer housing 394 is the novel stored energy means of the invention for acting upon inner expandable housing 310 in a manner to cause the fluid contained within fluid reservoir 312 thereof to controllably flow outwardly of the housing (FIG. 101). In this latest form of the invention, this stored energy means is identical in construction and operation to that previously described and here comprises a constant force spring 67.

As in the earlier described embodiment of the invention, the present invention includes fill means which are carried by the first portion 396 of the outer housing. As before, the fill means functions to fill the reservoir 312 with the fluid to be dispensed. As best seen in FIG. 99, first portion 396 includes a fluid passageway 400 in communication with the inlet 312a of fluid reservoir 312. Proximate its lower end 400a, fluid passageway 400 communicates with a cavity 402 formed within the first portion of the housing. Disposed within cavity 402 is a pierceable septum 317 that comprises a part of the fill means of this latest form of the invention. Septum 317 is held in position by a retainer 317a and is pierceable by the needle of the syringe which contains the medicinal fluid to be dispensed and which can be used in a conventional manner to fill or partially fill reservoir 312 via passageway 400. As the fluid to be dispensed flows toward the fluid reservoir, any gases trapped within the reservoir will be vented to atmosphere through the vents "V".

Turning particularly to FIGS. 99 through 101, the alternate form of the flow control means of the apparatus of this latest form of the invention is there shown. As before, this alternate flow control means functions to precisely control the rate outwardly to fluid flow from reservoir 312 and toward the patient. In this latest form of the invention, the flow control means comprises a flow rate control assembly generally designated in the drawings by the numeral 404. This novel flow rate control assembly here comprises an inlet manifold 406 having an inlet port 408 that is in communication with the outlet 312a of the fluid reservoir 312 and a fixedly mounted, outlet manifold 410 that is interconnected with inlet manifold 406 by means of a pair of interconnected plates 412 and 414. Plate 412 is identical in construction and operation to the previously describe flow rate control plate 322 and is provided with a micro channel 354 (see also FIGS. 80 and 80A). Plate 414, on the other hand, is a generally cylindrically shaped plate having planar front and rear surfaces. With this construction, the rear surface of plate 414 cooperates with the micro channel 354 of plate 412 to provide a closed flow control channel which controls the rate of fluid flow from the reservoir toward the administration set of the apparatus of the invention. As indicated in the drawings, outlet manifold 410 has an outlet passageway 416 that is in communication with the outlet port of rate control plate 412.

With the construction of the flow control means shown in the drawings, fluid will flow from reservoir 312 into inlet port 408 of the inlet manifold and then into micro channel 354 formed in plate 412. By controlling the length, width and depth of the micro channel 354, the rate of fluid flow flowing into outlet passageway 416 can be precisely controlled. As previously mentioned, the fluid will flow from passageway 416 onwardly toward the administration set via the device outlet passageway 418 (FIG. 99).

As in the earlier described embodiments, that apparatus includes volume indicator means and disabling means of the character previously described which can be used to determine the volume of fluid remaining in the device reservoir and, when desired to disable the apparatus.

Referring now to FIGS. 107 through 118, yet another embodiment of the dispensing apparatus of the present invention is there illustrated and generally designated by the numeral 422. This alternate form of the apparatus of the invention is similar in some respects to that shown in FIGS. 49 through 63 and like numerals are used in FIGS. 107 through 118 to identify like components. The primary difference between this latest form of the invention and those previously discussed herein concerns the provision of a fill means, such as that shown in the embodiment of the invention illustrated in FIGS. 49 through 63 and the provision of a flow rate control means such as that shown in the embodiment of the invention illustrated in FIGS. 64 through 95.

As best seen in FIG. 107, the apparatus here comprises an outer housing 424 having first, second and third portions 426, 428 and 429 respectively. Disposed within outer housing 424 is an inner, expandable housing 430, which is generally similar in construction and operation to expandable housing 310, which housing was described in connection with the embodiment of FIGS. 64 through 95.

Also disposed within outer housing 424 is the novel stored energy means of the invention for acting upon inner expandable housing 430 in a manner to cause the fluid contained within the fluid reservoir thereof to controllably flow outwardly of the housing. In this latest form of the invention, this stored energy means is identical in construction and operation to that previously described and here comprises a constant force spring 67 of the character previously described.

As in the earlier described embodiments of the invention, the present invention includes fill means, which are here carried by the third portion 426 of the outer housing. As before, the fill means functions to fill the reservoir defined by bellows member 430 with the fluid to be dispensed. As best seen in FIG. 108, third housing portion 429 includes a fluid passageway 433 that is in communication with the inlet or passageway 435 of the fluid reservoir. Proximate its lower end 433a, fluid passageway 433 communicates with a cavity 436 formed within the third portion of the housing. Disposed within cavity 436 is a pierceable septum 317 that comprises a part of the fill means of this latest form of the invention. Septum 317, which is identical in construction and operation to that previously described, is held in position by a retainer 317a and is pierceable by the needle of the syringe which contains the medicinal fluid to be dispensed and which can be used in a conventional manner to fill or partially fill the device reservoir via passageway 433. As the reservoir fills, any gases trapped within the reservoir will be vented via vent "V".

Turning particularly to FIG. 108, the novel flow control means of the apparatus of this latest form of the invention is there shown and includes a flow rate control assembly generally designated by the numeral 314. This important flow control means, which is identical in construction and operation to that discussed in connection with the embodiment of the invention shown in FIGS. 64 through 95, functions to precisely control the rate outwardly of fluid flow from the device reservoir and toward the patient. As before, flow rate control assembly 314 is nonrotatably mounted within the outer housing and is of a construction illustrated in FIGS. 76 through 95. Reference should be made to these figure drawings and to the earlier discussion thereof to more completely understand the construction and operation of this unique flow rate control assembly of this latest form of the invention.

As shown in FIG. 108, a selector knob 378, which is of an identical construction to that previously described, is used to controllably rotate the flow rate control assembly. Selector knob 378 as operably associated with the indexing means of the invention, which means is also identical in construction and operation to that previously described.

As the fluid flows outwardly of the apparatus due to the urging of the stored energy means or spring member 67, the bellows structure 430 will be collapsed and at the same time member 69 will travel inwardly of the housing. Member 69, which forms a part of the volume indicator means of the invention, includes a radially outwardly extending indicating finger 110 that is visible through a volume indicator window 160 that is provided in a second portion 428 of the apparatus housing and also comprises a part of the volume indicator means of the invention. Indicia 161, which are provided on indicator window 160 (FIG. 107), function to readily indicate to the caregiver the amount of fluid remaining within fluid reservoir of the device at any point in time.

Referring to FIG. 107, disabling means, shown here as a disabling shaft 164 that is telescopically movable within a passageway formed within the housing portion, functions in the manner previously described to disable the device.

With regard to the fill means of this latest form of the invention, which is carried by the third portion 429 of the outer housing, as before, this important fill means functions to fill the device reservoir with the fluid to be dispensed. This fill means here comprises the previously described septum fill means and also includes the previously mentioned fill vials generally designated in FIG. 108 by the numerals 252 and 254 respectively.

Turning to FIGS. 108 and 113 through 118, the fill vials of the fill means of the dispensing apparatus of this latest form of the invention are there illustrated. These fill vials, which are of identical construction and operation to those shown in FIG. 52 and earlier described herein, comprise cartridge fill vial 252 and a lyophilized drug fill vial 254. As shown in FIG. 108, the third portion 429 of the housing also includes a first chamber 440 for telescopically receiving cartridge fill vial 252. As illustrated in FIG. 108, a hollow needle 442 is mounted within third portion 429 of the device housing and is located proximate the inboard end of chamber 440. Hollow needle 442 is adapted to pierce septum 236 when the cartridge fill vial 252 is inserted into chamber 440 and pushed forwardly into the position shown in FIG. 108.

With respect to second cartridge fill vial 254, this fill vial, which is more clearly illustrated in FIGS. 115 and 116 of the drawings comprises a container of special design that uniquely contains a lyophilized drug 262 that is separated from a reconstituting fluid 264 by a barrier stopper 266 (FIG. 115). Lyophilized drug 262 can, by way of example, comprise anti-infectives or various other types of beneficial agents. Cartridge fill vial 254 is identical in construction and operation to that shown in FIGS. 53 and 54 and previously described herein. As shown in FIG. 108, the third portion 429 of the housing also includes a second chamber 448 for telescopically receiving cartridge fill vial 254. As illustrated in FIG. 108, a hollow needle 450 is mounted within third portion 429 of the device housing and is located proximate the inboard end of chamber 448. Hollow needle 450 is adapted to pierce septum 274 when the cartridge fill vial 254 is inserted into chamber 448 and pushed forwardly into the position shown in FIG. 108.

As illustrated in FIG. 108, the vial cover 443 of portion 429 of the device housing includes a pair of spaced apart pusher members 445 and 447 which engage plungers 237 and 270 respectively to push them forwardly of their respective container reservoirs (see also FIGS. 111 and 112).

As the vial cover 443 is mated with the apparatus housing, the fluid contained in the vial reservoirs will be forced through the upper and lower hollow needles 442 and 450, passed the upper umbrella check valves 453 mounted within third housing portion 429, into a stub passageways 455, into passageways 433 and 435 and finally into the device reservoir. As the fluid flows into the device reservoir, it will compress the stored energy means, or constant force spring 67 in the manner previously described.

Turning to FIGS. 117 and 118, an alternate form of drug intermixing vial is there shown. This fill cartridge is identical in construction and operation to that previously described herein and illustrated in FIGS. 55 and 56. This alternate form of drug intermixing vial can be used in place of vial 254 during the reservoir filling step.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing apparatus for dispensing fluids to a patient comprising:
   (a) an outer housing having first, second and third portions;
   (b) an expandable housing disposed within said outer housing, said expandable housing having a fluid reservoir provided with an inlet for permitting fluid flow into said fluid reservoir and an outlet for permitting fluid flow from said fluid reservoir, said expandable housing comprising a bellows structure having an accordion-like side wall movable from a substantially collapsed configuration to a substantially expanded configuration by fluid flowing into said fluid reservoir;
   (c) stored energy means disposed within said second portion of said outer housing for exerting a force upon said inner expandable housing to cause the fluid contained within said fluid reservoir to controllably flow through said outlet, said stored energy means comprising a constant force extension spring carried within said outer housing, said constant force extension spring being expandable by fluid flowing into said fluid reservoir and being retractable to cause fluid flow from said fluid reservoir;
   (d) fill means carried by said outer housing for filling said reservoir with the fluid to be dispensed, said fill means comprising a vial carried within said third portion of said outer housing, said third portion of said outer housing including:
      (i) a fluid passageway;
      (ii) a first chamber for telescopically receiving said vial; and (iii) an elongated support mounted within said first chamber, said elongated support having an elongated hollow needle, said hollow needle defining a flow passageway in communication with said fluid passageway;

(e) dispensing means carried by said outer housing for dispensing fluid to the patient; and flow control means connected to said outer housing for controlling fluid flow between said reservoir and said dispensing means.

2. A dispensing apparatus for dispensing fluids to a patient comprising:

(a) an outer housing having first, second and third portions;

(b) an expandable housing disposed within said outer housing, said expandable housing having a fluid reservoir provided with an inlet for permitting fluid flow into said fluid reservoir and an outlet for permitting fluid flow from said fluid reservoir, said expandable housing comprising a bellows structure having an accordion-like side wall movable from a substantially collapsed configuration to a substantially expanded configuration by fluid flowing into said fluid reservoir;

(c) stored energy means disposed within said second portion of said outer housing for exerting a force upon said inner expandable housing to cause the fluid contained within said fluid reservoir to controllably flow through said outlet, said stored energy means comprising a constant force extension spring carried within said outer housing, said constant force extension spring being expandable by fluid flowing into said fluid reservoir and being retractable to cause fluid flow from said fluid reservoir;

(d) fill means carried by said outer housing for filling said reservoir with the fluid to be dispensed, said fill means comprising first and second vials carried within said third portion of said outer housing, said third portion of said outer housing including:

(i) a fluid passageway;

(ii) a first chamber for telescopically receiving said first fill vial;

(iii) an elongated support mounted within said first chamber, said elongated support having an elongated hollow needle, said hollow needle defining a flow passageway in communication with said fluid passageway;

(iv) a second chamber for telescopically receiving said second fill vial; and an elongated support mounted within said second chamber, said elongated support having an elongated hollow needle, said hollow needle defining a flow passageway in communication with said fluid passageway;

(e) dispensing means carried by said outer housing for dispensing fluid to the patient; and (f) flow control means connected to said outer housing for controlling fluid flow between said reservoir and said dispensing means.

3. A dispensing apparatus for dispensing fluids to a patient comprising:

(a) an outer housing having first, second and third portions;

(b) an expandable housing disposed within said outer housing, said expandable housing having a fluid reservoir provided with an inlet for permitting fluid flow into said fluid reservoir and an outlet for permitting fluid flow from said fluid reservoir,said expandable housing comprising a bellows structure having an accordion-like side wall movable from a substantially collapsed configuration to a substantially expanded configuration by fluid flowing into said fluid reservoir;

(c) stored energy means disposed within said second portion of said outer housing for exerting a force upon said inner expandable housing to cause the fluid contained within said fluid reservoir to controllably flow through said outlet, said stored energy means comprising a constant force extension spring carried within said outer housing, said constant force extension spring being expandable by fluid flowing into said fluid reservoir and being retractable to cause fluid flow from said fluid reservoir;

(d) fill means carried by said outer housing for filling said reservoir with the fluid to be dispensed, said fill means comprising a vial carried within said third portion of said outer housing;

(e) dispensing means carried by said outer housing for dispensing fluid to the patient; and flow control means connected to said outer housing for controlling fluid flow between said reservoir and said dispensing means, said flow control means comprising a flow control assembly including:

(i) an outer casing disposed within said first portion of said outer housing, said outer casing having a plurality of circumferentially spaced-apart fluid outlets in communication with said fluid reservoir;

(ii) a flow control member mounted within said outer casing, said flow control member having a plurality of elongated flow control channels, each of said plurality of elongated flow control channels having an inlet and an outlet; and (iii) selector means rotatably connected to said second portion of said outer housing for rotating said flow control member.

4. The apparatus as defined in claim 3 in which said flow control assembly further comprises distribution means formed in said flow control member for distributing fluid from said fluid reservoir to each of said plurality of elongated flow control channels.

5. The apparatus as defined in claim 4, in which said flow control member is provided with an inlet passageway in communication with said fluid reservoir and in which said flow control assembly further includes filter means carried by said flow control member for filtering fluid flowing toward said distribution means.

6. The apparatus as defined in claim 5 in which said distribution means comprises a plurality of radially extending flow passageways formed in said flow control member.

7. The apparatus as defined in claim 6 in which said first portion of said outer housing is provided with a fluid flow passageway and in which said selector means comprises a selector knob connected to said flow control member, said selector knob having finger gripping means for imparting rotation to said selector knob to align said outlet of a selected one of said elongated flow control channels with said fluid flow passageway in said first portion of said outer housing.

8. The apparatus as defined in claim 7 further including volume indicator means carried by said outer housing for indicating the volume of fluid remaining in said fluid reservoir.

9. The apparatus as defined in claim 7 further including disabling means carried by said outer housing for preventing fluid flow toward said dispensing means.

* * * * *